US010436787B2

(12) United States Patent
Guette et al.

(10) Patent No.: US 10,436,787 B2
(45) Date of Patent: Oct. 8, 2019

(54) OLFACTOMEDIN-4, NEUDESIN AND DESMOPLAKIN AS BIOMARKERS OF BREAST CANCER

(71) Applicants: Institut de Cancerologie de L'Ouest, Angers (FR); Universite D'Angers, Angers (FR); Institut National de la Sante et de la Recherche Medicale (INSERM), Paris (FR)

(72) Inventors: Catherine Guette, La Possonniere (FR); Pedro Raro, Arville (FR); Olivier Coqueret, Angers (FR); Benjamin Barre, Bain sur Longuenee (FR); Mario Campone, Nantes (FR)

(73) Assignees: Institut de Cancerologie de L'Ouest, Angers (FR); Universite D'Angers, Angers (FR); Institut National de la Sante de la Recherche Medicale (INSERM), Paris (FR)

( * ) Notice: Subject to any disclaimer, the term of this patent is extended or adjusted under 35 U.S.C. 154(b) by 0 days.

(21) Appl. No.: 15/038,135

(22) PCT Filed: Nov. 24, 2014

(86) PCT No.: PCT/EP2014/075427
§ 371 (c)(1),
(2) Date: May 20, 2016

(87) PCT Pub. No.: WO2015/075242
PCT Pub. Date: May 28, 2015

(65) Prior Publication Data
US 2016/0291022 A1    Oct. 6, 2016

(30) Foreign Application Priority Data
Nov. 22, 2013    (EP) .................................... 13306604

(51) Int. Cl.
*G01N 33/574*    (2006.01)
*G01N 33/50*     (2006.01)

(52) U.S. Cl.
CPC ... *G01N 33/57415* (2013.01); *G01N 33/5011* (2013.01); *G01N 2333/47* (2013.01); *G01N 2333/4703* (2013.01); *G01N 2333/475* (2013.01); *G01N 2333/71* (2013.01); *G01N 2500/10* (2013.01); *G01N 2570/00* (2013.01); *G01N 2800/52* (2013.01)

(58) Field of Classification Search
CPC .............................. G01N 33/53; G01N 33/574
See application file for complete search history.

(56) References Cited

U.S. PATENT DOCUMENTS

| 6,258,540 B1 * | 7/2001 | Lo ........................ C12Q 1/6879 435/440 |
| 6,355,623 B2 * | 3/2002 | Seidman ................ A61K 31/52 514/263.4 |
| 2007/0037228 A1 | 2/2007 | Moecks et al. |
| 2011/0085982 A1 | 4/2011 | Seewaldt et al. |
| 2011/0229504 A1 * | 9/2011 | Fritsche ............. A61K 38/1709 424/185.1 |
| 2015/0005183 A1 * | 1/2015 | Krizman .......... G01N 33/57415 506/9 |
| 2016/0003828 A1 * | 1/2016 | Matsuura ......... G01N 33/57415 435/7.23 |
| 2016/0291021 A1 * | 10/2016 | Guette ............. G01N 33/57415 |

FOREIGN PATENT DOCUMENTS

| WO | WO-2008075922 A1 * | 6/2008 | ........ C07K 14/4748 |
| WO | 2011/113047 A2 | 9/2011 | |
| WO | WO-2012031008 A2 * | 3/2012 | .......... C12Q 1/6806 |
| WO | 2012/117267 A1 | 9/2012 | |
| WO | 2013/033609 A2 | 3/2013 | |

OTHER PUBLICATIONS

Henry and Hayes (The Oncologist 2006 11:541-552) (Year: 2006).*
Hornbeck et al. (Current Protocols in Mol. Biol. Enzyme-Linked Immunosorbent Assays (ELISA) 2000, 11.2.1-11.2.22) (Year: 2000).*
Oue et al. (Int. J. Cancer 2009 125: 2383-2392) (Year: 2009).*
International Search Report Issued in Corresponding International Application No. PCT/EP2014/075427, dated Apr. 21, 2015.
Koshida et al., Specific Overexpression of OLFM4GW112/hGC?1 mRNA in Colon, Breast and Lung Cancer Tissues Detected Using Quantitative Analysis, Cancer Science, Japanese Cancer Association, VOI. 98, No. 3, Tokyo, JP, Mar. 1, 2007, pp. 315-320.
Independent UK Panel on Breast Cancer Screeing, The Benefits and Harms of Breast Cancer Screening: an Independent Review, The Lancet, 2012, 380(9855), pp. 1778-1786.
Liu, W. et al, The Glycoprotein hGC-1 Binds to Cadherin and Lectins, Experimental Cell Research, 2006, vol. 312, pp. 1785-1797.
Zhang, X. et al, GW112, A Novel Antiapoptotic Protein That Promotes Tumor Growth, Cancer Research, Apr. 1, 2004, vol. 64, pp. 2474-2481.
Kobayashi, D. et al, Olfactomedin 4 Promotes S-phase Transition in Proliferation of Pancreatic Cancer Cells, Cancer Science, Mar. 2007, vol. 98, No. 3, pp. 334-340, Japanese Cancer Association, Tokyo, JP.
Kimura, I. et al, Neurotrophic Effects of Neudesin in the Central Nervous System, Frontiers in Neuroscience, Jun. 25, 2013, vol. 7, Article 111, pp. 1-5.

(Continued)

*Primary Examiner* — Peter J Reddig
(74) *Attorney, Agent, or Firm* — Banner & Witcoff, Ltd.

(57) ABSTRACT

The present invention is in the technical field of breast cancer management, and more particularly relates to the diagnosis of breast cancer. The invention is more particularly based on the finding that specific biomarkers (olfactomedin-4, neudesin and desmoplakin) are abberantly expressed in the blood of breast cancer patients.

15 Claims, 15 Drawing Sheets
Specification includes a Sequence Listing.

(56) References Cited

OTHER PUBLICATIONS

Leung, C.L. et al, Plakins: A Family of Versatile Cytolinker Proteins, Trends in Cell Biology, Jan. 2002, vol. 12, No. 1, pp. 37-45.
Allen, E et al, Mice Expressing a Mutant Desmosomal Cadherin Exhibit Abnormalities in Desmosomes, Proliferation, and Epidermal Differentiation, The Journal of Cell Biology, Jun. 1996, vol. 133, No. 6, pp. 1367-1382.
Wan, H. et al, Increased Keratinocyte Proliferation Initiated Through Downregulation of Desmoplakin by RNA Interference, Experimental Cell Research, 2007, vol. 313, pp. 2336-2344.
Rickelt, S. et al, Upregulation of Plakophilin-2 and its Acquisition to Adherens Junctions Identifies a Novel Molecular Ensemble of Cell-Cell-Attachment Characteristic for Transformed Mesenchymal Cells, International Journal of Cancer, 2009, vol. 125, pp. 2036-2048.
Jonkman, M.F. et al, Loss of Desmoplakin Tail Causes Lethal Acantholytic Epidermolysis Bullosa, The American Journal of Human Genetics, 2005, vol. 77, pp. 653-660.
Kowalczyk, A.P. et al, The Amino-terminal Domain of Desmoplakin Binds to Plakoglobin and Clusters Desmosomal Cadherin-Plakoglobin Complexes, The Journal of Cell Biology, Nov. 3, 1997, vol. 139, No. 3, pp. 773-784.
Hou, H.W. et al, Isolation and Retrieval of Circulating Tumor Cells Using Centrifugal Forces, Scientific Reports, 2013, 3:1259.
Reeves, J.R. et al, Measurement of Protein Expression A Technical Overview, Methods in Molecular Medicine; 2000, vol. 39, chapter 51, p. 471-483.
Hamelinck, D. et al, Optimized Normalization for Antibody Microarrays and Application to Serum-Protein Profiling, Molecular & Cellular Proteomics, 2005, vol. 4.6, pp. 773-784.
Kohler, G. et al, Continuous Cultures of Fused Cells Secreting Antibody of Predefined Specificity, Nature, Aug. 7, 1975, vol. 256, pp. 495-497.
Kozbor, D. et al, The Production of Monoclonal Antibodies from Human Lymphocytes, Immunology Today, 1983, vol. 4, No. 3, pp. 72-79.
Roder, J.C. et al, The EBV-Hybridoma Technique, Methods in Enzymology, 1986, vol. 121, pp. 140-167.
Huse, W.D. et al, Generation of a Large Combinatorial Library of the Immunoglobulin Repertoire in Phage Lambda, Science, Dec. 8, 1989, vol. 246, pp. 1275-1281.
Weigelt, B. et al, Unraveling the Microenvironmental Influences on the Normal Mammary Gland and Breast Cancer, Semin Cancer Biol, Oct. 2008, 18(5), pp. 311-321.
Kenny, P.A. et al, The Morphologies of Breast Cancer Cell Lines in Three-dimensional Assays Correlate with their Profiles of Gene Expression, Molecular Oncology, Jun. 2007, 1(1), pp. 84-96.
Li, Q. et al, Three-Dimensional Overlay Culture Models of Human Breast Cancer Reveal a Critical Sensitivity to Mitogen-Activated Protein Kinase Kinase Inhibitors, The Journal of Pharmacology and Experimental Therapeutics, 2010, 332(3): 821-828.
Mitchell, Peter, A Perspective on Protein Microarrays, Nature Biotechnology, Mar. 2002, vol. 20, pp. 225-229.
Haab, Brian B., Antibody Arrays in Cancer Research, Molecular & Cellular Proteomics, 2005, vol. 4.4, pp. 377-383.
Eckel-Passow, J.E. et al, Experimental Design and Analysis of Antibody Microarrays: Applying Methods from cDNA Arrays, Cancer Res, 2005, 65(8), pp. 2985-2989.
Kingsmore, Stephen F., Multiplexed Protein Measurement: Technologies and Applications of Protein and Antibody Arrays, Nat Rev Drug Discov, Apr. 2006; 5(4), pp. 310-320.
Chandra, H. et al, Protein Microarrays and Novel Detection Platforms, Expert Rev. Proteomics, 2011, 8(1), pp. 61-79.
Schenk, S. et al, A High Confidence, Manually Validated Human Blood Plasma Protein Reference Set, BMC Medical Genomics, 2008, 15, 1:41.
Cao, Z. et al, Additions to the Human Plasma Proteome via a Tandem MARS Depletion iTRAQ-Based Workflow, International Journal of Proteomics, 2013, vol. 2013, No. 654356, pp. 1-8.
Imbalzano, K.M. et al, Increasingly Transformed MCF-10A Cells have a Progressively Tumor-like Phenotype in Three-dimensional Basement Membrane Culture, Cancer Cell International, 2009, 9:7. doi: 10.1186/1475-2867-9-7.
Wisniewski, J.R. et al, Universal Sample Preparation Method for Proteome Analysis, Nature Methods, May 2009, vol. 6, No. 5, pp. 359-362.
Shilov, I.V. et al, The Paragon Algorithm, a Next Generation Search Engine That Uses Sequence Temperature Values and Feature Probabilities to Identify Peptides from Tandem Mass Spectra, Molecular & Cellular Proteomics, 2007, vol. 6.9, pp. 1638-1655.
Schwacke, J.H. et al, iQuantitator: A Tool for Protein Expression Inference using iTRAQ, BMC Bioinformatics, 2009, 10, 342.
Grant, J.E. et al., Quantification of Protein Expression Changes in the Aging Left Ventricle of Rattus norvegicus, J. Proteome Res., Sep. 2009, 8(9), 4252-4263.
Konishi, H. et al, Knock-in of Mutant K-ras in Nontumorigenic Human Epithelial Cells as a New Model for Studying K-ras-Mediated Transformation, Cancer Res, 2007, 67: (18), pp. 8460-8467.
Sardanelli, F. et al, Breast MR Imaging in Women at High-risk of Breast Cancer. Is Something Changing in Early Breast Cancer Detection?, Eur Radiol, 2007, vol. 17, pp. 873-887.

* cited by examiner

A

B

C

D

A

B

SEQUENCE LISTING

```
<160> NUMBER OF SEQ ID NOS: 4

<210> SEQ ID NO 1
<211> LENGTH: 510
<212> TYPE: PRT
<213> ORGANISM: homo sapiens
<220> FEATURE:
<221> NAME/KEY: MISC_FEATURE
<223> OTHER INFORMATION: amino acid sequence of Olfactomedin 4

<400> SEQUENCE: 1

Met Arg Pro Gly Leu Ser Phe Leu Leu Ala Leu Leu Phe Phe Leu Gly
1               5                   10                  15

Gln Ala Ala Gly Asp Leu Gly Asp Val Gly Pro Pro Ile Pro Ser Pro
                20                  25                  30

Gly Phe Ser Ser Phe Pro Gly Val Asp Ser Ser Ser Ser Phe Ser Ser
            35                  40                  45

Ser Ser Arg Ser Gly Ser Ser Ser Arg Ser Leu Gly Ser Gly Gly
        50                  55                  60

Ser Val Ser Gln Leu Phe Ser Asn Phe Thr Gly Ser Val Asp Asp Arg
65                  70                  75                  80

Gly Thr Cys Gln Cys Ser Val Ser Leu Pro Asp Thr Thr Phe Pro Val
                85                  90                  95

Asp Arg Val Glu Arg Leu Glu Phe Thr Ala His Val Leu Ser Gln Lys
                100                 105                 110
```

```
Phe Glu Lys Glu Leu Ser Lys Val Arg Glu Tyr Val Gln Leu Ile Ser
            115                 120                 125
Val Tyr Glu Lys Lys Leu Leu Asn Leu Thr Val Arg Ile Asp Ile Met
        130                 135                 140
Glu Lys Asp Thr Ile Ser Tyr Thr Glu Leu Asp Phe Glu Leu Ile Lys
145                 150                 155                 160
Val Glu Val Lys Glu Met Glu Lys Leu Val Ile Gln Leu Lys Glu Ser
                165                 170                 175
Phe Gly Gly Ser Ser Glu Ile Val Asp Gln Leu Glu Val Glu Ile Arg
            180                 185                 190
Asn Met Thr Leu Leu Val Glu Lys Leu Glu Thr Leu Asp Lys Asn Asn
        195                 200                 205
Val Leu Ala Ile Arg Arg Glu Ile Val Ala Leu Lys Thr Lys Leu Lys
    210                 215                 220
Glu Cys Glu Ala Ser Lys Asp Gln Asn Thr Pro Val Val His Pro Pro
225                 230                 235                 240
Pro Thr Pro Gly Ser Cys Gly His Gly Gly Val Val Asn Ile Ser Lys
                245                 250                 255
Pro Ser Val Val Gln Leu Asn Trp Arg Gly Phe Ser Tyr Leu Tyr Gly
            260                 265                 270
Ala Trp Gly Arg Asp Tyr Ser Pro Gln His Pro Asn Lys Gly Leu Tyr
        275                 280                 285
Trp Val Ala Pro Leu Asn Thr Asp Gly Arg Leu Leu Glu Tyr Tyr Arg
    290                 295                 300
Leu Tyr Asn Thr Leu Asp Asp Leu Leu Leu Tyr Ile Asn Ala Arg Glu
305                 310                 315                 320
Leu Arg Ile Thr Tyr Gly Gln Gly Ser Gly Thr Ala Val Tyr Asn Asn
                325                 330                 335
Asn Met Tyr Val Asn Met Tyr Asn Thr Gly Asn Ile Ala Arg Val Asn
            340                 345                 350
Leu Thr Thr Asn Thr Ile Ala Val Thr Gln Thr Leu Pro Asn Ala Ala
        355                 360                 365
Tyr Asn Asn Arg Phe Ser Tyr Ala Asn Val Ala Trp Gln Asp Ile Asp
    370                 375                 380
Phe Ala Val Asp Glu Asn Gly Leu Trp Val Ile Tyr Ser Thr Glu Ala
385                 390                 395                 400
Ser Thr Gly Asn Met Val Ile Ser Lys Leu Asn Asp Thr Thr Leu Gln
                405                 410                 415
Val Leu Asn Thr Trp Tyr Thr Lys Gln Tyr Lys Pro Ser Ala Ser Asn
            420                 425                 430
Ala Phe Met Val Cys Gly Val Leu Tyr Ala Thr Arg Thr Met Asn Thr
        435                 440                 445
Arg Thr Glu Glu Ile Phe Tyr Tyr Tyr Asp Thr Asn Thr Gly Lys Glu
    450                 455                 460
Gly Lys Leu Asp Ile Val Met His Lys Met Gln Glu Lys Val Gln Ser
465                 470                 475                 480
Ile Asn Tyr Asn Pro Phe Asp Gln Lys Leu Tyr Val Tyr Asn Asp Gly
                485                 490                 495
Tyr Leu Leu Asn Tyr Asp Leu Ser Val Leu Gln Lys Pro Gln
            500                 505                 510

<210> SEQ ID NO 2
<211> LENGTH: 172
<212> TYPE: PRT
```

<213> ORGANISM: homo sapiens
<220> FEATURE:
<221> NAME/KEY: MISC_FEATURE
<223> OTHER INFORMATION: amino acid sequence of Neudesin

<400> SEQUENCE: 2

```
Met Val Gly Pro Ala Pro Arg Arg Leu Arg Pro Leu Ala Ala Leu
1               5                   10                  15

Ala Leu Val Leu Ala Leu Ala Pro Gly Leu Pro Thr Ala Arg Ala Gly
            20                  25                  30

Gln Thr Pro Arg Pro Ala Glu Arg Gly Pro Pro Val Arg Leu Phe Thr
            35                  40                  45

Glu Glu Glu Leu Ala Arg Tyr Gly Gly Glu Glu Asp Gln Pro Ile
50                  55                  60

Tyr Leu Ala Val Lys Gly Val Val Phe Asp Val Thr Ser Gly Lys Glu
65                  70                  75                  80

Phe Tyr Gly Arg Gly Ala Pro Tyr Asn Ala Leu Thr Gly Lys Asp Ser
                85                  90                  95

Thr Arg Gly Val Ala Lys Met Ser Leu Asp Pro Ala Asp Leu Thr His
                100                 105                 110

Asp Thr Thr Gly Leu Thr Ala Lys Glu Leu Glu Ala Leu Asp Glu Val
                115                 120                 125

Phe Thr Lys Val Tyr Lys Ala Lys Tyr Pro Ile Val Gly Tyr Thr Ala
130                 135                 140

Arg Arg Ile Leu Asn Glu Asp Gly Ser Pro Asn Leu Asp Phe Lys Pro
145                 150                 155                 160

Glu Asp Gln Pro His Phe Asp Ile Lys Asp Glu Phe
                165                 170
```

<210> SEQ ID NO 3
<211> LENGTH: 2871
<212> TYPE: PRT
<213> ORGANISM: homo sapiens
<220> FEATURE:
<221> NAME/KEY: MISC_FEATURE
<223> OTHER INFORMATION: amino acid sequence of Desmoplakin isoform 1

<400> SEQUENCE: 3

```
Met Ser Cys Asn Gly Gly Ser His Pro Arg Ile Asn Thr Leu Gly Arg
1               5                   10                  15

Met Ile Arg Ala Glu Ser Gly Pro Asp Leu Arg Tyr Glu Val Thr Ser
            20                  25                  30

Gly Gly Gly Gly Thr Ser Arg Met Tyr Tyr Ser Arg Arg Gly Val Ile
            35                  40                  45

Thr Asp Gln Asn Ser Asp Gly Tyr Cys Gln Thr Gly Thr Met Ser Arg
50                  55                  60

His Gln Asn Gln Asn Thr Ile Gln Glu Leu Leu Gln Asn Cys Ser Asp
65                  70                  75                  80

Cys Leu Met Arg Ala Glu Leu Ile Val Gln Pro Glu Leu Lys Tyr Gly
                85                  90                  95

Asp Gly Ile Gln Leu Thr Arg Ser Arg Glu Leu Asp Glu Cys Phe Ala
                100                 105                 110

Gln Ala Asn Asp Gln Met Glu Ile Leu Asp Ser Leu Ile Arg Glu Met
                115                 120                 125

Arg Gln Met Gly Gln Pro Cys Asp Ala Tyr Gln Lys Arg Leu Leu Gln
130                 135                 140

Leu Gln Glu Gln Met Arg Ala Leu Tyr Lys Ala Ile Ser Val Pro Arg
```

```
                145                 150                 155                 160
        Val Arg Arg Ala Ser Ser Lys Gly Gly Gly Tyr Thr Cys Gln Ser
                                165                 170                 175
        Gly Ser Gly Trp Asp Glu Phe Thr Lys His Val Thr Ser Glu Cys Leu
                            180                 185                 190
        Gly Trp Met Arg Gln Arg Ala Glu Met Asp Met Val Ala Trp Gly
                        195                 200                 205
        Val Asp Leu Ala Ser Val Glu Gln His Ile Asn Ser His Arg Gly Ile
                    210                 215                 220
        His Asn Ser Ile Gly Asp Tyr Arg Trp Gln Leu Asp Lys Ile Lys Ala
        225                 230                 235                 240
        Asp Leu Arg Glu Lys Ser Ala Ile Tyr Gln Leu Glu Glu Tyr Glu
                            245                 250                 255
        Asn Leu Leu Lys Ala Ser Phe Glu Arg Met Asp His Leu Arg Gln Leu
                        260                 265                 270
        Gln Asn Ile Ile Gln Ala Thr Ser Arg Glu Ile Met Trp Ile Asn Asp
                    275                 280                 285
        Cys Glu Glu Glu Glu Leu Leu Tyr Asp Trp Ser Asp Lys Asn Thr Asn
                290                 295                 300
        Ile Ala Gln Lys Gln Glu Ala Phe Ser Ile Arg Met Ser Gln Leu Glu
        305                 310                 315                 320
        Val Lys Glu Lys Glu Leu Asn Lys Leu Lys Gln Glu Ser Asp Gln Leu
                            325                 330                 335
        Val Leu Asn Gln His Pro Ala Ser Asp Lys Ile Glu Ala Tyr Met Asp
                        340                 345                 350
        Thr Leu Gln Thr Gln Trp Ser Trp Ile Leu Gln Ile Thr Lys Cys Ile
                    355                 360                 365
        Asp Val His Leu Lys Glu Asn Ala Ala Tyr Phe Gln Phe Phe Glu Glu
                370                 375                 380
        Ala Gln Ser Thr Glu Ala Tyr Leu Lys Gly Leu Gln Asp Ser Ile Arg
        385                 390                 395                 400
        Lys Lys Tyr Pro Cys Asp Lys Asn Met Pro Leu Gln His Leu Leu Glu
                            405                 410                 415
        Gln Ile Lys Glu Leu Glu Lys Glu Arg Glu Lys Ile Leu Glu Tyr Lys
                        420                 425                 430
        Arg Gln Val Gln Asn Leu Val Asn Lys Ser Lys Ile Val Gln Leu
                    435                 440                 445
        Lys Pro Arg Asn Pro Asp Tyr Arg Ser Asn Lys Pro Ile Ile Leu Arg
                450                 455                 460
        Ala Leu Cys Asp Tyr Lys Gln Asp Gln Lys Ile Val His Lys Gly Asp
        465                 470                 475                 480
        Glu Cys Ile Leu Lys Asp Asn Asn Glu Arg Ser Lys Trp Tyr Val Thr
                            485                 490                 495
        Gly Pro Gly Gly Val Asp Met Leu Val Pro Ser Val Gly Leu Ile Ile
                        500                 505                 510
        Pro Pro Pro Asn Pro Leu Ala Val Asp Leu Ser Cys Lys Ile Glu Gln
                    515                 520                 525
        Tyr Tyr Glu Ala Ile Leu Ala Leu Trp Asn Gln Leu Tyr Ile Asn Met
                530                 535                 540
        Lys Ser Leu Val Ser Trp His Tyr Cys Met Ile Asp Ile Glu Lys Ile
        545                 550                 555                 560
        Arg Ala Met Thr Ile Ala Lys Leu Lys Thr Met Arg Gln Glu Asp Tyr
                            565                 570                 575
```

```
Met Lys Thr Ile Ala Asp Leu Glu Leu His Tyr Gln Glu Phe Ile Arg
            580                 585                 590

Asn Ser Gln Gly Ser Glu Met Phe Gly Asp Asp Lys Arg Lys Ile
        595                 600                 605

Gln Ser Gln Phe Thr Asp Ala Gln Lys His Tyr Gln Thr Leu Val Ile
        610                 615                 620

Gln Leu Pro Gly Tyr Pro Gln His Gln Thr Val Thr Thr Glu Ile
625                 630                 635                 640

Thr His His Gly Thr Cys Gln Asp Val Asn His Asn Lys Val Ile Glu
                645                 650                 655

Thr Asn Arg Glu Asn Asp Lys Gln Glu Thr Trp Met Leu Met Glu Leu
            660                 665                 670

Gln Lys Ile Arg Arg Gln Ile Glu His Cys Glu Gly Arg Met Thr Leu
        675                 680                 685

Lys Asn Leu Pro Leu Ala Asp Gln Gly Ser Ser His His Ile Thr Val
        690                 695                 700

Lys Ile Asn Glu Leu Lys Ser Val Gln Asn Asp Ser Gln Ala Ile Ala
705                 710                 715                 720

Glu Val Leu Asn Gln Leu Lys Asp Met Leu Ala Asn Phe Arg Gly Ser
                725                 730                 735

Glu Lys Tyr Cys Tyr Leu Gln Asn Glu Val Phe Gly Leu Phe Gln Lys
            740                 745                 750

Leu Glu Asn Ile Asn Gly Val Thr Asp Gly Tyr Leu Asn Ser Leu Cys
        755                 760                 765

Thr Val Arg Ala Leu Leu Gln Ala Ile Leu Gln Thr Glu Asp Met Leu
        770                 775                 780

Lys Val Tyr Glu Ala Arg Leu Thr Glu Glu Thr Val Cys Leu Asp
785                 790                 795                 800

Leu Asp Lys Val Glu Ala Tyr Arg Cys Gly Leu Lys Lys Ile Lys Asn
                805                 810                 815

Asp Leu Asn Leu Lys Lys Ser Leu Leu Ala Thr Met Lys Thr Glu Leu
            820                 825                 830

Gln Lys Ala Gln Gln Ile His Ser Gln Thr Ser Gln Gln Tyr Pro Leu
        835                 840                 845

Tyr Asp Leu Asp Leu Gly Lys Phe Gly Glu Lys Val Thr Gln Leu Thr
850                 855                 860

Asp Arg Trp Gln Arg Ile Asp Lys Gln Ile Asp Phe Arg Leu Trp Asp
865                 870                 875                 880

Leu Glu Lys Gln Ile Lys Gln Leu Arg Asn Tyr Arg Asp Asn Tyr Gln
                885                 890                 895

Ala Phe Cys Lys Trp Leu Tyr Asp Ala Lys Arg Arg Gly Asp Ser Leu
            900                 905                 910

Glu Ser Met Lys Phe Gly Asp Ser Asn Thr Val Met Arg Phe Leu Asn
        915                 920                 925

Glu Gln Lys Asn Leu His Ser Glu Ile Ser Gly Lys Arg Asp Lys Ser
        930                 935                 940

Glu Glu Val Gln Lys Ile Ala Glu Leu Cys Ala Asn Ser Ile Lys Asp
945                 950                 955                 960

Tyr Glu Leu Gln Leu Ala Ser Tyr Thr Ser Gly Leu Glu Thr Leu Leu
                965                 970                 975

Asn Ile Pro Ile Lys Arg Thr Met Ile Gln Ser Pro Ser Gly Val Ile
            980                 985                 990
```

```
Leu Gln Glu Ala Ala Asp Val His  Ala Arg Tyr Ile Glu  Leu Leu Thr
        995              1000                  1005

Arg Ser  Gly Asp Tyr Tyr Arg  Phe Leu Ser Glu Met  Leu Lys Ser
    1010              1015                1020

Leu Glu  Asp Leu Lys Leu Lys  Asn Thr Lys Ile Glu  Val Leu Glu
    1025              1030                1035

Glu Glu  Leu Arg Leu Ala Arg  Asp Ala Asn Ser Glu  Asn Cys Asn
    1040              1045                1050

Lys Asn  Lys Phe Leu Asp Gln  Asn Leu Gln Lys Tyr  Gln Ala Glu
    1055              1060                1065

Cys Ser  Gln Phe Lys Ala Lys  Leu Ala Ser Leu Glu  Glu Leu Lys
    1070              1075                1080

Arg Gln  Ala Glu Leu Asp Gly  Lys Ser Ala Lys Gln  Asn Leu Asp
    1085              1090                1095

Lys Cys  Tyr Gly Gln Ile Lys  Glu Leu Asn Glu Lys  Ile Thr Arg
    1100              1105                1110

Leu Thr  Tyr Glu Ile Glu Asp  Glu Lys Arg Arg Arg  Lys Ser Val
    1115              1120                1125

Glu Asp  Arg Phe Asp Gln Gln  Lys Asn Asp Tyr Asp  Gln Leu Gln
    1130              1135                1140

Lys Ala  Arg Gln Cys Glu Lys  Glu Asn Leu Gly Trp  Gln Lys Leu
    1145              1150                1155

Glu Ser  Glu Lys Ala Ile Lys  Glu Lys Glu Tyr Glu  Ile Glu Arg
    1160              1165                1170

Leu Arg  Val Leu Leu Gln Glu  Glu Gly Thr Arg Lys  Arg Glu Tyr
    1175              1180                1185

Glu Asn  Glu Leu Ala Lys Val  Arg Asn His Tyr Asn  Glu Glu Met
    1190              1195                1200

Ser Asn  Leu Arg Asn Lys Tyr  Glu Thr Glu Ile Asn  Ile Thr Lys
    1205              1210                1215

Thr Thr  Ile Lys Glu Ile Ser  Met Gln Lys Glu Asp  Asp Ser Lys
    1220              1225                1230

Asn Leu  Arg Asn Gln Leu Asp  Arg Leu Ser Arg Glu  Asn Arg Asp
    1235              1240                1245

Leu Lys  Asp Glu Ile Val Arg  Leu Asn Asp Ser Ile  Leu Gln Ala
    1250              1255                1260

Thr Glu  Gln Arg Arg Arg Ala  Glu Glu Asn Ala Leu  Gln Gln Lys
    1265              1270                1275

Ala Cys  Gly Ser Glu Ile Met  Gln Lys Lys Gln His  Leu Glu Ile
    1280              1285                1290

Glu Leu  Lys Gln Val Met Gln  Gln Arg Ser Glu Asp  Asn Ala Arg
    1295              1300                1305

His Lys  Gln Ser Leu Glu Glu  Ala Ala Lys Thr Ile  Gln Asp Lys
    1310              1315                1320

Asn Lys  Glu Ile Glu Arg Leu  Lys Ala Glu Phe Gln  Glu Glu Ala
    1325              1330                1335

Lys Arg  Arg Trp Glu Tyr Glu  Asn Glu Leu Ser Lys  Val Arg Asn
    1340              1345                1350

Asn Tyr  Asp Glu Glu Ile Ile  Ser Leu Lys Asn Gln  Phe Glu Thr
    1355              1360                1365

Glu Ile  Asn Ile Thr Lys Thr  Thr Ile His Gln Leu  Thr Met Gln
    1370              1375                1380

Lys Glu  Glu Asp Thr Ser Gly  Tyr Arg Ala Gln Ile  Asp Asn Leu
```

```
            1385                1390                1395

Thr Arg Glu Asn Arg Ser Leu Ser Glu Glu Ile Lys Arg Leu Lys
    1400                1405                1410

Asn Thr Leu Thr Gln Thr Thr Glu Asn Leu Arg Arg Val Glu Glu
    1415                1420                1425

Asp Ile Gln Gln Gln Lys Ala Thr Gly Ser Glu Val Ser Gln Arg
    1430                1435                1440

Lys Gln Gln Leu Glu Val Glu Leu Arg Gln Val Thr Gln Met Arg
    1445                1450                1455

Thr Glu Glu Ser Val Arg Tyr Lys Gln Ser Leu Asp Asp Ala Ala
    1460                1465                1470

Lys Thr Ile Gln Asp Lys Asn Lys Glu Ile Glu Arg Leu Lys Gln
    1475                1480                1485

Leu Ile Asp Lys Glu Thr Asn Asp Arg Lys Cys Leu Glu Asp Glu
    1490                1495                1500

Asn Ala Arg Leu Gln Arg Val Gln Tyr Asp Leu Gln Lys Ala Asn
    1505                1510                1515

Ser Ser Ala Thr Glu Thr Ile Asn Lys Leu Lys Val Gln Glu Gln
    1520                1525                1530

Glu Leu Thr Arg Leu Arg Ile Asp Tyr Glu Arg Val Ser Gln Glu
    1535                1540                1545

Arg Thr Val Lys Asp Gln Asp Ile Thr Arg Phe Gln Asn Ser Leu
    1550                1555                1560

Lys Glu Leu Gln Leu Gln Lys Gln Lys Val Glu Glu Glu Leu Asn
    1565                1570                1575

Arg Leu Lys Arg Thr Ala Ser Glu Asp Ser Cys Lys Arg Lys Lys
    1580                1585                1590

Leu Glu Glu Glu Leu Glu Gly Met Arg Arg Ser Leu Lys Glu Gln
    1595                1600                1605

Ala Ile Lys Ile Thr Asn Leu Thr Gln Gln Leu Glu Gln Ala Ser
    1610                1615                1620

Ile Val Lys Lys Arg Ser Glu Asp Asp Leu Arg Gln Gln Arg Asp
    1625                1630                1635

Val Leu Asp Gly His Leu Arg Glu Lys Gln Arg Thr Gln Glu Glu
    1640                1645                1650

Leu Arg Arg Leu Ser Ser Glu Val Glu Ala Leu Arg Arg Gln Leu
    1655                1660                1665

Leu Gln Glu Gln Glu Ser Val Lys Gln Ala His Leu Arg Asn Glu
    1670                1675                1680

His Phe Gln Lys Ala Ile Glu Asp Lys Ser Arg Ser Leu Asn Glu
    1685                1690                1695

Ser Lys Ile Glu Ile Glu Arg Leu Gln Ser Leu Thr Glu Asn Leu
    1700                1705                1710

Thr Lys Glu His Leu Met Leu Glu Glu Glu Leu Arg Asn Leu Arg
    1715                1720                1725

Leu Glu Tyr Asp Asp Leu Arg Arg Gly Arg Ser Glu Ala Asp Ser
    1730                1735                1740

Asp Lys Asn Ala Thr Ile Leu Glu Leu Arg Ser Gln Leu Gln Ile
    1745                1750                1755

Ser Asn Asn Arg Thr Leu Glu Leu Gln Gly Leu Ile Asn Asp Leu
    1760                1765                1770

Gln Arg Glu Arg Glu Asn Leu Arg Gln Glu Ile Glu Lys Phe Gln
    1775                1780                1785
```

-continued

```
Lys Gln Ala Leu Glu Ala Ser Asn Arg Ile Gln Glu Ser Lys Asn
1790                1795                1800

Gln Cys Thr Gln Val Val Gln Glu Arg Glu Ser Leu Leu Val Lys
1805                1810                1815

Ile Lys Val Leu Glu Gln Asp Lys Ala Arg Leu Gln Arg Leu Glu
1820                1825                1830

Asp Glu Leu Asn Arg Ala Lys Ser Thr Leu Glu Ala Glu Thr Arg
1835                1840                1845

Val Lys Gln Arg Leu Glu Cys Glu Lys Gln Gln Ile Gln Asn Asp
1850                1855                1860

Leu Asn Gln Trp Lys Thr Gln Tyr Ser Arg Lys Glu Glu Ala Ile
1865                1870                1875

Arg Lys Ile Glu Ser Glu Arg Glu Lys Ser Glu Arg Glu Lys Asn
1880                1885                1890

Ser Leu Arg Ser Glu Ile Glu Arg Leu Gln Ala Glu Ile Lys Arg
1895                1900                1905

Ile Glu Glu Arg Cys Arg Arg Lys Leu Glu Asp Ser Thr Arg Glu
1910                1915                1920

Thr Gln Ser Gln Leu Glu Thr Glu Arg Ser Arg Tyr Gln Arg Glu
1925                1930                1935

Ile Asp Lys Leu Arg Gln Arg Pro Tyr Gly Ser His Arg Glu Thr
1940                1945                1950

Gln Thr Glu Cys Glu Trp Thr Val Asp Thr Ser Lys Leu Val Phe
1955                1960                1965

Asp Gly Leu Arg Lys Lys Val Thr Ala Met Gln Leu Tyr Glu Cys
1970                1975                1980

Gln Leu Ile Asp Lys Thr Thr Leu Asp Lys Leu Leu Lys Gly Lys
1985                1990                1995

Lys Ser Val Glu Glu Val Ala Ser Glu Ile Gln Pro Phe Leu Arg
2000                2005                2010

Gly Ala Gly Ser Ile Ala Gly Ala Ser Ala Ser Pro Lys Glu Lys
2015                2020                2025

Tyr Ser Leu Val Glu Ala Lys Arg Lys Lys Leu Ile Ser Pro Glu
2030                2035                2040

Ser Thr Val Met Leu Leu Glu Ala Gln Ala Ala Thr Gly Gly Ile
2045                2050                2055

Ile Asp Pro His Arg Asn Glu Lys Leu Thr Val Asp Ser Ala Ile
2060                2065                2070

Ala Arg Asp Leu Ile Asp Phe Asp Asp Arg Gln Gln Ile Tyr Ala
2075                2080                2085

Ala Glu Lys Ala Ile Thr Gly Phe Asp Asp Pro Phe Ser Gly Lys
2090                2095                2100

Thr Val Ser Val Ser Glu Ala Ile Lys Lys Asn Leu Ile Asp Arg
2105                2110                2115

Glu Thr Gly Met Arg Leu Leu Glu Ala Gln Ile Ala Ser Gly Gly
2120                2125                2130

Val Val Asp Pro Val Asn Ser Val Phe Leu Pro Lys Asp Val Ala
2135                2140                2145

Leu Ala Arg Gly Leu Ile Asp Arg Asp Leu Tyr Arg Ser Leu Asn
2150                2155                2160

Asp Pro Arg Asp Ser Gln Lys Asn Phe Val Asp Pro Val Thr Lys
2165                2170                2175
```

```
Lys Lys Val Ser Tyr Val Gln Leu Lys Glu Arg Cys Arg Ile Glu
2180             2185                 2190

Pro His Thr Gly Leu Leu Leu Ser Val Gln Lys Arg Ser Met
2195             2200                 2205

Ser Phe Gln Gly Ile Arg Gln Pro Val Thr Val Thr Glu Leu Val
2210             2215                 2220

Asp Ser Gly Ile Leu Arg Pro Ser Thr Val Asn Glu Leu Glu Ser
2225             2230                 2235

Gly Gln Ile Ser Tyr Asp Glu Val Gly Glu Arg Ile Lys Asp Phe
2240             2245                 2250

Leu Gln Gly Ser Ser Cys Ile Ala Gly Ile Tyr Asn Glu Thr Thr
2255             2260                 2265

Lys Gln Lys Leu Gly Ile Tyr Glu Ala Met Lys Ile Gly Leu Val
2270             2275                 2280

Arg Pro Gly Thr Ala Leu Glu Leu Leu Glu Ala Gln Ala Ala Thr
2285             2290                 2295

Gly Phe Ile Val Asp Pro Val Ser Asn Leu Arg Leu Pro Val Glu
2300             2305                 2310

Glu Ala Tyr Lys Arg Gly Leu Val Gly Ile Glu Phe Lys Glu Lys
2315             2320                 2325

Leu Leu Ser Ala Glu Arg Ala Val Thr Gly Tyr Asn Asp Pro Glu
2330             2335                 2340

Thr Gly Asn Ile Ile Ser Leu Phe Gln Ala Met Asn Lys Glu Leu
2345             2350                 2355

Ile Glu Lys Gly His Gly Ile Arg Leu Leu Glu Ala Gln Ile Ala
2360             2365                 2370

Thr Gly Gly Ile Ile Asp Pro Lys Glu Ser His Arg Leu Pro Val
2375             2380                 2385

Asp Ile Ala Tyr Lys Arg Gly Tyr Phe Asn Glu Glu Leu Ser Glu
2390             2395                 2400

Ile Leu Ser Asp Pro Ser Asp Asp Thr Lys Gly Phe Phe Asp Pro
2405             2410                 2415

Asn Thr Glu Glu Asn Leu Thr Tyr Leu Gln Leu Lys Glu Arg Cys
2420             2425                 2430

Ile Lys Asp Glu Glu Thr Gly Leu Cys Leu Leu Pro Leu Lys Glu
2435             2440                 2445

Lys Lys Lys Gln Val Gln Thr Ser Gln Lys Asn Thr Leu Arg Lys
2450             2455                 2460

Arg Arg Val Val Ile Val Asp Pro Glu Thr Asn Lys Glu Met Ser
2465             2470                 2475

Val Gln Glu Ala Tyr Lys Lys Gly Leu Ile Asp Tyr Glu Thr Phe
2480             2485                 2490

Lys Glu Leu Cys Glu Gln Glu Cys Glu Trp Glu Glu Ile Thr Ile
2495             2500                 2505

Thr Gly Ser Asp Gly Ser Thr Arg Val Val Leu Val Asp Arg Lys
2510             2515                 2520

Thr Gly Ser Gln Tyr Asp Ile Gln Asp Ala Ile Asp Lys Gly Leu
2525             2530                 2535

Val Asp Arg Lys Phe Phe Asp Gln Tyr Arg Ser Gly Ser Leu Ser
2540             2545                 2550

Leu Thr Gln Phe Ala Asp Met Ile Ser Leu Lys Asn Gly Val Gly
2555             2560                 2565

Thr Ser Ser Ser Met Gly Ser Gly Val Ser Asp Asp Val Phe Ser
```

2570                2575                2580

Ser  Ser  Arg  His  Glu  Ser  Val  Ser  Lys  Ile  Ser  Thr  Ile  Ser  Ser
     2585                2590                2595

Val  Arg  Asn  Leu  Thr  Ile  Arg  Ser  Ser  Ser  Phe  Ser  Asp  Thr  Leu
2600                2605                2610

Glu  Glu  Ser  Ser  Pro  Ile  Ala  Ala  Ile  Phe  Asp  Thr  Glu  Asn  Leu
2615                2620                2625

Glu  Lys  Ile  Ser  Ile  Thr  Glu  Gly  Ile  Glu  Arg  Gly  Ile  Val  Asp
2630                2635                2640

Ser  Ile  Thr  Gly  Gln  Arg  Leu  Leu  Glu  Ala  Gln  Ala  Cys  Thr  Gly
2645                2650                2655

Gly  Ile  Ile  His  Pro  Thr  Thr  Gly  Gln  Lys  Leu  Ser  Leu  Gln  Asp
2660                2665                2670

Ala  Val  Ser  Gln  Gly  Val  Ile  Asp  Gln  Asp  Met  Ala  Thr  Arg  Leu
2675                2680                2685

Lys  Pro  Ala  Gln  Lys  Ala  Phe  Ile  Gly  Phe  Glu  Gly  Val  Lys  Gly
2690                2695                2700

Lys  Lys  Lys  Met  Ser  Ala  Ala  Glu  Ala  Val  Lys  Glu  Lys  Trp  Leu
2705                2710                2715

Pro  Tyr  Glu  Ala  Gly  Gln  Arg  Phe  Leu  Glu  Phe  Gln  Tyr  Leu  Thr
2720                2725                2730

Gly  Gly  Leu  Val  Asp  Pro  Glu  Val  His  Gly  Arg  Ile  Ser  Thr  Glu
2735                2740                2745

Glu  Ala  Ile  Arg  Lys  Gly  Phe  Ile  Asp  Gly  Arg  Ala  Ala  Gln  Arg
2750                2755                2760

Leu  Gln  Asp  Thr  Ser  Ser  Tyr  Ala  Lys  Ile  Leu  Thr  Cys  Pro  Lys
2765                2770                2775

Thr  Lys  Leu  Lys  Ile  Ser  Tyr  Lys  Asp  Ala  Ile  Asn  Arg  Ser  Met
2780                2785                2790

Val  Glu  Asp  Ile  Thr  Gly  Leu  Arg  Leu  Leu  Glu  Ala  Ala  Ser  Val
2795                2800                2805

Ser  Ser  Lys  Gly  Leu  Pro  Ser  Pro  Tyr  Asn  Met  Ser  Ser  Ala  Pro
2810                2815                2820

Gly  Ser  Arg  Ser  Gly  Ser  Arg  Ser  Gly  Ser  Arg  Ser  Gly  Ser  Arg
2825                2830                2835

Ser  Gly  Ser  Arg  Ser  Gly  Ser  Arg  Arg  Gly  Ser  Phe  Asp  Ala  Thr
2840                2845                2850

Gly  Asn  Ser  Ser  Tyr  Ser  Tyr  Ser  Tyr  Ser  Phe  Ser  Ser  Ser  Ser
2855                2860                2865

Ile  Gly  His
2870

<210> SEQ ID NO 4
<211> LENGTH: 2272
<212> TYPE: PRT
<213> ORGANISM: homo sapiens
<220> FEATURE:
<221> NAME/KEY: MISC_FEATURE
<223> OTHER INFORMATION: amino acid sequence of Desmoplakin isoform 2

<400> SEQUENCE: 4

Met  Ser  Cys  Asn  Gly  Gly  Ser  His  Pro  Arg  Ile  Asn  Thr  Leu  Gly
1                 5                   10                  15

Met  Ile  Arg  Ala  Glu  Ser  Gly  Pro  Asp  Leu  Arg  Tyr  Glu  Val  Thr  Ser
            20                  25                  30

-continued

```
Gly Gly Gly Gly Thr Ser Arg Met Tyr Tyr Ser Arg Gly Val Ile
            35                  40                  45

Thr Asp Gln Asn Ser Asp Gly Tyr Cys Gln Thr Gly Thr Met Ser Arg
 50                  55                  60

His Gln Asn Gln Asn Thr Ile Gln Glu Leu Leu Gln Asn Cys Ser Asp
 65                  70                  75                  80

Cys Leu Met Arg Ala Glu Leu Ile Val Gln Pro Glu Leu Lys Tyr Gly
                 85                  90                  95

Asp Gly Ile Gln Leu Thr Arg Ser Arg Glu Leu Asp Glu Cys Phe Ala
            100                 105                 110

Gln Ala Asn Asp Gln Met Glu Ile Leu Asp Ser Leu Ile Arg Glu Met
            115                 120                 125

Arg Gln Met Gly Gln Pro Cys Asp Ala Tyr Gln Lys Arg Leu Leu Gln
130                 135                 140

Leu Gln Glu Gln Met Arg Ala Leu Tyr Lys Ala Ile Ser Val Pro Arg
145                 150                 155                 160

Val Arg Arg Ala Ser Ser Lys Gly Gly Gly Tyr Thr Cys Gln Ser
                165                 170                 175

Gly Ser Gly Trp Asp Glu Phe Thr Lys His Val Thr Ser Glu Cys Leu
            180                 185                 190

Gly Trp Met Arg Gln Gln Arg Ala Glu Met Asp Met Val Ala Trp Gly
            195                 200                 205

Val Asp Leu Ala Ser Val Glu Gln His Ile Asn Ser His Arg Gly Ile
210                 215                 220

His Asn Ser Ile Gly Asp Tyr Arg Trp Gln Leu Asp Lys Ile Lys Ala
225                 230                 235                 240

Asp Leu Arg Glu Lys Ser Ala Ile Tyr Gln Leu Glu Glu Tyr Glu
                245                 250                 255

Asn Leu Leu Lys Ala Ser Phe Glu Arg Met Asp His Leu Arg Gln Leu
            260                 265                 270

Gln Asn Ile Ile Gln Ala Thr Ser Arg Glu Ile Met Trp Ile Asn Asp
            275                 280                 285

Cys Glu Glu Glu Leu Leu Tyr Asp Trp Ser Asp Lys Asn Thr Asn
290                 295                 300

Ile Ala Gln Lys Gln Glu Ala Phe Ser Ile Arg Met Ser Gln Leu Glu
305                 310                 315                 320

Val Lys Glu Lys Glu Leu Asn Lys Leu Lys Gln Glu Ser Asp Gln Leu
                325                 330                 335

Val Leu Asn Gln His Pro Ala Ser Asp Lys Ile Glu Ala Tyr Met Asp
            340                 345                 350

Thr Leu Gln Thr Gln Trp Ser Trp Ile Leu Gln Ile Thr Lys Cys Ile
            355                 360                 365

Asp Val His Leu Lys Glu Asn Ala Ala Tyr Phe Gln Phe Phe Glu Glu
370                 375                 380

Ala Gln Ser Thr Glu Ala Tyr Leu Lys Gly Leu Gln Asp Ser Ile Arg
385                 390                 395                 400

Lys Lys Tyr Pro Cys Asp Lys Asn Met Pro Leu Gln His Leu Leu Glu
                405                 410                 415

Gln Ile Lys Glu Leu Glu Lys Glu Arg Glu Lys Ile Leu Glu Tyr Lys
            420                 425                 430

Arg Gln Val Gln Asn Leu Val Asn Lys Ser Lys Ile Val Gln Leu
435                 440                 445

Lys Pro Arg Asn Pro Asp Tyr Arg Ser Asn Lys Pro Ile Ile Leu Arg
```

```
                450             455             460
Ala Leu Cys Asp Tyr Lys Gln Asp Gln Lys Ile Val His Lys Gly Asp
465                 470                 475                 480

Glu Cys Ile Leu Lys Asp Asn Asn Glu Arg Ser Lys Trp Tyr Val Thr
                485                 490                 495

Gly Pro Gly Gly Val Asp Met Leu Val Pro Ser Val Gly Leu Ile Ile
                500                 505                 510

Pro Pro Pro Asn Pro Leu Ala Val Asp Leu Ser Cys Lys Ile Glu Gln
            515                 520                 525

Tyr Tyr Glu Ala Ile Leu Ala Leu Trp Asn Gln Leu Tyr Ile Asn Met
        530                 535                 540

Lys Ser Leu Val Ser Trp His Tyr Cys Met Ile Asp Ile Glu Lys Ile
545                 550                 555                 560

Arg Ala Met Thr Ile Ala Lys Leu Lys Thr Met Arg Gln Glu Asp Tyr
                565                 570                 575

Met Lys Thr Ile Ala Asp Leu Glu Leu His Tyr Gln Glu Phe Ile Arg
                580                 585                 590

Asn Ser Gln Gly Ser Glu Met Phe Gly Asp Asp Lys Arg Lys Ile
            595                 600                 605

Gln Ser Gln Phe Thr Asp Ala Gln Lys His Tyr Gln Thr Leu Val Ile
    610                 615                 620

Gln Leu Pro Gly Tyr Pro Gln His Gln Thr Val Thr Thr Thr Glu Ile
625                 630                 635                 640

Thr His His Gly Thr Cys Gln Asp Val Asn His Asn Lys Val Ile Glu
                645                 650                 655

Thr Asn Arg Glu Asn Asp Lys Gln Glu Thr Trp Met Leu Met Glu Leu
                660                 665                 670

Gln Lys Ile Arg Arg Gln Ile Glu His Cys Glu Gly Arg Met Thr Leu
                675                 680                 685

Lys Asn Leu Pro Leu Ala Asp Gln Gly Ser Ser His His Ile Thr Val
690                 695                 700

Lys Ile Asn Glu Leu Lys Ser Val Gln Asn Asp Ser Gln Ala Ile Ala
705                 710                 715                 720

Glu Val Leu Asn Gln Leu Lys Asp Met Leu Ala Asn Phe Arg Gly Ser
                725                 730                 735

Glu Lys Tyr Cys Tyr Leu Gln Asn Glu Val Phe Gly Leu Phe Gln Lys
            740                 745                 750

Leu Glu Asn Ile Asn Gly Val Thr Asp Gly Tyr Leu Asn Ser Leu Cys
        755                 760                 765

Thr Val Arg Ala Leu Leu Gln Ala Ile Leu Gln Thr Glu Asp Met Leu
770                 775                 780

Lys Val Tyr Glu Ala Arg Leu Thr Glu Glu Thr Val Cys Leu Asp
785                 790                 795                 800

Leu Asp Lys Val Glu Ala Tyr Arg Cys Gly Leu Lys Lys Ile Lys Asn
                805                 810                 815

Asp Leu Asn Leu Lys Lys Ser Leu Leu Ala Thr Met Lys Thr Glu Leu
            820                 825                 830

Gln Lys Ala Gln Gln Ile His Ser Gln Thr Ser Gln Gln Tyr Pro Leu
            835                 840                 845

Tyr Asp Leu Asp Leu Gly Lys Phe Gly Glu Lys Val Thr Gln Leu Thr
        850                 855                 860

Asp Arg Trp Gln Arg Ile Asp Lys Gln Ile Asp Phe Arg Leu Trp Asp
865                 870                 875                 880
```

-continued

Leu Glu Lys Gln Ile Lys Gln Leu Arg Asn Tyr Arg Asp Asn Tyr Gln
             885                 890                 895

Ala Phe Cys Lys Trp Leu Tyr Asp Ala Lys Arg Arg Gln Asp Ser Leu
             900                 905                 910

Glu Ser Met Lys Phe Gly Asp Ser Asn Thr Val Met Arg Phe Leu Asn
             915                 920                 925

Glu Gln Lys Asn Leu His Ser Glu Ile Ser Gly Lys Arg Asp Lys Ser
        930                 935                 940

Glu Glu Val Gln Lys Ile Ala Glu Leu Cys Ala Asn Ser Ile Lys Asp
945                 950                 955                 960

Tyr Glu Leu Gln Leu Ala Ser Tyr Thr Ser Gly Leu Glu Thr Leu Leu
             965                 970                 975

Asn Ile Pro Ile Lys Arg Thr Met Ile Gln Ser Pro Ser Gly Val Ile
             980                 985                 990

Leu Gln Glu Ala Ala Asp Val His Ala Arg Tyr Ile Glu Leu Leu Thr
             995                1000                1005

Arg Ser Gly Asp Tyr Tyr Arg Phe Leu Ser Glu Met Leu Lys Ser
        1010                1015                1020

Leu Glu Asp Leu Lys Leu Lys Asn Thr Lys Ile Glu Val Leu Glu
        1025                1030                1035

Glu Glu Leu Arg Leu Ala Arg Asp Ala Asn Ser Glu Asn Cys Asn
        1040                1045                1050

Lys Asn Lys Phe Leu Asp Gln Asn Leu Gln Lys Tyr Gln Ala Glu
        1055                1060                1065

Cys Ser Gln Phe Lys Ala Lys Leu Ala Ser Leu Glu Glu Leu Lys
        1070                1075                1080

Arg Gln Ala Glu Leu Asp Gly Lys Ser Ala Lys Gln Asn Leu Asp
        1085                1090                1095

Lys Cys Tyr Gly Gln Ile Lys Glu Leu Asn Glu Lys Ile Thr Arg
        1100                1105                1110

Leu Thr Tyr Glu Ile Glu Asp Glu Lys Arg Arg Arg Lys Ser Val
        1115                1120                1125

Glu Asp Arg Phe Asp Gln Gln Lys Asn Asp Tyr Asp Gln Leu Gln
        1130                1135                1140

Lys Ala Arg Gln Cys Glu Lys Glu Asn Leu Gly Trp Gln Lys Leu
        1145                1150                1155

Glu Ser Glu Lys Ala Ile Lys Glu Lys Glu Tyr Glu Ile Glu Arg
        1160                1165                1170

Leu Arg Val Leu Leu Gln Glu Glu Gly Thr Arg Lys Arg Glu Tyr
        1175                1180                1185

Glu Asn Glu Leu Ala Lys Ala Ser Asn Arg Ile Gln Glu Ser Lys
        1190                1195                1200

Asn Gln Cys Thr Gln Val Val Gln Glu Arg Glu Ser Leu Leu Val
        1205                1210                1215

Lys Ile Lys Val Leu Glu Gln Asp Lys Ala Arg Leu Gln Arg Leu
        1220                1225                1230

Glu Asp Glu Leu Asn Arg Ala Lys Ser Thr Leu Glu Ala Glu Thr
        1235                1240                1245

Arg Val Lys Gln Arg Leu Glu Cys Glu Lys Gln Gln Ile Gln Asn
        1250                1255                1260

Asp Leu Asn Gln Trp Lys Thr Gln Tyr Ser Arg Lys Glu Glu Ala
        1265                1270                1275

-continued

```
Ile Arg Lys Ile Glu Ser Glu Arg Glu Lys Ser Glu Arg Glu Lys
    1280                1285                1290
Asn Ser Leu Arg Ser Glu Ile Glu Arg Leu Gln Ala Glu Ile Lys
    1295                1300                1305
Arg Ile Glu Glu Arg Cys Arg Arg Lys Leu Glu Asp Ser Thr Arg
    1310                1315                1320
Glu Thr Gln Ser Gln Leu Glu Thr Glu Arg Ser Arg Tyr Gln Arg
    1325                1330                1335
Glu Ile Asp Lys Leu Arg Gln Arg Pro Tyr Gly Ser His Arg Glu
    1340                1345                1350
Thr Gln Thr Glu Cys Glu Trp Thr Val Asp Thr Ser Lys Leu Val
    1355                1360                1365
Phe Asp Gly Leu Arg Lys Lys Val Thr Ala Met Gln Leu Tyr Glu
    1370                1375                1380
Cys Gln Leu Ile Asp Lys Thr Thr Leu Asp Lys Leu Leu Lys Gly
    1385                1390                1395
Lys Lys Ser Val Glu Glu Val Ala Ser Glu Ile Gln Pro Phe Leu
    1400                1405                1410
Arg Gly Ala Gly Ser Ile Ala Gly Ala Ser Ala Ser Pro Lys Glu
    1415                1420                1425
Lys Tyr Ser Leu Val Glu Ala Lys Arg Lys Lys Leu Ile Ser Pro
    1430                1435                1440
Glu Ser Thr Val Met Leu Leu Glu Ala Gln Ala Ala Thr Gly Gly
    1445                1450                1455
Ile Ile Asp Pro His Arg Asn Glu Lys Leu Thr Val Asp Ser Ala
    1460                1465                1470
Ile Ala Arg Asp Leu Ile Asp Phe Asp Asp Arg Gln Gln Ile Tyr
    1475                1480                1485
Ala Ala Glu Lys Ala Ile Thr Gly Phe Asp Asp Pro Phe Ser Gly
    1490                1495                1500
Lys Thr Val Ser Val Ser Glu Ala Ile Lys Lys Asn Leu Ile Asp
    1505                1510                1515
Arg Glu Thr Gly Met Arg Leu Leu Glu Ala Gln Ile Ala Ser Gly
    1520                1525                1530
Gly Val Val Asp Pro Val Asn Ser Val Phe Leu Pro Lys Asp Val
    1535                1540                1545
Ala Leu Ala Arg Gly Leu Ile Asp Arg Asp Leu Tyr Arg Ser Leu
    1550                1555                1560
Asn Asp Pro Arg Asp Ser Gln Lys Asn Phe Val Asp Pro Val Thr
    1565                1570                1575
Lys Lys Lys Val Ser Tyr Val Gln Leu Lys Glu Arg Cys Arg Ile
    1580                1585                1590
Glu Pro His Thr Gly Leu Leu Leu Ser Val Gln Lys Arg Ser
    1595                1600                1605
Met Ser Phe Gln Gly Ile Arg Gln Pro Val Thr Val Thr Glu Leu
    1610                1615                1620
Val Asp Ser Gly Ile Leu Arg Pro Ser Thr Val Asn Glu Leu Glu
    1625                1630                1635
Ser Gly Gln Ile Ser Tyr Asp Glu Val Gly Glu Arg Ile Lys Asp
    1640                1645                1650
Phe Leu Gln Gly Ser Ser Cys Ile Ala Gly Ile Tyr Asn Glu Thr
    1655                1660                1665
Thr Lys Gln Lys Leu Gly Ile Tyr Glu Ala Met Lys Ile Gly Leu
```

-continued

```
            1670                1675                1680
Val Arg Pro Gly Thr Ala Leu Glu Leu Leu Glu Ala Gln Ala Ala
            1685                1690                1695

Thr Gly Phe Ile Val Asp Pro Val Ser Asn Leu Arg Leu Pro Val
            1700                1705                1710

Glu Glu Ala Tyr Lys Arg Gly Leu Val Gly Ile Glu Phe Lys Glu
            1715                1720                1725

Lys Leu Leu Ser Ala Glu Arg Ala Val Thr Gly Tyr Asn Asp Pro
            1730                1735                1740

Glu Thr Gly Asn Ile Ile Ser Leu Phe Gln Ala Met Asn Lys Glu
            1745                1750                1755

Leu Ile Glu Lys Gly His Gly Ile Arg Leu Leu Glu Ala Gln Ile
            1760                1765                1770

Ala Thr Gly Gly Ile Ile Asp Pro Lys Glu Ser His Arg Leu Pro
            1775                1780                1785

Val Asp Ile Ala Tyr Lys Arg Gly Tyr Phe Asn Glu Glu Leu Ser
            1790                1795                1800

Glu Ile Leu Ser Asp Pro Ser Asp Asp Thr Lys Gly Phe Phe Asp
            1805                1810                1815

Pro Asn Thr Glu Glu Asn Leu Thr Tyr Leu Gln Leu Lys Glu Arg
            1820                1825                1830

Cys Ile Lys Asp Glu Glu Thr Gly Leu Cys Leu Leu Pro Leu Lys
            1835                1840                1845

Glu Lys Lys Lys Gln Val Gln Thr Ser Gln Lys Asn Thr Leu Arg
            1850                1855                1860

Lys Arg Arg Val Val Ile Val Asp Pro Glu Thr Asn Lys Glu Met
            1865                1870                1875

Ser Val Gln Glu Ala Tyr Lys Lys Gly Leu Ile Asp Tyr Glu Thr
            1880                1885                1890

Phe Lys Glu Leu Cys Glu Gln Glu Cys Glu Trp Glu Glu Ile Thr
            1895                1900                1905

Ile Thr Gly Ser Asp Gly Ser Thr Arg Val Val Leu Val Asp Arg
            1910                1915                1920

Lys Thr Gly Ser Gln Tyr Asp Ile Gln Asp Ala Ile Asp Lys Gly
            1925                1930                1935

Leu Val Asp Arg Lys Phe Phe Asp Gln Tyr Arg Ser Gly Ser Leu
            1940                1945                1950

Ser Leu Thr Gln Phe Ala Asp Met Ile Ser Leu Lys Asn Gly Val
            1955                1960                1965

Gly Thr Ser Ser Ser Met Gly Ser Gly Val Ser Asp Asp Val Phe
            1970                1975                1980

Ser Ser Ser Arg His Glu Ser Val Ser Lys Ile Ser Thr Ile Ser
            1985                1990                1995

Ser Val Arg Asn Leu Thr Ile Arg Ser Ser Ser Phe Ser Asp Thr
            2000                2005                2010

Leu Glu Glu Ser Ser Pro Ile Ala Ala Ile Phe Asp Thr Glu Asn
            2015                2020                2025

Leu Glu Lys Ile Ser Ile Thr Glu Gly Ile Glu Arg Gly Ile Val
            2030                2035                2040

Asp Ser Ile Thr Gly Gln Arg Leu Leu Glu Ala Gln Ala Cys Thr
            2045                2050                2055

Gly Gly Ile Ile His Pro Thr Thr Gly Gln Lys Leu Ser Leu Gln
            2060                2065                2070
```

```
Asp Ala Val Ser Gln Gly Val Ile Asp Gln Asp Met Ala Thr Arg
    2075            2080            2085

Leu Lys Pro Ala Gln Lys Ala Phe Ile Gly Phe Glu Gly Val Lys
    2090            2095            2100

Gly Lys Lys Lys Met Ser Ala Ala Glu Ala Val Lys Glu Lys Trp
    2105            2110            2115

Leu Pro Tyr Glu Ala Gly Gln Arg Phe Leu Glu Phe Gln Tyr Leu
    2120            2125            2130

Thr Gly Gly Leu Val Asp Pro Glu Val His Gly Arg Ile Ser Thr
    2135            2140            2145

Glu Glu Ala Ile Arg Lys Gly Phe Ile Asp Gly Arg Ala Ala Gln
    2150            2155            2160

Arg Leu Gln Asp Thr Ser Ser Tyr Ala Lys Ile Leu Thr Cys Pro
    2165            2170            2175

Lys Thr Lys Leu Lys Ile Ser Tyr Lys Asp Ala Ile Asn Arg Ser
    2180            2185            2190

Met Val Glu Asp Ile Thr Gly Leu Arg Leu Leu Glu Ala Ala Ser
    2195            2200            2205

Val Ser Ser Lys Gly Leu Pro Ser Pro Tyr Asn Met Ser Ser Ala
    2210            2215            2220

Pro Gly Ser Arg Ser Gly Ser Arg Ser Gly Ser Arg Ser Gly Ser
    2225            2230            2235

Arg Ser Gly Ser Arg Ser Gly Ser Arg Arg Gly Ser Phe Asp Ala
    2240            2245            2250

Thr Gly Asn Ser Ser Tyr Ser Tyr Ser Tyr Ser Phe Ser Ser Ser
    2255            2260            2265

Ser Ile Gly His
    2270
```

OLFACTOMEDIN-4, NEUDESIN AND DESMOPLAKIN AS BIOMARKERS OF BREAST CANCER

RELATED APPLICATIONS

This application is a National Stage Application under 35 U.S.C. 371 of co-pending PCT application PCT/EP2014/075427 designating the U.S. and filed Nov. 24, 2014; which claims the benefit of EP application No. 13306604.3 and filed Nov. 22, 2013.

The present invention is in the technical field of breast cancer management, and more particularly relates to the diagnosis of breast cancer. The invention is more particularly based on the finding that specific biomarkers are aberrantly expressed in the blood of breast cancer patients.

With over 1.3 million cases of invasive breast cancers diagnosed annually, and more than 450,000 deaths reported per year, breast cancer is the most common malignancy diagnosed in women and one of the leading causes of cancer-related death in females.

The early detection of breast cancer is the cornerstone for reducing mortality rates in this cancer that affects one in nine women. Currently, breast cancer screening campaigns are delivered through mammography and although there is no doubt of their efficacy, this approach does have limitations in terms of sensitivity in women who have very dense breast tissue and in young women considered "at risk" (family history or genetic predisposition) for whom the regular use of ionising radiation is not recommended. Furthermore, according to recent work published in the Lancet (Independent UK Panel on Breast Cancer Screening, 2012), mammography screening leads to overdiagnosis in 19% of women. In other words, one in five diagnosis is said to be an overdiagnosis. Other imaging techniques such as sonography and nuclear magnetic resonance imaging are available, but they are not generally used for detection, being instead used as a further examination after mammography.

Besides, despite improvement in breast cancer therapies, local, contralateral breast or distant recurrence (also known as metastasis) occurs in 10 to 20% of patients in the three to ten years following initial adjuvant treatment. However, such recurrence is often either missed or identified as false positive by mammography, and unnecessary biopsies are performed on patients suspected of relapse.

It has thus become critical to identify reliable biomarkers allowing, without routine recourse to imaging techniques or invasive biopsies, not only the early detection of a breast tumour but also the monitoring of cancer progression.

Alongside imaging techniques, a great deal of work examining the expression of genes or proteins in breast tumour tissue has been carried out, but the number of biomarkers that could potentially be used for reliably detecting breast cancer was very limited, mainly because they lacked sensitivity in the clinical context. In this regard, the serum biomarkers prostate-specific antigen (PSA), CA 15-3, and carcinoembryonic antigen (CEA), which have demonstrated some value in the diagnosis and treatment of other cancers, didn't prove to be useful in the detection and monitoring of breast cancer as they lacked the desired sensitivity and specificity.

There is thus an urgent need to identify breast cancer biomarkers that are easily detectable, sensitive enough to detect the presence of a tumour in breast cancer patients, and specific enough to not detect such tumour in those who do not have cancer.

The above discussed needs are addressed by the present invention, which reports herein the results of an investigation conducted by comparative proteome mapping of breast tumours and by validation of dysregulated secreted proteomic biomarkers on a large cohort of breast cancer patients. By contrast to genomic biomarkers, proteomic biomarkers are indeed particularly advantageous as they are more reflective of a tumour microenvironment and can undergo cancer specific posttranslational modifications.

In particular, the inventors have demonstrated that dysregulation in protein expression level of Olfactomedin-4 (OLFM4), Neudesin (NENF) and/or Desmoplakin (DSP) correlates with breast cancer, and that such biomarkers are detectable in blood samples of patients. It has notably been discovered that the expression level of Olfactomedin-4 and Neudesin are higher in breast cancer patients throughout progression of the disease, while the expression level of Desmoplakin is lower at an early stage and higher in the case of recurrence, by comparison to healthy subjects.

Olfactomedin-4 is a secreted N-glycosylated protein belonging to the olfactomedin domain-containing protein family, which is characterized by a coil-coil domain N-terminal domain and a well-conserved C-terminal olfactomedin domain. The OFLM4 protein has been described in the literature as mediating cell adhesion through binding to cadherins and lectins (Liu et al., 2006), and as being involved in the regulation of cellular apoptosis and in the proliferation of cancer cells (Zhang et al., 2004; Kobayashi et al., 2007).

Neudesin on the other hand is an extracellular heme-binding protein which has been described as displaying neurotrophic activity in neurons via the mitogen-activated protein kinase (MAPK) and phosphatidylinositol 3-kinase (PI3K) pathways (Kimura et al., 2013).

Desmoplakin is a founding member of the plakin family, and is known as the principal plaque protein of desmosomes (Leung et al., 2002). It is therefore specialized in adhesion junctions found in various tissues and plays a critical role in the maintenance of epithelial tissue integrity. Recently, studies suggested that desmosomes participate in the regulation of cell motility, growth, differentiation and apoptosis (Allen et al., 1996; Wan et al., 2007; and Rickelt et al., 2009). Two isoforms of Desmoplakin have been reported so far, Desmoplakin I (322 kDa) and Desmoplakin II (259 kDa), both encoded by the Desmoplakin gene on human chromosome 6p24.3. Desmoplakin proteins interact with plakoglobin (γ-catenin), plakophilins and intermediate filaments, providing the intimate link between desmosomal cadherins and the cytoskeleton (Junkman et al., 2005; and Kowalczyk et al., 1997).

The above biomarkers can be used herein to detect breast cancer, from a mere blood sample, to monitor disease progression, to assess response to breast cancer treatment, but also to develop and adapt a breast cancer treatment. They can also be used as therapeutic targets to design novel drugs.

Therefore, based on the findings disclosed herein, the present invention provides for the first time a reliable and easy to perform diagnostic method for breast cancer, which is based on determination of the expression level of the above-mentioned biomarker(s). The invention further provides a screening method for identifying drugs, a method for determining a drug-responding or non-responding phenotype, as well as a method for designing or adapting a treatment regimen. Kits and protein microarrays for carrying out the methods of the invention are also provided herein.

DETAILED DESCRIPTION OF THE INVENTION

Unless stated otherwise, scientific and technical terms used in connection with the present invention shall have the meanings that are commonly understood by those of ordinary skill in the art. Further, unless otherwise required by context, nomenclatures used herein, and techniques of molecular biology and cell culture are those well-known and commonly used in the art.

Nevertheless, with respect to the use of different terms throughout the current specification, the following definitions more particularly apply.

According to the different aspects and embodiments of the invention, the term "comprising" or "containing" means the inclusion of the referent and does not exclude the presence of any other element. By contrast to the term "comprising", the term "consisting of" means the sole inclusion of the referent and thus excludes the presence of any other element.

The term "subject" or "patient" is used herein to describe any member of the animal kingdom, preferably a human being, more preferably a woman.

The term "diagnosing" or "diagnosis", as used in the context of the present invention, means assessing whether a subject suffers or not from a disease. As will be understood by those skilled in the art, such an assessment, although preferred to be, may usually not be correct for 100% of the investigated subjects. This term requires however that a statistically significant portion of subjects can be correctly assessed and, thus, diagnosed. Whether a portion is statistically significant can be easily determined by the skilled person in the art using various well-known statistic evaluation tools, such as determination of confidence intervals, p-value determination, Student's t-test, Mann-Whitney test, etc. Details of such statistical methods can found in Dowdy and Wearden (1983). Statistical methods may notably allow the determination of the sensitivity and the specificity of a diagnostic test. The sensitivity of a diagnostic test can be defined as the proportion of subjects suffering from a disease who will have a positive result, while the specificity of a diagnostic test can be defined as the proportion of subjects without the disease who will have a negative result.

By "breast cancer", it is meant herein a cancer that forms in tissues of the breast, as defined by the National Cancer Institute. Types of breast cancer include, without limitation, ductal carcinoma, which begins in the lining of the milk ducts (thin tubes that carry milk from the lobules of the breast to the nipple); lobular carcinoma, which begins in the lobules (milk glands) of the breast; and invasive breast cancer (breast cancer that has spread from where it began in the breast ducts or lobules to surrounding normal tissue).

By "early breast cancer", it is meant herein a breast cancer that has not spread beyond the breast or the axillary lymph nodes. According to the TNM (Tumor, Nodes, Metastasis) international classification of breast cancer, this includes ductal or lobular carcinoma in situ (pTis N0 M0) and stage I (T1 N0 M0) breast cancers. More particularly, a pTis N0 M0 breast cancer refers to a breast cancer, wherein cancer cells can only be found inside the breast ducts or lobules (T0), without the tumour crossing the basal membrane. A stage I (T1 N0 M0) breast cancer refers to a breast cancer, wherein cancer cells have infiltrated the tissue surrounding the breast ducts and lobules, forming a tumour whose diameter is inferior or equal to 2 cm. The abbreviation N0 means that the cancer has not spread to lymph nodes, while the abbreviation M0 means that there is no distant metastasis. An early breast cancer is generally characterized by a 100% survival rate, within five years from the initial diagnosis.

By "cancer recurrence", "recurring cancer", "cancer relapse or "relapsing cancer", it is meant herein, in the context of potential clinical outcomes of cancer and as defined by the National Cancer Institute, that the cancer has recurred (come back), usually after a period of time during which the cancer could not be detected. A recurring cancer may refer to a cancer that comes back to the same place as the original (primary) tumour or to another place in the body (also known as metastasis).

A "biological fluid sample" according to the invention can be any fluid sample that may be isolated from a subject, including, without limitation, blood or a fractional component thereof (serum, plasma, cellular extract), lymph, tumor interstitial fluid, saliva, mucus, sputum, sweat, or urine. Furthermore, it should be noted that, in the case of a local or a distant cancer recurrence, circulating tumoral cells (CTCs) may be isolated from a biological fluid as defined above, preferably from blood, by techniques well-known in the art. An example of a technique allowing the isolation of circulating tumoral cells (CTCs) is Dean Flow Fractionation (DFF), as established by Hou et al. (2013). In the context of the present invention, the biological fluid sample is preferably a blood sample, such as a serum or plasma sample, and even more preferably a serum sample.

The term "biomarker" according to the invention refers to a polypeptide or protein, fragment thereof, or epitope that is differentially present in a subject as compared to healthy subjects, including differentially modified (e.g. differentially glycosylated) and/or expressed biomarkers. It should be noted that the term "biomarker" includes soluble biomarkers, i.e. biomarkers which are differentially cleaved, secreted, released or shed from a tumor cell in a subject, and are thus detectable in a biological fluid as defined above.

Particularly preferred biomarkers associated with breast cancer according to the invention are listed in the following Table 1.

TABLE 1

Biomarkers of breast cancer

| Symbol | Full name | Accession number UniprotKB/Swiss-Prot (SEQ ID number) |
|---|---|---|
| OLM4 or OLFM4 | Olfactomedin-4 (OLFM4) Alternative name(s): Antiapoptotic protein GW112 G-CSF-stimulated clone 1 protein (hGC-1) hOLfD | Q6UX06 (SEQ ID NO: 1) |
| NENF | Neudesin Alternative name(s): Cell immortalization-related protein 2 Neuron-derived neurotrophic factor Secreted protein of unknown function (SPUF protein) | Q9UMX5 (SEQ ID NO: 2) |
| DSP or DP | Desmoplakin: Isoforms 1 and 2 Alternative name(s): 250/210 kDA paraneoplastic pemphigus antigen | P15924-1 (Isoform 1: SEQ ID NO: 3) P15924-2 (Isoform 2: SEQ ID NO: 4) |

The term "expression level", as applied to a biomarker, refers herein to the amount or level of a biomarker of interest expressed in a cell, tissue, biological fluid, or organ(s). The term "level" as used herein refers to an amount (e.g. relative amount or concentration) of a biomarker that is detectable or measurable in a sample. For example, the level can be a concentration such as µg/L or a relative amount by comparison to a reference expression level. The act of actually "determining the expression level" of a biomarker in a biological sample refers to the act of actively detecting whether a biomarker is expressed in said sample or not, and notably allows to detect whether the biomarker expression is upregulated, downregulated or substantially unchanged when compared to a reference expression level. A "dysregulated expression level" of a given biomarker is, according to the invention, a downregulated or upregulated expression level when compared to a reference expression level.

By "reference expression level" or "control expression level" of a biomarker, it is meant a predetermined expression level of said biomarker, which can be used as a reference in any method of the invention. For example, a reference expression level can be the expression level of a biomarker in a biological sample of a healthy subject, or the average or median, preferably median, expression level in a biological sample of a population of healthy subjects.

Additional definitions are provided throughout the specification.

The present invention may be understood more readily by reference to the following detailed description, including preferred embodiments of the invention, and examples included herein.

The inventors have demonstrated that the expression level of Olfactomedin-4 (OLFM4), Neudesin (NENF) and/or Desmoplakin (DSP) circulating in the blood is dysregulated in subjects suffering from breast cancer. The present invention thus proposes to easily and rapidly diagnose breast cancer in a subject based on the above discovery, by determining the expression level of said biomarker(s), from a mere biological fluid sample such as blood. Such diagnosis method thereby enables to circumvent using conventional, burdensome, or even invasive diagnostic methods such as biopsy, magnetic resonance imaging (MRI), computed tomography (CT), or intrathecal contrast-enhanced CT scan.

Accordingly, in a first aspect, the present invention relates to an in vitro method for diagnosing a breast cancer in a subject, comprising the steps of:

a) determining from a biological fluid sample of a subject the protein expression level of at least one biomarker selected from the group consisting of Olfactomedin-4, Neudesin, Desmoplakin, and any combination thereof; and b) comparing said expression level with a reference expression level of said biomarker.

The above method may optionally further comprise the step c) of determining whether said subject is suffering from breast cancer, based upon the comparison in step b).

Each of the above biomarkers are sufficient to perform a diagnosis according to the invention. Nevertheless, the skilled person in the art will readily understand that the above biomarkers may be combined as a panel of biomarkers, each of which contributing to the final diagnosis of the invention.

In a preferred embodiment, a protein expression level of said at least one biomarker dysregulated by comparison to a reference expression level of said biomarker obtained from a biological fluid sample of at least one healthy subject, is indicative that said subject is suffering from breast cancer.

Preferably, said protein expression level of:

Olfactomedin-4 is superior to said reference expression level; and/or

Neudesin is superior to said reference expression level; and/or

Desmoplakin is inferior or superior to said reference expression level;

in the biological fluid sample of said subject suffering from breast cancer.

In other words, a protein expression level of Olfactomedin-4 in step a) superior to the reference expression level of Olfactomedin-4 obtained from a biological fluid sample of at least one healthy subject, is indicative that the tested subject is suffering from breast cancer.

Similarly, a protein expression level of Neudesin in step a) superior to the reference expression level of Neudesin obtained from a biological fluid sample of at least one healthy subject, is indicative that the tested subject is suffering from breast cancer.

This means as well that a protein expression level of Desmoplakin in step a) inferior to the reference expression level of Desmoplakin obtained from a biological fluid sample of at least one healthy subject, is indicative that the tested subject is suffering from breast cancer.

This also means that a protein expression level of Desmoplakin in step a) superior to the reference expression level of Desmoplakin obtained from a biological fluid sample of at least one healthy subject, is indicative that the tested subject is suffering from breast cancer.

It shall be further understood that the present method, as well as other methods of the invention, encompass the use of any combination of the above biomarkers.

The protein expression level of any one of Olfactomedin-4, Neudesin and Desmoplakin, or of any combination thereof, may further indicate the stage of breast cancer.

Accordingly, in a preferred embodiment, said expression level of Olfactomedin-4 superior to said reference expression level is indicative that the breast cancer is an early breast cancer.

In another preferred embodiment, said expression level of Neudesin superior to said reference expression level is indicative that the breast cancer is an early breast cancer.

Yet, in another preferred embodiment, said expression level of Desmoplakin inferior to said reference expression level is indicative that the breast cancer is an early breast cancer.

Such diagnosis test of early breast cancer is particularly useful for patients at risk (e.g. having a family history of breast cancer), and for patients for which small breast tumours (e.g. tumour size below 1 cm) can not be accurately detected by conventional diagnostic methods such as ultrasound.

Still, in another preferred embodiment, said expression level of Desmoplakin superior to said reference expression level is indicative that the breast cancer is a recurring breast cancer. Such diagnosis test of a recurring breast cancer is particularly useful for the monitoring of a patient previously suffering from breast cancer. Notably if performed early on, such diagnostic test can help to improve the prognosis and survival of the patient.

By superior to a reference expression level, it is meant that the ratio between the expression level of said biomarker and the reference expression level is above 1.

By inferior to a reference expression level, it is meant that the ratio between the expression level of said biomarker and the reference expression level is below 1.

Alternatively, said expression level may be indicated as the concentration of biomarker in the tested biological fluid.

Accordingly, said protein expression level of Olfactomedin-4 is preferably superior to 30, 31, 32, 34, 35, 36, 37, 38, 39, 40, 50, 60, 70, 80, 90, 100, 150, 200 ng/mL, more preferably superior to 30, 31, 32, 34, 35, 36, 37, 38, 39, 40 ng/mL, most preferably superior to 31 ng/mL, in the biological fluid sample of said subject suffering from breast cancer, preferably from early breast cancer. Indeed, as illustrated in the experimental results, the inventors have demonstrated in a first cohort of 335 breast cancer patients and 65 healthy subjects that the sensitivity of a breast cancer diagnostic test based on Olfactomedin-4 is 67%, while the specificity of such test is 88%, for an Olfactomedin-4 sera concentration above 40 ng/mL. They further demonstrated in a second cohort of 766 breast cancer patients and 195 healthy subjects that the sensitivity of a breast cancer diagnostic test based on Olfactomedin-4 is ranging from 64 to 78%, with a specificity of about 80-90% for an Olfactomedin-4 sera concentration above 31 ng/mL. Similar values were observed in early breast cancer patients.

Still, said protein expression level of Neudesin is preferably superior to 15, 16, 17, 18, 19, 20, 25, 30, 35, 40 ng/mL, more preferably superior to 15, 16, 17, 18, 19, 20 ng/mL, most preferably superior to 16 ng/mL, in the biological fluid sample of said subject suffering from breast cancer, preferably early breast cancer. Indeed, as illustrated in the experimental results, the inventors have demonstrated in a first cohort of 335 breast cancer patients and 65 healthy subjects, that the sensitivity of a breast cancer diagnostic test based on Neudesin is 47%, while the specificity of such test reached 91%, for a Neudesin sera concentration above 20 ng/mL. They further demonstrated in a second cohort of 766 breast cancer patients and 195 healthy subjects that the sensitivity of a breast cancer diagnostic test based on Neudesin is ranging from 52 to 60%, with a specificity reaching about 75-80% for a Neudesin sera concentration above 16 ng/mL. Similar values were observed in early breast cancer patients.

Still, said protein expression level of Desmoplakin is preferably inferior to 600, 500, 400, 300 pg/mL, more preferably inferior to 600 pg/mL, in the biological fluid sample of said subject suffering from early breast cancer.

Yet, still, said protein expression level of Desmoplakin is preferably superior to 1800, 1900, 2000 pg/mL, more preferably superior to 1800 pg/mL, in the biological fluid sample of said subject suffering from a recurring breast cancer.

As indicated above, the above biomarkers can be combined as a panel of biomarkers, each of which contributing to the final diagnosis of the invention. Indeed, the inventors have demonstrated that such combination increases the sensitivity and/or the specificity of the diagnosis test of the invention.

Accordingly, in a preferred embodiment, the protein expression level of at least two, preferably three, of said biomarkers are determined in step a).

Preferably, the protein expression level of Olfactomedin-4 and Neudesin are determined in step a) of the above method. The combination of these biomarkers is particularly useful for diagnosing breast cancer, such as for diagnosing an early breast cancer. That is to say that, in a preferred embodiment, said protein expression level of:

Olfactomedin-4 is superior to said reference expression level, and

Neudesin is superior to said reference expression level, in the biological fluid sample of said subject suffering from breast cancer, such as an early breast cancer.

In other words, a protein expression level of:

Olfactomedin-4 superior to the reference expression level of Olfactomedin-4 obtained from a biological fluid sample of at least one healthy subject, and Neudesin superior to the reference expression level of Neudesin obtained from a biological fluid sample of at least one healthy subject, is indicative that the tested subject is suffering from breast cancer, such as an early breast cancer.

Indeed, as illustrated in the experimental results, the inventors have demonstrated in a first cohort of 335 breast cancer patients and 65 healthy subjects that the sensitivity of a breast cancer diagnostic test based on the combination of Olfactomedin-4 and Neudesin is 74%, while the specificity of such test is 78%, for a sera concentration of those biomarkers above 44 ng/mL. They further demonstrated in a second cohort of 766 breast cancer patients and 195 healthy subjects that the sensitivity of a breast cancer diagnostic test based on the combination of Olfactomedin-4 and Neudesin is ranging from 75 to 85%, with a specificity reaching 87% for a sera concentration of those biomarkers above 38 ng/mL. Similar values were observed in early breast cancer patients. The combination of Olfactomedin-4 and Neudesin thus increases the sensitivity and/or specificity values of the diagnostic test of the invention, by comparison to a test based on only one of these biomarkers.

Alternatively, the protein expression level of Olfactomedin-4 and Desmoplakin are preferably determined in step a) of the above method. The combination of these biomarkers is particularly useful for diagnosing breast cancer, and more particularly an early breast cancer. That is to say that, in a preferred embodiment, said protein expression level of:

Olfactomedin-4 is superior to said reference expression level, and

Desmoplakin is inferior to said reference expression level, in the biological fluid sample of said subject suffering from breast cancer, and preferably from an early breast cancer.

In other words, a protein expression level of:

Olfactomedin-4 superior to the reference expression level of Olfactomedin-4 obtained from a biological fluid sample of at least one healthy subject, and Desmoplakin inferior to the reference expression level of Desmoplakin obtained from a biological fluid sample of at least one healthy subject, is indicative that the tested subject is suffering from breast cancer, and preferably from an early breast cancer.

Indeed, as illustrated in the experimental results, the inventors have demonstrated that the sensitivity of an early breast cancer diagnostic test based on the combination of Olfactomedin-4 and Desmoplakin is 87%, while the specificity of such test is 84%.

Alternatively, the protein expression level of Neudesin and Desmoplakin are preferably determined in step a) of the above method. The combination of these biomarkers is particularly useful for diagnosing breast cancer, and more particularly an early breast cancer. That is to say that, in a preferred embodiment, said protein expression level of:

Neudesin is superior to said reference expression level, and

Desmoplakin is inferior to said reference expression level, in the biological fluid sample of said subject suffering from breast cancer, and preferably from an early breast cancer.

In other words, a protein expression level of:

Neudesin superior to the reference expression level of Neudesin obtained from a biological fluid sample of at least one healthy subject, and Desmoplakin inferior to the reference expression level of Desmoplakin obtained from a biological fluid sample of at least one healthy subject, is indicative that the tested subject is suffering from breast cancer, and preferably from an early breast cancer.

Still preferably, the protein expression level of Olfactomedin-4, Neudesin and Desmoplakin are determined in step a) of the above method. The combination of these three biomarkers is particularly useful for diagnosing breast cancer, more particularly an early breast cancer. That is to say that, in a preferred embodiment, said protein expression level of:

Olfactomedin-4 is superior to said reference expression level,

Neudesin is superior to said reference expression level, and

Desmoplakin is inferior to said reference expression level, in the biological fluid sample of said subject suffering from breast cancer, and preferably from an early breast cancer.

In other words, a protein expression level of:

Olfactomedin-4 superior to the reference expression level of Olfactomedin-4 obtained from a biological fluid sample of at least one healthy subject, Neudesin superior to the reference expression level of Neudesin obtained from a biological fluid sample of at least one healthy subject, and Desmoplakin inferior to the reference expression level of Desmoplakin obtained from a biological fluid sample of at least one healthy subject, is indicative that the tested subject is suffering from a breast cancer, and preferably from an early breast cancer.

It shall be further understood that the information obtained using the methods of the invention as described herein may be used in combination with other information, such as, but not limited to, expression levels of additional biomarkers which may be standard biomarkers, clinical chemical parameters, histopathological parameters, or age, gender and/or weight of the subject.

Accordingly, in a further preferred embodiment, the in vitro diagnostic method of the invention further comprises the step of determining the protein expression level of at least one standard biomarker associated with breast cancer, such as estrogen receptor (ER), progesterone receptor (PR) or human epidermal growth factor receptor 2 (HER2).

As indicated above, in the context of the present invention, the expression level is measured at the protein level. Methods for measuring protein expression levels are well-known in the art and are notably reviewed by Reeves et al. (2000) and Schena (2005). Those methods generally involve contacting a biological sample of interest with one or more detectable reagents that is or are suitable for measuring protein expression level, such as an antibody, and subsequently determining protein expression level based on the level of detected reagent, preferably after normalization. Examples of methods which generally involve the use of an antibody include, without limitation, Western blot, immunoblot, enzyme-linked immunosorbant assay (ELISA), enzyme-linked immunospot (ELISPOT), radioimmunoassay (RIA), immunohistochemistry and immunoprecipitation. Other methods suitable for measuring a protein expression level, which do not necessarily involve the use of an antibody, may be used, including, without limitation, fluorescence activated cell sorting (FACS), microscopy such as atomic force microscopy, flow cytometry, microcytometry, protein binding assay, ligand binding assay, microarray, polyacrylamide gel electrophoresis such as SDS-PAGE, surface plasmon resonance (SPR), Förster resonance energy transfer (FRET), Bioluminescence resonance energy transfer (BRET), chemiluminescence, fluorescent polarization, phosphorescence, mass spectrometry such as liquid chromatography mass spectrometry (LC-MS) or liquid chromatography/mass spectrometry/mass spectrometry (LC-MS-MS), matrix-assisted laser desorption/ionization time-of-flight (MALDI-TOF), surface-enhanced laser desorption/ionization time-of-flight (SELDI-TOF), and magnetic resonance imaging (MRI).

According to the different aspect and preferred embodiments of the present invention, the step of determining the expression level of a biomarker of interest preferably further comprises a substep of normalizing the expression level of said biomarker. The method for normalizing expression level can be selected based upon the method used for measuring expression level. For example, if a Western-blot is performed, the expression level of a biomarker of interest in a biological sample may be normalized by assessing in parallel in said sample the expression level of a protein which is usually constitutively expressed in any cell of a living organism, preferably at the same expression level whether the cell is healthy or not (e.g. cancerous or not). An example of constitutively expressed protein is a housekeeping protein, which may be selected, without limitation, among actin, beta-tubulin, and Glyceraldehyde 3-phosphate dehydrogenase (GAPDH), to name a few. Alternatively, if an ELISA is performed, involving for example a colorimetric detection method, protein expression level can be normalized by total cell number. Yet, still alternatively, if a microarray is performed, protein expression level can be normalized, for example, by loess-regression. For a detailed review of normalization methods of protein expression level in an antibody microarray, one skilled in the art may refer to Hamelinck et al. (2005).

All these methods for measuring and normalizing protein expression level are well-known to the skilled person, and thus do not need to be further detailed herein. Should the skilled person wish to use any of the above methods involving the use of an antibody to measure a biomarker protein expression level, one may use any appropriate commercial antibody specific for said biomarker. Alternatively, based on the knowledge of the amino-acid sequence of a biomarker of interest, it is easy to the skilled person to design suitable reagent(s) to measure expression level in any biological sample. For example, an antibody directed against a specific biomarker may be prepared by any conventional method, e.g. by immunizing an animal, such as a mouse, with an immunogenic form of said biomarker which elicits an antibody response in said animal. Methods for producing polyclonal and monoclonal antibodies are well described in the literature (see notably Kohler and Milstein, 1975; Kozbor et al., 1983; Roder et al., 1986; and Huse et al., 1986), and therefore need not be further detailed herein.

As indicated above, the comparison of a determined or tested expression level with a reference expression level can be done by merely calculating the ratio between the expression level of a biomarker of interest in the tested biological sample and in at least one reference sample, preferably after normalization as described above. Accordingly, a ratio above 1 is indicative that the biomarker is overexpressed, while a ratio below 1 is indicative that the biomarker is underexpressed (i.e. downregulated).

In another aspect of the present invention, the biomarkers disclosed herein can be used to determine if a patient will respond or not to a cancer therapy. Associating a patient's response to treatment with such biomarker(s) can indeed elucidate new opportunities for treatment in non-responding patients or indicate one treatment over other treatment choices.

Therefore, the present invention further provides an in vitro method for determining a drug-responding or non-responding phenotype in a subject suffering from breast cancer, comprising the steps of:
  a) determining from a biological fluid sample of said subject the protein expression level of at least one biomarker selected from the group consisting of Olfactomedin-4, Neudesin, Desmoplakin, and any combination thereof;
  b) comparing the protein expression level in step a) to a reference expression level of said biomarker; and
  c) determining from said comparison the drug-responding or non-responding phenotype.

According to the present invention, a "drug-responding phenotype" refers to a response state of a subject to the administration of a drug. A "response state" means that said subject responds to the treatment, i.e. that said treatment is efficacious in said subject. A responding phenotype is thus characterized by an improvement in clinical signs, i.e. in the context of the present invention, a responding phenotype is characterized for example by a regression or disappearance of breast cancer cells and metastases thereof, if any. By contrast, a "drug-non responding phenotype" refers to the absence in said subject of a state response, meaning that said subject is refractory to the treatment.

Protein expression level of the above-mentioned biomarkers in a subject suffering from breast cancer are as described above.

In a further aspect of the present invention, the biomarkers disclosed herein can be used to design or adapt a breast cancer treatment. In particular, such treatment may be designed or adapted once a subject has been diagnosed as suffering from breast cancer, according to the method of the invention.

Accordingly, the present invention provides herein a method for designing or adapting a treatment regimen for a subject suffering from breast cancer, comprising the steps of:
  a) determining from a biological sample of said subject a drug-responding or non-responding phenotype, according to the in vitro method described above; and
  b) designing or adapting a treatment regimen for said subject based upon said responding or non-responding phenotype.

The present method is particularly useful for offering a therapy tailored to each patient affected by breast cancer.

The term "treatment regimen" refers herein to a treatment plan that specifies the type of treatment (i.e. type of drug or combination of drugs, and mode of administration of said drug(s)), dosage, schedule and/or duration of a treatment provided to a subject in need thereof. A dosage, schedule and/or duration of treatment can vary, depending on the progression of disease and the selected type of treatment. In this regard, in addition to the drugs that can be identified according to the screening method of the invention, therapeutic agents that may be used in the treatment regimen according to the invention include, without limitation, chemotherapeutic agents; hormone therapeutic agents such as tamoxifen or aromatase inhibitors (e.g. Raloxifene, Toremifene, Fulvestrant, Anastrozole, Exemestane, Letrozole); human epidermal growth factor receptor 2 (HER2) inhibitors such as trastuzumab (Herceptin), pertuzumab, or lapatinib; vascular endothelial growth factor receptor (VEGFR) inhibitors such as bevacizumab; epidermal growth factor receptor (EGFR) inhibitors such as cetuximab and panitumumab; and any combination thereof.

Standard chemotherapeutic drugs for treating breast cancer include, without limitation, platinum-based agents such as oxaliplatin, cisplatin, carboplatin, spiroplatin, iproplatin, and satraplatin; alkylating agents such as cyclophosphamide, ifosfamide, chlorambucil, busulfan, melphalan, mechlorethamine, uramustine, thiotepa, and nitrosoureas; anti-metabolites such as 5-fluorouracil, azathioprine, 6-mercaptopurine, methotrexate, leucovorin, capecitabine, cytarabine, floxuridine, fludarabine, gemcitabine, pemetrexed, or raltitrexed; plant alkaloids such as vincristine, vinblastine, vinorelbine, vindesine, podophyllotoxin, or taxanes such as paclitaxel and docetaxel; topoisomerase inhibitors such as irinotecan, topotecan, amsacrine, etoposide (VP16), etoposide phosphate, or teniposide; antitumor antibiotics such as anthracyclines (e.g. doxorubicin, daunorubicin, epirubicin, mitoxantrone), actinomycin, bleomycin, mitomycin, or plicamycin; and any combination thereof.

In the above method, the treatment regimen that is designed or adapted and optionally administered to the subject depends on the responding or non-responding phenotype. In particular, a treatment regimen may be selected for the first time, continued, adjusted or stopped based upon said phenotype. For example, a treatment regimen may be adjusted by increasing the dose to be administered, or stopped and switched to an alternative treatment regimen, if the subject is non-responding. Still, alternatively, a treatment regimen may be selected for the first time or continued if a subject is responding. One skilled in the art would nevertheless easily design or adjust the type of treatment with the dosage, schedule and duration of treatment, depending upon the phenotype of the subject.

Furthermore, based upon said phenotype, the selected treatment regimen can be an aggressive one which is expected to result in the best clinical outcome (e.g., regression and/or disappearance of breast cancer) and which may be associated with some discomfort to the subject or adverse side effects (e.g., damage to healthy cells or tissue), or a more moderate one which may only slow the progression of the disease. An example of aggressive treatment regimen include a treatment regimen as described above combined with surgical intervention to remove tumoral cells, tissue or organs and/or an exposure to radiation therapy. An aggressive treatment regimen may also include a higher dosage of the therapeutic agent(s), a more frequent administration of said agent(s), and/or a longer duration of treatment.

Thus, once a treatment regimen has been determined in accordance with the teachings of the invention, the subject may receive the appropriate treatment.

Therefore, in another aspect, the invention relates to a method for treating breast cancer in a subject in need thereof, comprising the steps of:
  a) determining from a biological sample of said subject a drug-responding or non-responding phenotype, according to the method described above; and
  b) administering to said subject said drug if the phenotype is a responding phenotype.

The term "administering" as used herein means that the drug(s) of interest is delivered or dispensed to a subject orally, or parenterally such as by subcutaneous, intravenous, intramuscular, intrathecal or intraperitoneal injection.

In another aspect of the present invention, the biomarkers disclosed herein may be used for drug screening purposes. In particular, novel drug assays may be provided, which identify therapeutics efficiently interfering with the proliferation of breast cancer cells that aberrantly express those biomarkers. Current treatment of breast cancer mainly relies on chemotherapy and/or antiangiogenic drugs, which may be combined, if need be, with surgery.

Accordingly, in the present aspect, the invention relates to a screening method for identifying a drug or combination of drugs suitable for treating breast cancer, comprising the steps of:
a) contacting isolated breast cancer cells or cell line displaying a breast cancer phenotype with a candidate drug or combination of candidate drugs;
b) determining, from said cells or cell line contacted with said drug or combination of drugs, the protein expression level of at least one biomarker selected from the group consisting of Olfactomedin-4, Neudesin, Desmoplakin, and any combination thereof; and
c) comparing the protein expression level of said biomarker in step b) to its expression level in the absence of said drug or combination of drugs.

By "drug" or "agent", it is meant herein a compound such as chemical or a biological molecule that can be administered or tested according to the invention. A chemical can be of any composition such as inorganic or organic. A biological molecule can be a molecule of any biological origin that can be found in or produced by, at least in part, a cell, such as, without limitation, peptides or proteins such as antibodies or affibodies, lipids, nucleic acids such as RNAi or aptamers, carbohydrates, and any combination thereof.

By "drug suitable for treating breast cancer", it is meant herein a drug that can slow or stop the growth of breast cancer cells and metastases thereof, if any, either by killing said cells, or by slowing or stopping their uncontrolled division.

Furthermore, it shall be understood that by "breast cancer cells or cell line" according to the invention, it is preferably meant breast cancer cells or cell line wherein the protein expression level of Olfactomedin-4, Neudesin, and/or Desmoplakin is dysregulated by comparison to a reference expression level of said biomarker(s) in the breast cells of at least one healthy subject. Preferably, the cells or cell line used in the present screening method are breast cancer cells isolated from a subject diagnosed as suffering from breast cancer according to the method of the invention.

The screening method described above is preferably an in vitro screening method. For example, the cells or cell line used in the present method can be cultured in a three-dimensional (3D) culture system, so as to mimic a breast tumour micro-environment. To do so, said cells can be embedded in an extracellular matrix (ECM) as described by Weigelt et al. (2008), Kenny et al. (2007) and Li et al. (2010).

In order to assess the efficacy of the candidate anti-cancer agent, said cells or cell line may, as an alternative or as a validation test, be grafted to an animal, such as a mouse. Should such xenograft be carried out, the screening method described above preferably further comprises the step of killing said animal.

In a preferred embodiment of the above method, a protein expression level of Olfactomedin-4 in step b) inferior to the protein expression level of said biomarker in the absence of said drug or combination of drugs is indicative that said drug or combination of drugs is suitable for treating breast cancer.

In a preferred embodiment, a protein expression level of Neudesin in step b) inferior to the protein expression level of said biomarker in the absence of said drug or combination of drugs is indicative that said drug or combination of drugs is suitable for treating breast cancer.

In a further preferred embodiment, a protein expression level Desmoplakin in step b) superior to the protein expression level of said biomarker in the absence of said drug or combination of drugs is indicative that said drug or combination of drugs is suitable for treating early breast cancer.

Yet, in another preferred embodiment, a protein expression level of Desmoplakin in step b) inferior to the protein expression level of said biomarker in the absence of said drug or combination of drugs is indicative that said drug or combination of drugs is suitable for treating a recurring breast cancer.

One skilled in the art would readily understand from the data provided herein that the above-mentioned biomarkers may be combined to aid in the identification of a drug or combination of drugs. It is within the skill of the person in the art to select the appropriate biomarker to be combined.

Preferably, a protein expression level of Olfactomedin-4 and Neudesin in step b) inferior to the protein expression level of said biomarkers in the absence of said drug or combination of drugs is indicative that said drug or combination of drugs is suitable for treating breast cancer such as an early breast cancer.

Preferably, a protein expression level of:
Desmoplakin in step b) superior to the protein expression level of said biomarker in the absence of said drug or combination of drugs, and
Olfactomedin-4 in step b) inferior to the protein expression level of said biomarker in the absence of said drug or combination of drugs,
is indicative that said drug or combination of drugs is suitable for treating breast cancer, and preferably an early breast cancer.

Preferably, a protein expression level of:
Desmoplakin in step b) superior to the protein expression level of said biomarker in the absence of said drug or combination of drugs, and
Neudesin in step b) inferior to the protein expression level of said biomarker in the absence of said drug or combination of drugs,
is indicative that said drug or combination of drugs is suitable for treating breast cancer, and preferably an early breast cancer.

Still preferably, a protein expression level of:
Olfactomedin-4 and Neudesin in step b) inferior to the protein expression level of said biomarkers in the absence of said drug or combination of drugs, and
Desmoplakin in step b) superior to the expression level of said biomarker in the absence of said drug or combination of drugs,
is indicative that said drug or combination of drugs is suitable for treating breast cancer, and preferably an early breast cancer.

In another aspect, the present invention provides kits that can be employed in the methods described herein. In this regard, the invention relates to a kit for use in any method described above, comprising or consisting of:
a) at least one reagent capable of specifically determining the protein expression level of at least one biomarker selected from the group consisting of Olfactomedin-4, Neudesin, Desmoplakin, and any combination thereof; and b) instructions for performing said method.

As used herein, the term "instructions" refers to a publication, a recording, a diagram, or any other medium which can be used to communicate how to perform a method of the invention. Said instructions can, for example, be affixed to a container which contains said kit. Preferably, the instructions for using said kit include a reference expression level of said biomarker(s).

The term "reagent capable of specifically determining the protein expression level [of a given biomarker]" designates a reagent or a set of reagents which specifically recognizes said biomarker and allows for the quantification of its protein expression level. These reagents can be for example antibodies, aptamers or affibodies specifically recognizing a biomarker. In the context of the present invention, such reagent is said to be "specific" for its target (i.e. biomarker) or "recognizes specifically" its target if it 1) exhibits a threshold level of binding activity, and/or 2) does not significantly cross-react with target molecules known to be related to the biomarker of interest. The binding affinity of such reagent can be easily determined by one skilled in the art, for example, by Scatchard analysis. Cross-reactivity of a reagent can as well be easily determined by one skilled in the art, and thus need to be further detailed herein.

In a preferred embodiment, the kit of the invention may further comprise:

c) at least one reagent capable of specifically determining the protein expression level of at least one standard breast cancer biomarker, such as estrogen receptor (ER), progesterone receptor (PR) or human epidermal growth factor receptor 2 (HER2).

In order to normalize protein expression level, the kit of the invention may also optionally comprise at least one reagent capable of specifically determining the protein expression level of a housekeeping protein, such as actin, beta-tubulin, or Glyceraldehyde 3-phosphate dehydrogenase (GAPDH).

In yet another aspect, the methods of the invention can be practiced using a microarray, so as to notably determine the expression level of biomarkers of interest in the present invention.

The term "microarray" refers herein to a spatially defined and separated collection of individual biological molecules which are immobilized on a solid surface, and to which one or several biomarkers of interest specifically bind(s). Those biological molecules allow for the determination of the expression level of said biomarker(s), and may be antibodies, affibodies or aptamers if the microarray is a protein microarray, which is a preferred type of microarray according to the invention. Protein microarrays technologies are well-known to the skilled person, and are notably described in Mitchell (2002), Haab (2005), and Eckel-Passow et al. (2005), and in U.S. Pat. Nos. 6,087,102, 6,139,831, and 6,087,103. For determination of protein expression level of one or several biomarkers by using such array, two technologies can typically be used: 1) direct labeling, and 2) indirect labeling, as described for example by Kingsmore et al. (2006). In the "direct labeling" method, the protein of interest (i.e. biomarker of the invention, or target) obtained from a sample, such as a biological sample, is labeled with a specific marker (e.g. a fluorescent or a radioisotope marker), and subsequently hybridized to the microarray by specifically binding to a reagent recognizing said biomarker, said reagent being conjugated to the surface of the protein microarray. If the expression level of several biomarkers is to be assessed, each biomarker is labeled with a distinct marker. In the "indirect labeling" method, the sample containing the biomarker of interest is hybridized to the microarray by specifically binding to an unlabeled reagent recognizing said biomarker, said reagent being conjugated to the surface of the protein microarray, and a secondary labeled reagent, specifically recognizing as well said biomarker, is then added. The specificity and sensitivity of such indirect labeling method can further be enhanced by using a third labeled reagent, recognizing the secondary reagent (sandwich assay). Similarly, if the expression level of several biomarkers is to be assessed in the indirect labeling method, each secondary or third reagent is labeled with a distinct marker. Label-free systems may also be used to determine the expression level of a biomarker on a protein microarray; in such system, detection of the biomarker, and hence of its expression level, may be done by surface plasmon resonance (SPR), microcantilever biosensing, SELDI-TOF-MS, or atomic force microscopy (Chandra et al., 2011).

Therefore, the invention further relates herein to a protein microarray for use in any method described above, comprising or consisting of:

a) at least one a reagent capable of specifically determining the protein expression level of at least one biomarker selected from the group consisting of Olfactomedin-4, Neudesin, Desmoplakin, and any combination thereof.

In a preferred embodiment, said protein microarray may further comprise:

b) at least one reagent capable of specifically determining the protein expression level of at least one standard breast cancer biomarker, such as estrogen receptor (ER), progesterone receptor (PR) or human epidermal growth factor receptor 2 (HER2).

In order to normalize protein expression level, the microarray of the invention may also optionally comprise at least one reagent capable of specifically determining the expression level of a housekeeping protein, such as actin, beta-tubulin, or Glyceraldehyde 3-phosphate dehydrogenase (GAPDH).

The present invention will be better understood in the light of the following detailed description of experiments, including examples. Nevertheless, the skilled artisan will appreciate that this detailed description is not limitative and that various modifications, substitutions, omissions, and changes may be made without departing from the scope of the invention.

Flow diagram showing the filtering algorithm used to identify 5 prospective candidate biomarkers, namely Versican (VCAN), Tenascin (TNC), Olfactomedin-4 (OLFM4), Neudesin (NENF) and Desmoplakin (DSP).

Figure 2:
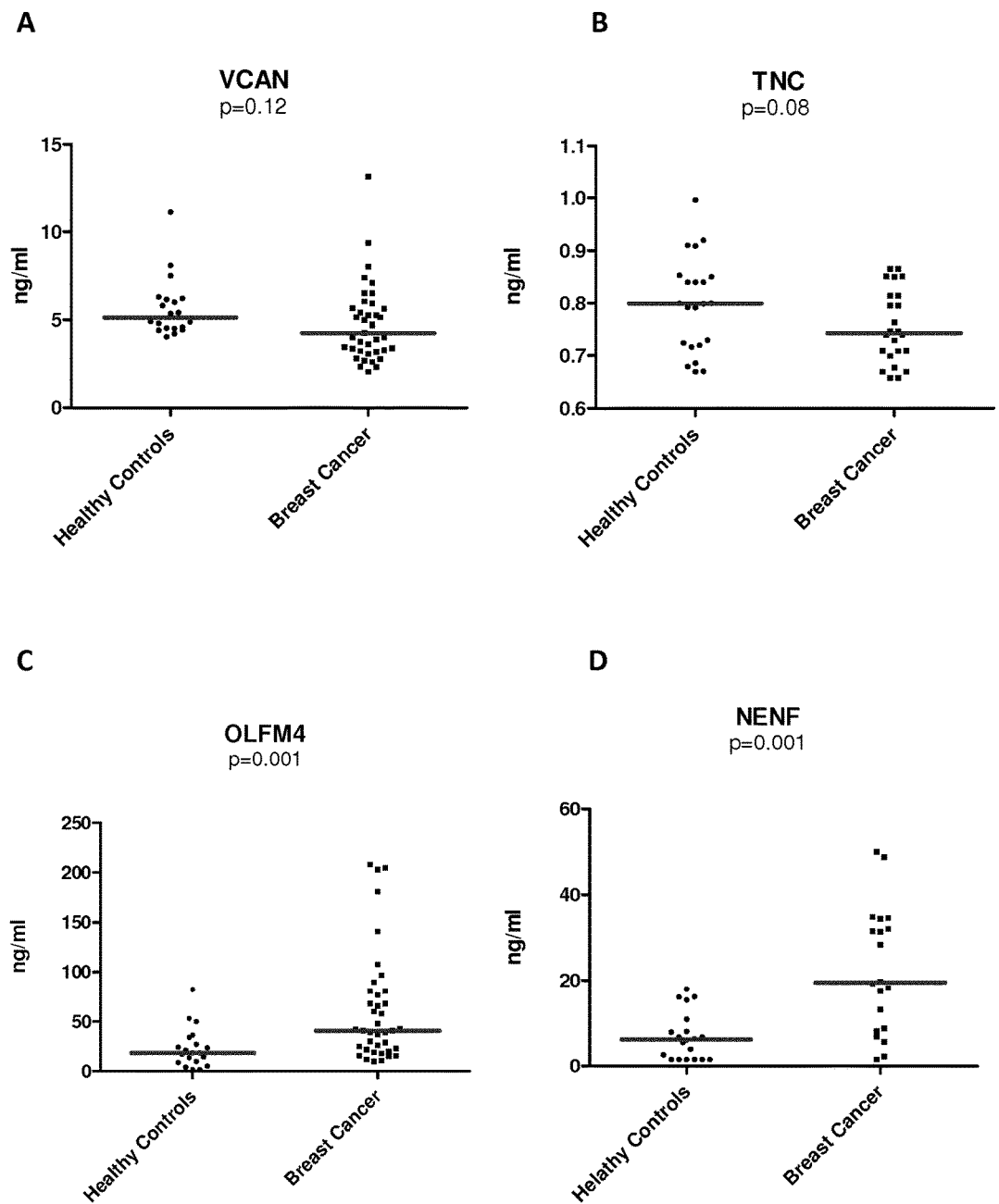
Figure 2:
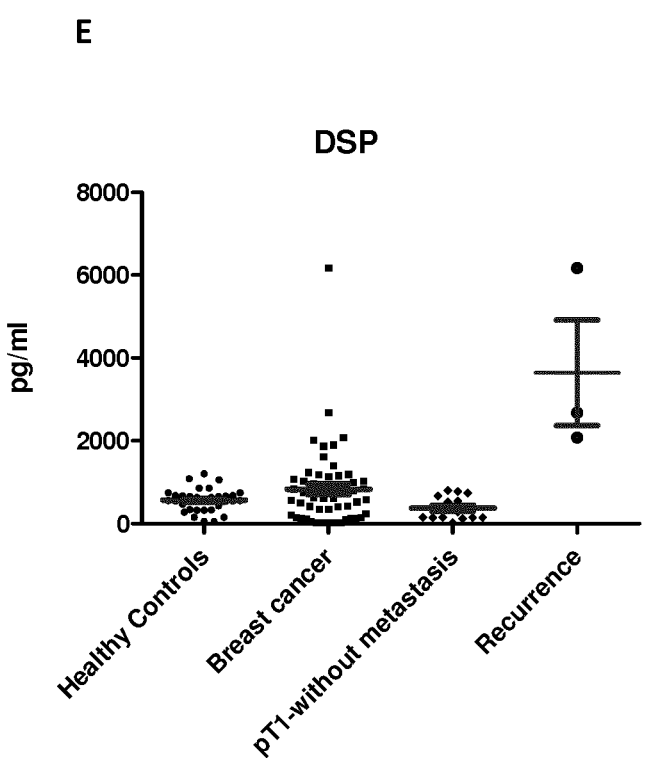

FIG. 2: Preliminary verification of Versican (A), Tenascin (B), Olfactomedin-4 (C), Neudesin (D) and Desmoplakin (E) expression in breast cancer patients versus healthy controls Serum concentrations of these five candidate biomarkers in patients diagnosed with breast cancer and healthy controls sera were measured using ELISA. The corresponding concentration medians are represented by a horizontal line. The most promising candidates are OLFM4, NENF and DSP.

Figure 3:
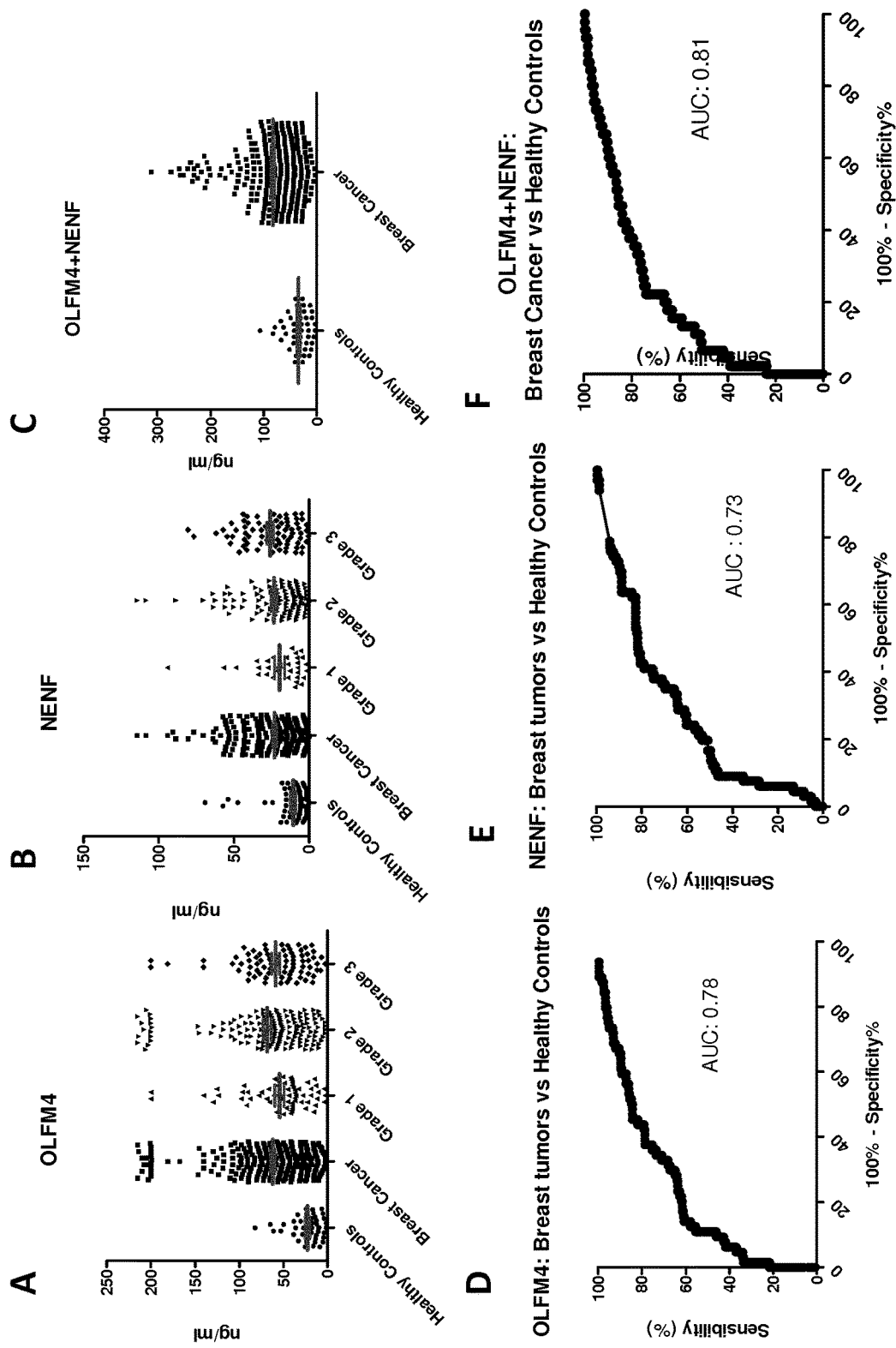

FIG. 3: OLFM4 and NENF expression levels in serum samples of breast cancer patients (first study)

A: Expression level of circulating olfactomedin-4 in the serum of 335 breast cancer patients and in that of 65 healthy controls; the Mann-Whitney test for independent samples was used to calculate the significance of the results. Olfactomedin-4 was significantly over-expressed (p<0.0001) in the patients with breast cancer and in each of the sub-groups by grade.

B: Expression level of circulating Neudesin in the serum of 335 breast cancer patients and in that of 65 healthy controls; the Mann-Whitney test for independent samples was used to calculate the significance of the results. Neudesin was significantly over-expressed (p<0.0001) in the patients with breast cancer and in each of the sub-groups by grade (p=0.008 for grade 1 and p<0.0001 for grade 2 and 3).

C: Expression levels of circulating Olfactomedin-4 and neudesin in the serum of 335 patients with breast cancer and in that of 65 healthy controls; the combination of these two proteins is significantly over-expressed in the breast cancer patients group (p<0.0001).

D: ROC curve of the Olfactomedin-4 analysis to distinguish breast cancers (n=335) from healthy controls (n=65); the area under the curve (AUC) for patients of all stages combined compared to the population without cancer was 0.78 (CI 95: 0.74-0.85); the sensitivity of the test was 67%, while specificity was 88% for a concentration >40 ng/ml.

E: ROC curve of the Neudesin analysis to distinguish breast cancers (n=241) from healthy controls (n=65); the area under the curve (AUC) for patients of all stages combined compared to the population without cancer was 0.73 (CI 95: 0.70-0.80); the sensitivity of the test was 47%, while specificity was 91% for a concentration >20 ng/ml.

F: ROC curve of the Olfactomedin-4+Neudesin analysis to distinguish breast cancers (n=241) from healthy controls (n=65); the area under the curve (AUC) for patients of all stages combined compared to the population without cancer was 0.81 (CI 95: 0.74-0.86); the sensitivity of the test was 74%, while specificity was 78% for a concentration >44 ng/ml.

Figure 4:
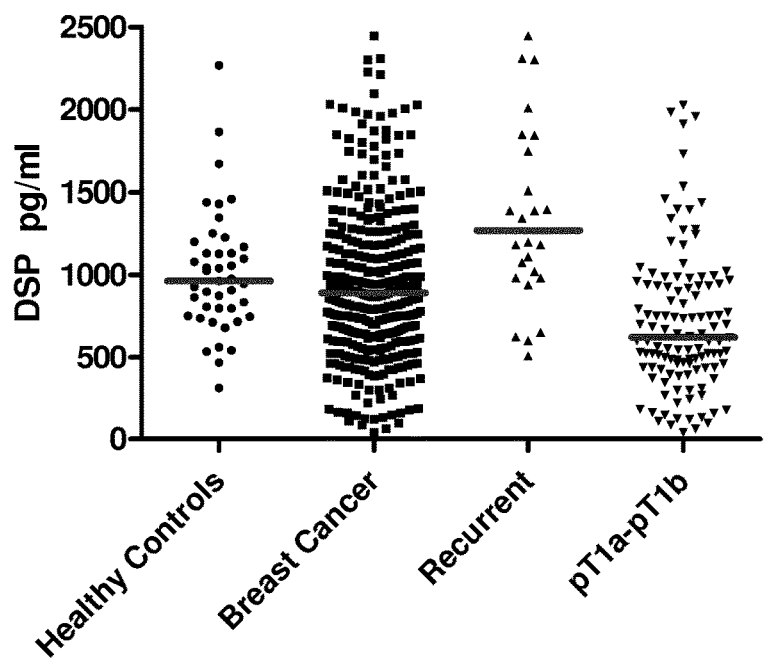

FIG. 4: DSP expression levels in serum samples of breast cancer patients (first study)

Expression level of circulating DSP in the serum of 241 breast cancer patients and in that of 65 healthy controls; the Mann-Whitney test for independent samples was used to calculate the significance of the results. Desmoplakin was significantly under-expressed (p=0.0037) in pT1a-pT1b breast cancer group and significantly over-expressed (p=0.0069) in recurrence group.

Figure 5:
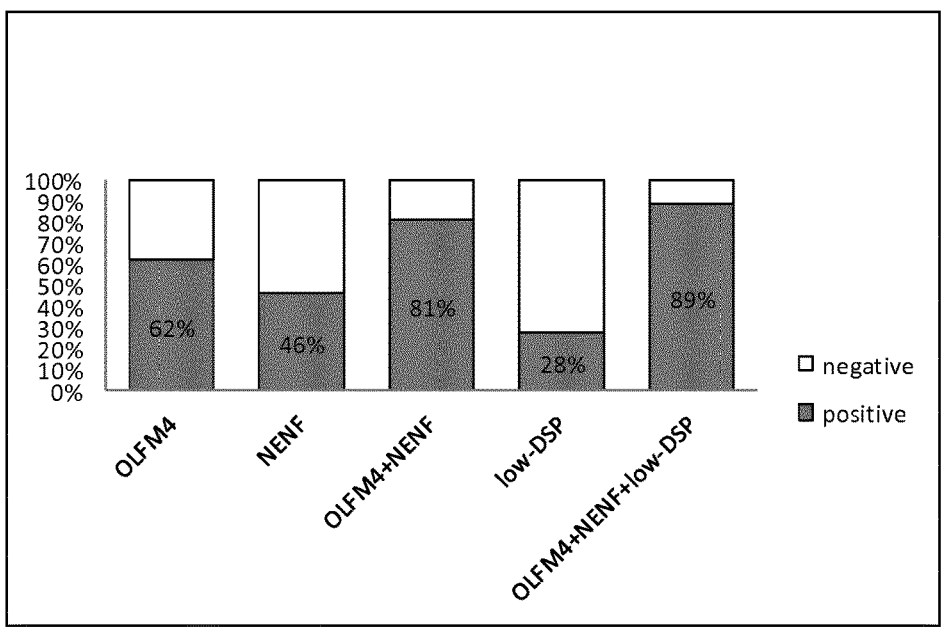

FIG. 5: OLFM4, NENF and DSP dysregulation in breast cancer patients (first study)

Proportion of breast cancer patients tested positive for the elevation of OFLM4 and NENF and decrease of DSP.

Figure 6:
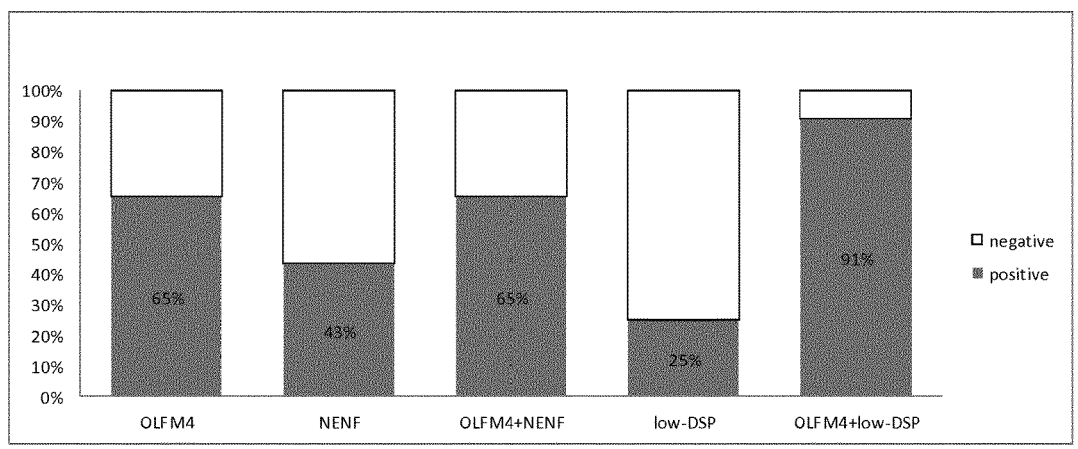
Figure 6:
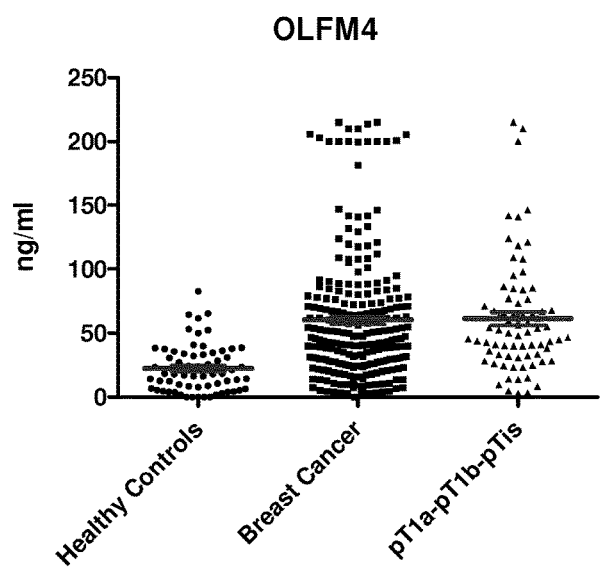
Figure 6:
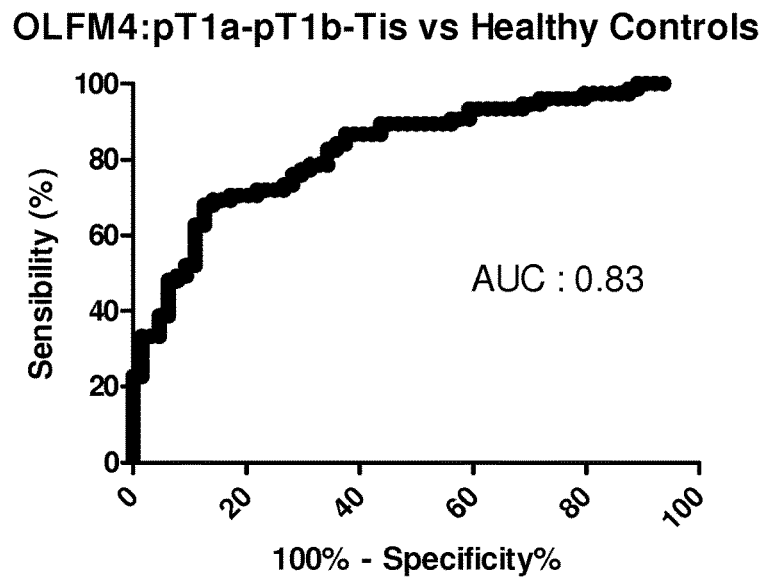
Figure 6:
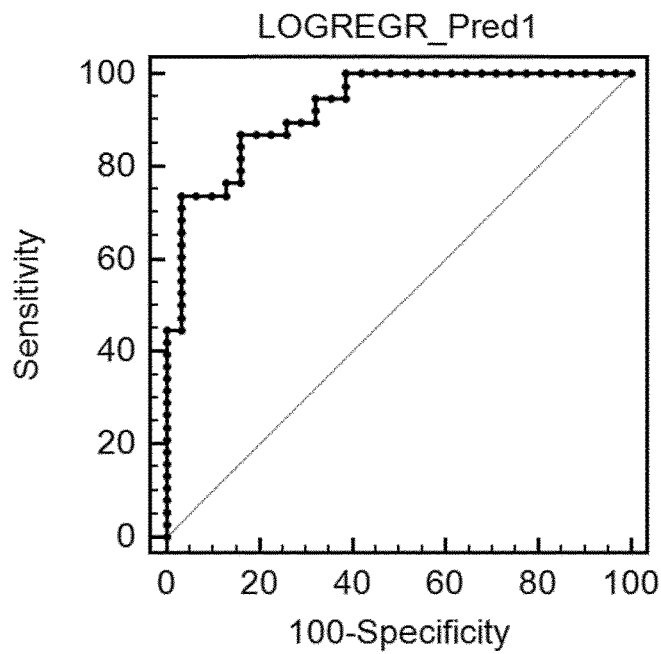

FIG. 6: OLFM4 and Low-DSP are early breast cancer biomarkers (first study)

A: Proportion of early breast cancer patients tested positive for high OLFM4 and NENF expression and low-DSP expression.

B: Expression level of circulating OLFM4 in the serum of 335 breast cancer patients and in 81 early breast cancer and in that of 65 healthy controls; the Mann-Whitney test for independent samples was used to calculate the significance of the results. OLFM4 was significantly over-expressed (p<0.0001) in the patients with early breast cancer (tumour size <1 cm).

C: ROC curve of the OLFM4 analysis to distinguish early breast cancers (n=81) from healthy controls (n=65); the AUC for patients compared to the population without cancer was 0.83 (CI 95: 0.75-0.89); the sensitivity of the test was 67%, while specificity was 87% for a concentration >40 ng/ml.

D: ROC curve obtained with the predictor combining OLFM4 and DSP. The AUC for patients was 0.92; the sensitivity of the test was 87% and the specificity was 84%.

Figure 7:
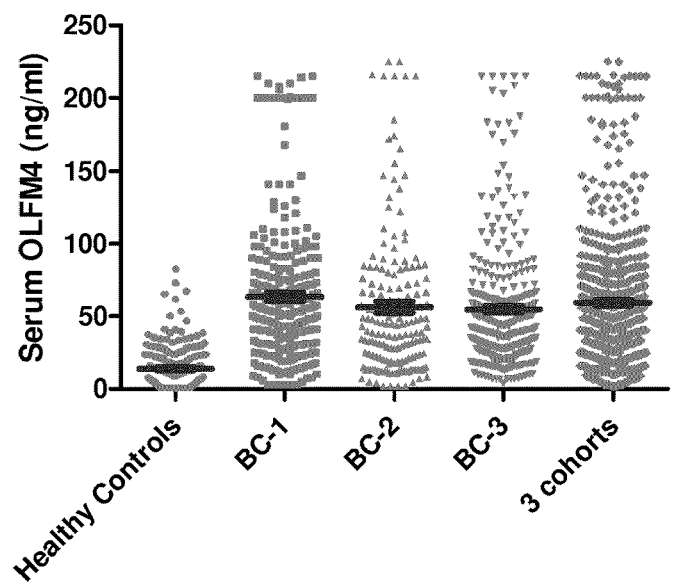
Figure 7:
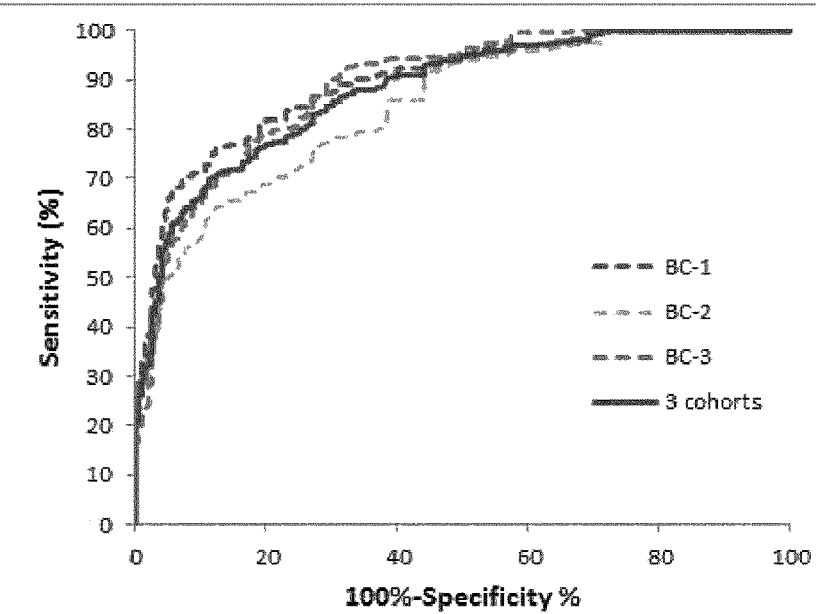
Figure 7:
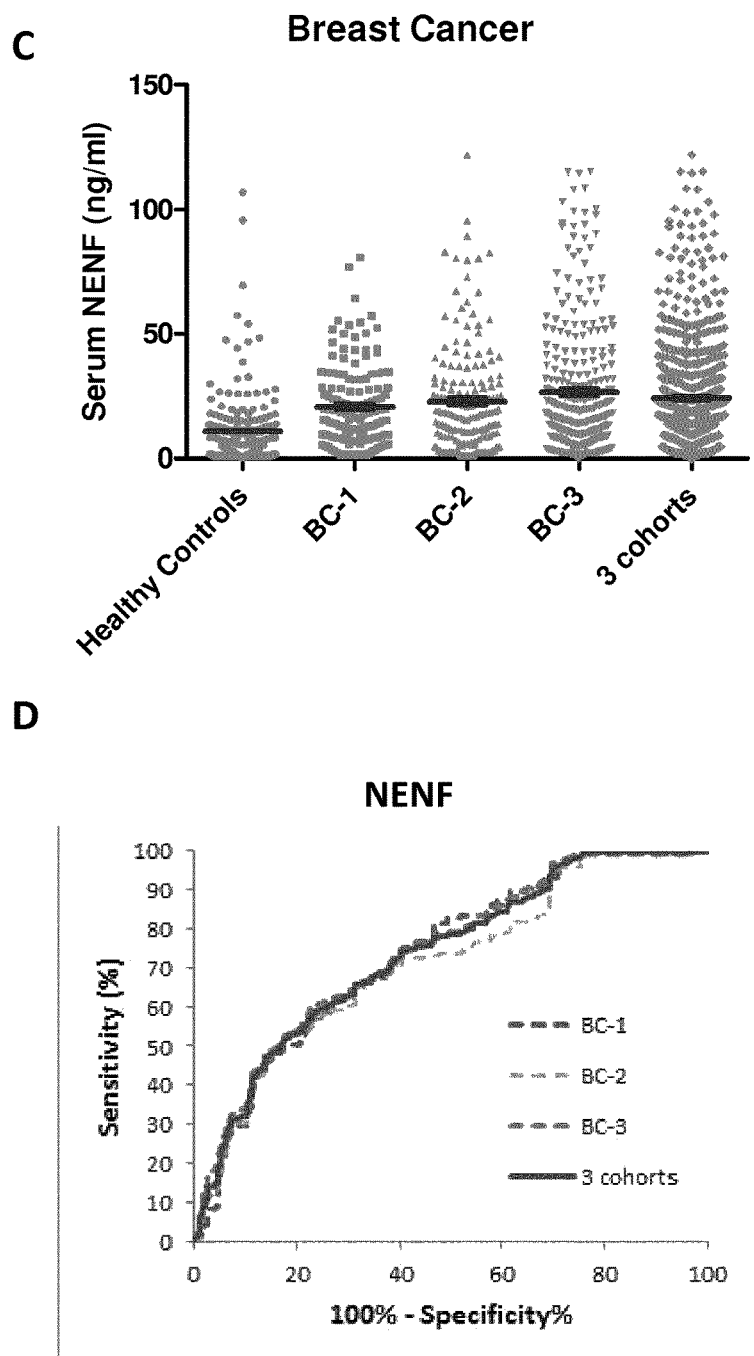
Figure 7:
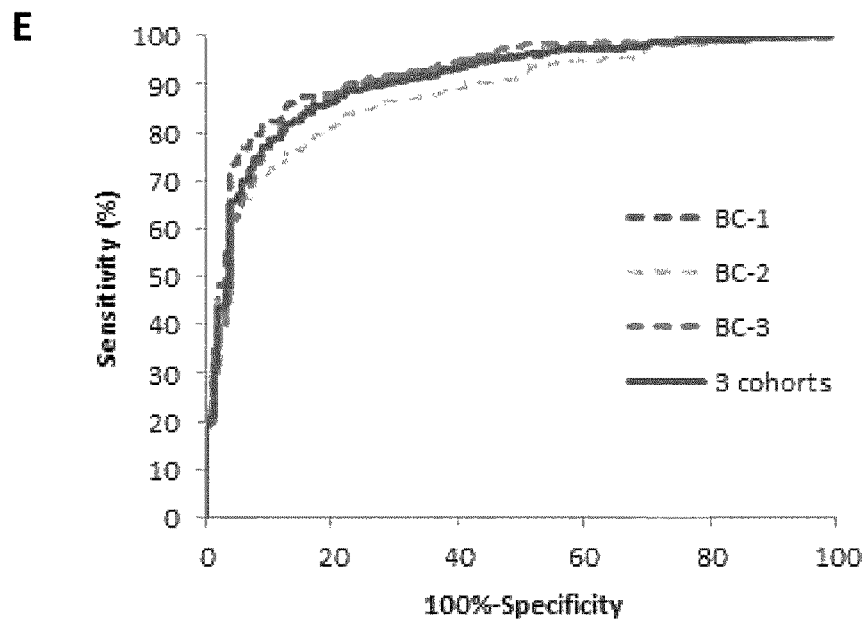
Figure 7:
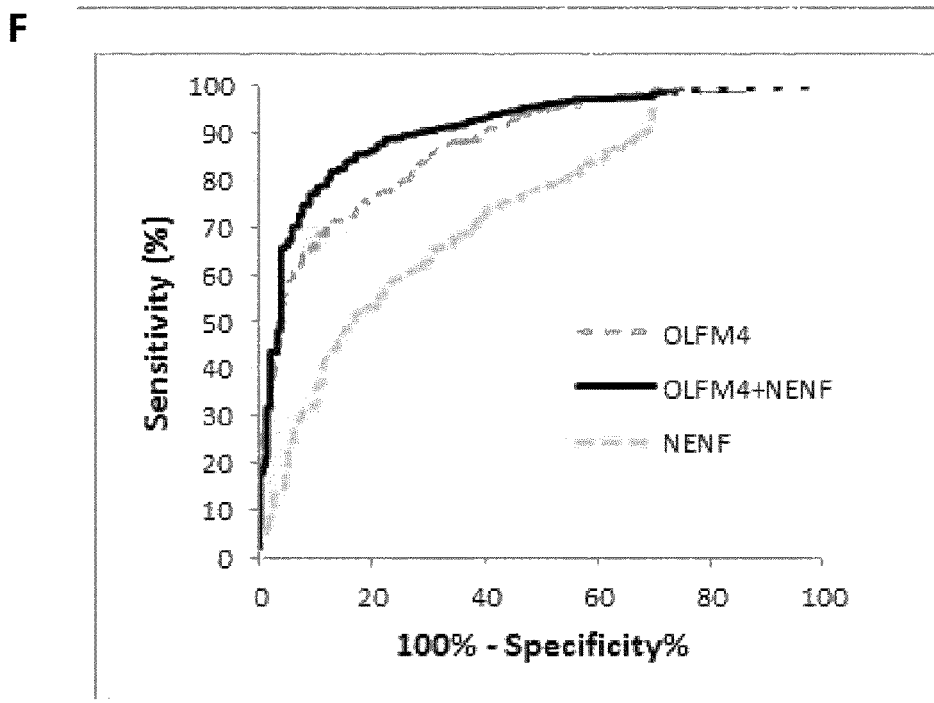

FIG. 7: Serum OLFM4 and NENF levels in breast cancer samples (second study)

A: Level of circulating olfactomedin-4 in the sera of BC-1 (test cohort, n=277), BC-2 (validation cohort-1, n=171) and BC-3 (validation cohort-2, n=318) breast cancer patients and in that of 195 healthy controls; the Mann-Whitney test for independent samples was used to calculate the significance of the results. Olfactomedin-4 was significantly over-expressed (p<0.0001) in the test cohort and in the both validation cohorts.

B: ROC curves of the Olfactomedin-4 analysis to distinguish BC-1, BC-2 and BC-3 from healthy controls; the area under the curve (AUC) for patients compared to the population without cancer was 0.89 (CI 95: 0.87-0.92) for BC-1; 0.85 (CI 95: 0.81-0.89) for BC-2; 0.89 (CI 95: 0.86-0.91) for BC-3 and 0.88 (CI 95: 0.85-0.90) for the 3 cohorts.

C: Level of circulating Neudesin in the serum of BC-1 (test cohort, n=277), BC-2 (validation cohort-1, n=171) and BC-3 (validation cohort-2, n=318) breast cancer patients and in that of 195 healthy controls; the Mann-Whitney test for independent samples was used to calculate the significance of the results. Neudesin was significantly over-expressed (p<0.0001) in the test cohort and in the both validation cohorts.

D: ROC curves of the Neudesin for BC-1, BC-2 and BC-3; the AUC for patients compared to the population without cancer was 0.74 (CI 95: 0.68-0.79) for BC-1; 0.72 (CI 95: 0.66-0.77) for BC-2; 0.74 (CI 95: 0.70-0.79) for BC-3 and 0.73 (CI 95: 0.69-0.77) for the 3 cohorts.

E: ROC curves of Olfactomedin-4+Neudesin for BC-1, BC-2 and BC-3; the AUC for patients compared to the population without cancer was 0.92 (CI 95: 0.89-0.95) for BC-1; 0.88 (CI 95: 0.84-0.92) for BC-2; 0.91 (CI 95: 0.88-0.94) for BC-3 and 0.91 (CI 95: 0.88-0.93) for the 3 cohorts.

F: ROC curves of olfactomedin-4 alone, neudesin alone and the association of the both proteins; the AUC was 0.88 (CI 95: 0.85-0.90) for olfactomedin-4 alone, 0.73 (CI 95: 0.69-0.77) for neudesin alone and 0.91 (CI 95: 0.88-0.93) for the both proteins.

Figure 8:
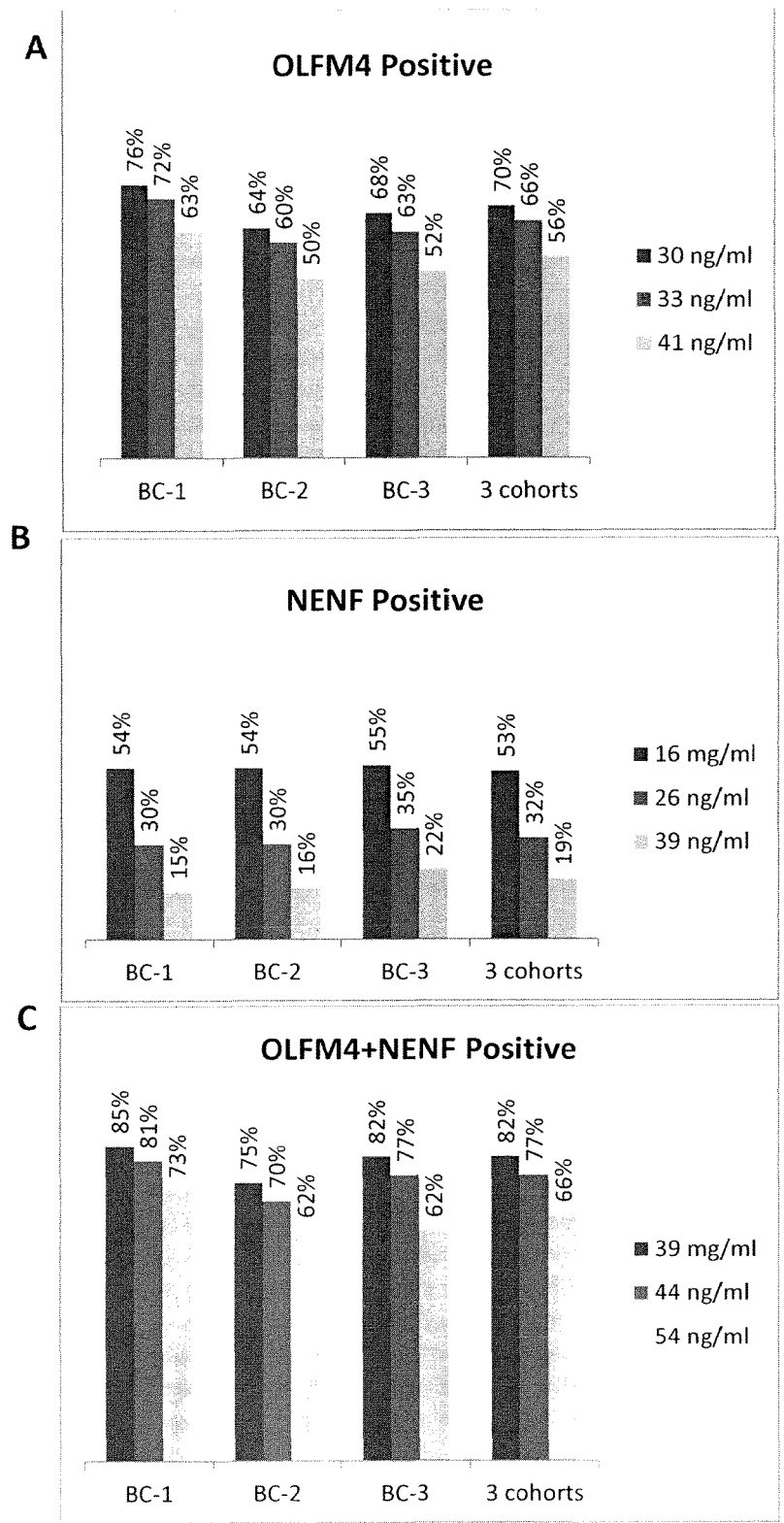

FIG. 8: OLFM4, NENF and OLFM4+NENF positive patients (second study)

Proportion of patients tested positive for the increased OFLM4 (A), NENF (B) and OLFM4+NENF (C) levels.

Figure 9:
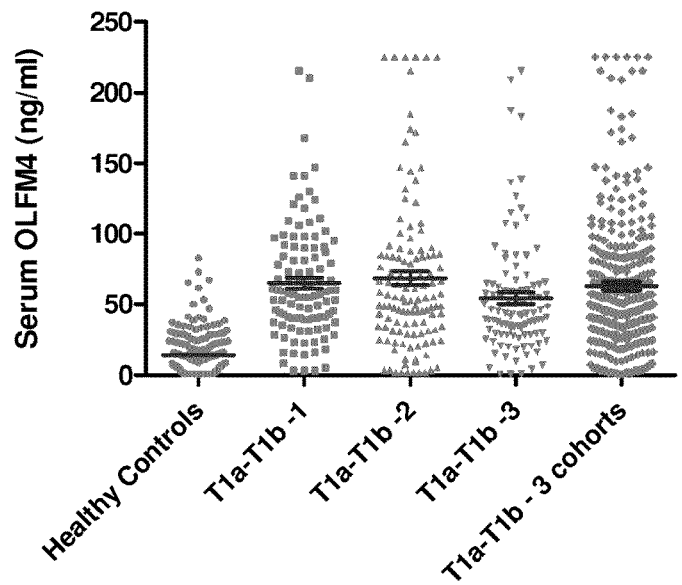
Figure 9:
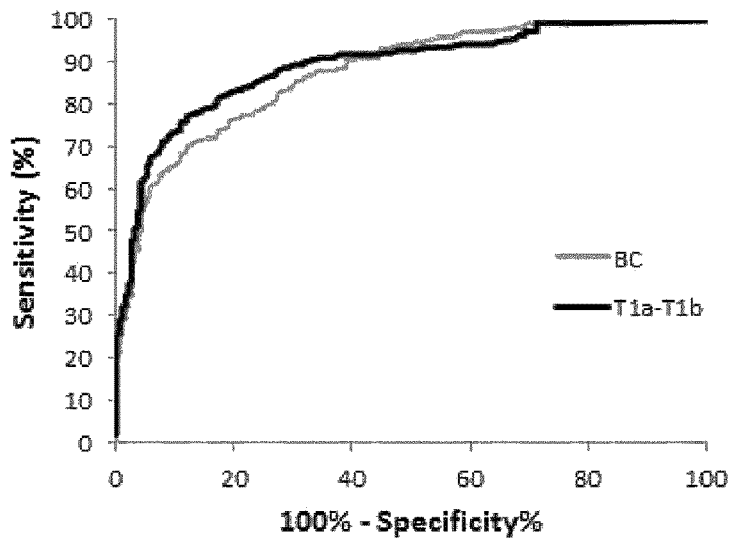
Figure 9:
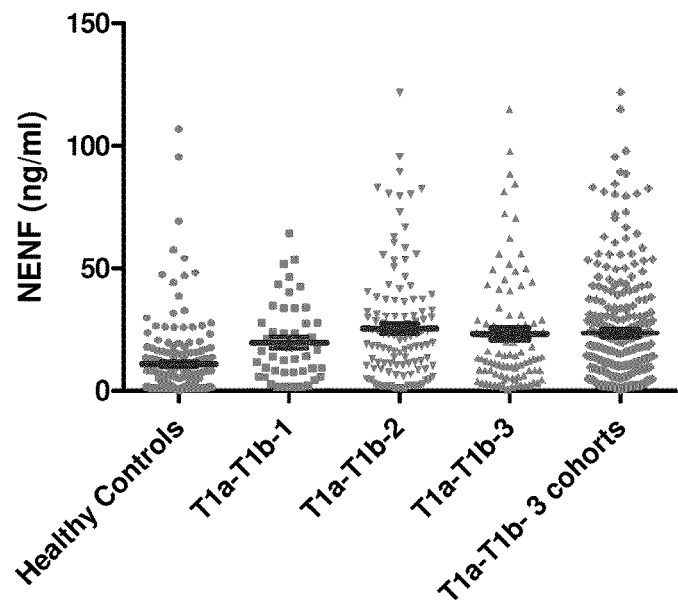
Figure 9:
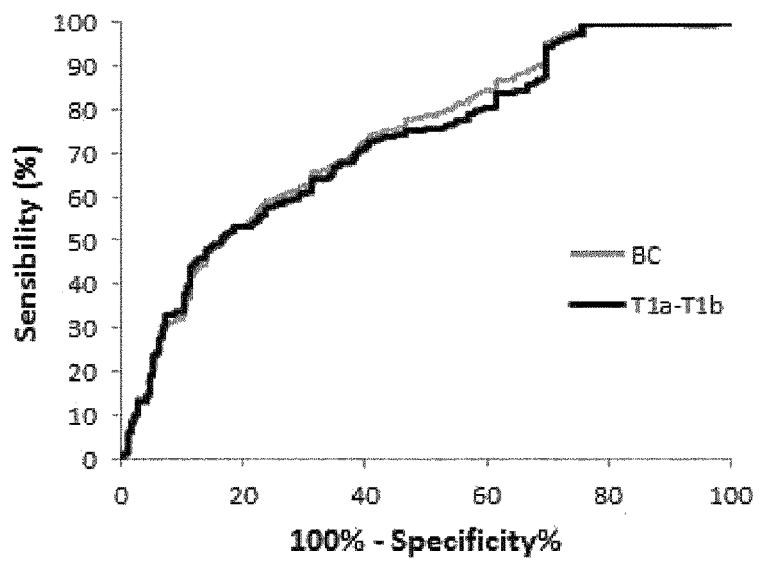

FIG. 9: Serum OLFM4 and NENF levels in sera of patients with a small tumor (<1 cm) (second study)

A: Level of circulating olfactomedin-4 in the sera of T1a-T1b-1 (test cohort, n=105), T1a-T1b-2 (validation cohort-1, n=123) and T1a-T1b-3 (validation cohort-2, n=108) patients and in that of 195 healthy controls; the Mann-Whitney test for independent samples was used to calculate the significance of the results. Olfactomedin-4 was significantly over-expressed (p<0.0001) in the test cohort and in the both validation cohorts.

B: ROC curves of OLFM4 in BC and T1a-T1b cohorts; the AUC was 0.88 (CI 95: 0.85-0.90) in BC and 0.89 (CI 95: 0.86-0.92) in T1a-T1b cohort.

C: Level of the circulating neudesin in the same cohorts. Neudesin was significantly over-expressed (p<0.0001) in the test cohort and in the both validation cohorts.

D: ROC curves of NENF in BC and T1a-T1b cohorts; the AUC was 0.73 (CI 95: 0.69-0.77) in BC and 0.72 (CI 95: 0.68-0.77) in T1a-T1b cohort.

Figure 10:
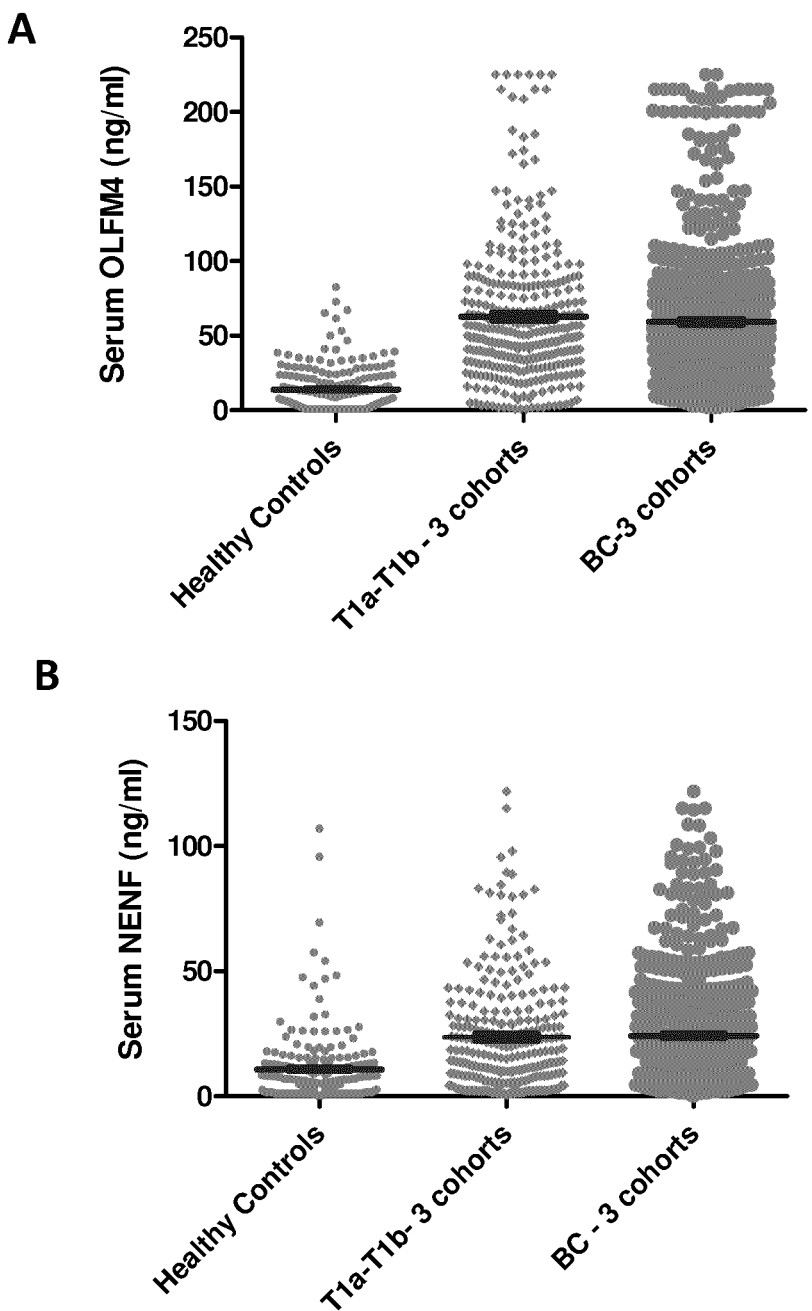
Figure 10:
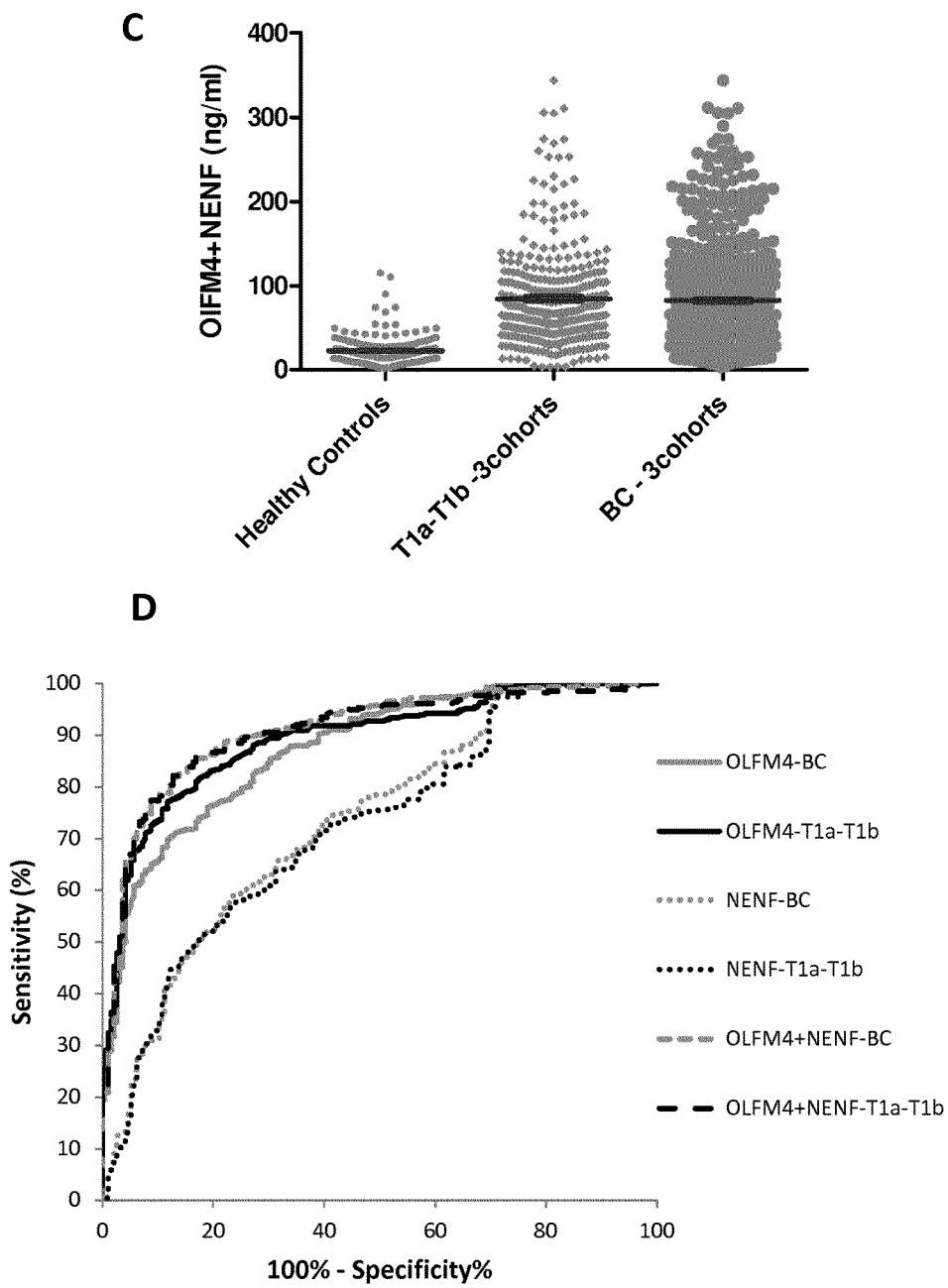

FIG. 10: OLFM4 and NENF are early breast cancer biomarkers (second study)

A: Levels of OLFM4 in sera of T1a-T1b-3 cohorts (n=336), in BC-3 cohorts (n=766) and in healthy Controls (n=195).

B: Levels of NENF in sera of T1a-T1b-3 cohorts (n=336), in BC-3 cohorts (n=766) and in healthy Controls (n=195).

C: Levels of OLFM4+NENF in sera of T1a-T1b-3 cohorts (n=336), in BC-3 cohorts (n=766) and in healthy Controls (n=195).

D: ROC curves of OLFM4, NENF and OLFM4+NENF in BC-3 cohorts and in T1a-T1b-3 cohorts.

EXAMPLES

1. Material and Methods

1.1. Patient Selection

A preliminary study was conducted on 20 healthy controls and (20-50) breast cancer serum samples of female breast cancer patients. This study aimed to evaluate the diagnostic value of potential biomarkers of breast cancer identified via proteomic mapping of a transformed breast cancer cell line and of several breast tumours.

A first study was subsequently conducted on 65 healthy controls and 335 breast cancer serum samples of female breast cancer patients. This study aimed to evaluate in more details the diagnostic values of three specific potential breast cancer biomarkers.

TABLE 2 clinical/pathological characteristics of patients with breast carcinoma (first study)

| Patient characteristics | BC-1 (n = 335) |
|---|---|
| Age (years) median [min-max] | 60 [31-90] |
| <50 (%) | 72 (21.5) |
| >=50 (%) | 263 (78.5) |
| HR | |
| negative (%) | 28 (8.3) |
| positive (%) | 307 (91.7) |
| Her2 overexpression (%) | 40 (11.9) |
| lymph node status | |
| positive (%) | 41 (12.2) |

In a second study aimed to further validate two biomarkers of the first study, sera from female breast cancer patients were collected at Institut de Cancerologie de l'Ouest (ICO) Paul Papin in Angers for the first cohort, at ICO René Gauducheau in Nantes for the second cohort and at ICO Paul Papin in Angers for the third cohort. The first population set consisted of 277 subjects (BC-1) among which 105 women had a small tumour <1 cm (T1ab-1); the second population set consisted of 171 individuals with 123 (BC-2) women with a small tumour <1 cm (T1ab-2); the third cohort consisted of 318 women (BC-3) among which 108 had a small tumor <1 cm (T1ab-3) (see their characteristics in Table 3 below). A total of 195 healthy controls from Etablissement Français du Sang were also evaluated.

TABLE 3 clinical/pathological characteristics of patients with breast carcinoma (second study)

| Patient characteristics | BC-1 (n = 277) | BC-2 (n = 171) | BC-3 (n = 318) |
|---|---|---|---|
| Age (years) median [min-max] | 60 [31-87] | 61 [33-91] | 58 [19-90] |
| <50 (%) | 60 (21.6) | 31 (18.1) | 81 (25.5) |
| >=50 (%) | 217 (78.4) | 140 (81.9) | 237 (74.5) |
| HR | | | |
| negative (%) | 23 (8.3) | 7 (4.1) | 29 (9.1) |
| positive (%) | 254 (91.7) | 164 (95.9) | 289 (90.9) |
| Her2 overexpression (%) | 33 (11.9) | 19 (11.1) | 41 (12.9) |
| lymph node status | | | |
| positive (%) | 33 (11.9) | 19 (11.1) | 41 (12.9) |
| T1a-T1b (<1 cm) | 105 | 123 | 108 |
| | T1ab-1 (n = 105) | T1ab-2 (n = 123) | T1ab-3 (n = 108) |
| Age (years) median [min-max] | 61 [34-84] | 63 [36-90] | 60 [37-84] |
| <50 (%) | 19 (18.1) | 17 (13.8) | 18 (16.6) |
| >=50 (%) | 86 (81.9) | 106 (86.2) | 90 (83.4) |
| HR | | | |
| negative (%) | 7 (6.7) | 5 (4.0) | 9 (8.3) |
| positive (%) | 98 (93.3) | 118 (96.0) | 99 (91.7) |
| Her2 overexpression (%) | 12 (11.4) | 7 (5.7) | 12 (11.1) |
| lymph node status | | | |
| positive (%) | 12 (11.4) | 6 (4.9) | 15 (13.9) |

In each study, all sera were collected after obtaining written informed consent. The study protocol was approved by the Institutional Review Board. All samples were collected, processed and stored in a similar fashion. Briefly, blood sample was centrifuged at 3500 rpm for 10 minutes, and the serum was stored at −80° C. All sera were obtained prior to surgery or neoadjuvant treatment.

1.2. Cell Culture

The human breast epithelial cell lines MCF10A LXSN (MCF10A) (non-tumorigenic breast epithelial cell line, expressing a control empty vector) and MCF10A KRASV12 (MCF10A-RAS, which is a tumorigenic breast epithelial cell line) were obtained by retroviral infection as previously described (Konishi et al., 2007). They were kindly provided by Dr Ben Ho'Park. MCF10A LXSN and MCF10A KRASVI2 cell lines were grown in DMEM/F12 (1:1) (Life Technologies) supplemented with 50 mM Hepes, 5% donor horse serum (DHS; Eurobio), 1% L-Glutamin, 20 ng/mL EGF (Peprotech), 10 μg/mL insulin, 0.5 μg/mL hydrocortisone, and 0.1 μg/mL cholera toxin. All supplements were purchased from Sigma-Aldrich unless otherwise noted. Cells were harvested using Trypsin EDTA, enzyme reaction were stopped with 2 volumes of supplemented DMEM/F12 medium, cells were washed twice with PBS and dried cell pellets were frozen.

1.3. Protein Extraction from the MCF10A and MCF10A-RAS Breast Epithelial Cell Lines Approximately $5 \times 10^6$ cells were lysed in 0.6 ml of 4% SDS and 0.1 M DTT in 0.1 M Tris-HCl, pH 7.6 at room temperature for 30 min and briefly sonicated to reduce viscosity of the lysate. Detergent was removed from the lysates and the proteins were digested with trypsin according to the FASP protocol (Wiśniewski et al., 2009) using spin ultrafiltration units of nominal molecular weight cut of 30 000 Daltons. Briefly, the protein lysate was applied to an YM-30 microcon filter units (Cat No. MRCFOR030, Millipore) spun down and washed three times with 200 μL of 8 M urea in 0.1 M Tris/HCl, pH 8.5. Then 6 μL of 200 mM MMTS in 8 M urea was added to the filters and the samples were incubated for 20 min. Filters were washed thrice with 200 μL of 8 M urea in 0.1 M Tris/HCl, pH 8.5, followed by six washes with 100 μL 0.5M TEAB. Finally, trypsin (AB sciex) was added in 100 μL 0.5M TEAB to each filter. The protein to enzyme ratio was 100:1. Samples were incubated overnight at 37° C. and released peptides were collected by centrifugation. Samples were then dried completely using a Speed-Vac and re-suspended in 100 μl of 0.5% trifluoroacetic acid (TFA) in 5% acetonitrile, and desalted via PepClean C-18 spin columns (Pierce Biotechnology, Rockford, Ill.). Peptide content was determined using a Micro BCA Protein Assay Kit (Pierce-Thermo Scientific, Rockford, Ill.).

1.4. Protein Extraction from Frozen Tissues (Breast Tumors and Healthy Breast Tissues)

Frozen sections (12 μm thick) of breast tumors or normal breast area were cut on a cryostat (Bright Instrument Co Ltd, St Margarets Way, UK). Specific sections were stained with toluidine blue for visual reference. To take into account tumor heterogeneity, ten frozen sections per tumor of luminal A, Her-2 overexpressed and triple-negative breast tumors were lysed in a buffer consisting of 0.1 M Tris-HCl, pH 8.0, 0.1 M DTT, and 4% SDS at 95° C. for 90 min. Detergent was removed from the lysates and the proteins were digested with trypsin according to the FASP protocol (Wiśniewski et al., 2009) using spin ultrafiltration units of nominal molecular weight cut of 30 000 Daltons. To YM-30 microcon filter units (Cat No. MRCFOR030, Millipore) containing protein concentrates, 200 μL of 8 M urea in 0.1 M Tris/HCl, pH 8.5 (UA), was added and samples were centrifuged at 14 000 g at 20 C for 8 min. This step was performed thrice. Then 6 μL of 200 mM MMTS in 8 M urea was added to the filters and the samples were incubated for 20 min. Filters were washed thrice with 200 μL of 8 M UA followed by six washes with 100 μL 0.5M TEAB. Finally, trypsin (AB sciex) was added in 100 μL 0.5M TEAB to each filter. The protein to enzyme ratio was 100:1. Samples were incubated overnight at 37° C. and released peptides were collected by centrifugation. Samples were then dried completely using a Speed-Vac and re-suspended in 100 μl of 0.5% trifluoroacetic acid (TFA) in 5% acetonitrile, and were desalted via PepClean C-18 spin columns (Pierce Biotechnology, Rockford, Ill.). Peptide content was determined using Micro BCA Protein Assay Kit (Pierce-Thermo Scientific, Rockford, Ill.).

1.5. Peptide Labelling with iTRAQ Reagents

For the iTRAQ labelling, 100 pg of each peptide solution was labelled at room temperature for 2 h with one iTRAQ reagent vial previously reconstituted with 70 μl of ethanol for 4plex iTRAQ reagent. Labelled peptides were subsequently mixed in a 1:1:1:1 ratio and dried completely using a Speed-Vac.

1.6. Peptide OFFGEL Fractionation

For pI-based peptide separation, the 3100 OFFGEL Fractionator (Agilent Technologies, Boblingen, Germany) was used with a 12 or 24-well set-up using the following protocol. First, samples were desalted onto a Sep-Pak C18 cartridge (Waters). For the 24-well set-up, peptide samples were diluted in the OFFGEL peptide sample solution to a final volume of 3.6 mL. Then, the IPG gel strip of 24 cm-long (GE Healthcare, Munchen, Germany) with a 3-10 linear pH range was rehydrated with the Peptide IPG Strip Rehydradation Solution, according to the protocol of the manufacturer, for 15 min. 150 μL of sample was loaded in each well. Electrofocusing of the peptides was performed at 20° C. and 50 μA until the 50 kVh level was reached. After focusing, the 24 peptide fractions were withdrawn and the wells were washed with 200 μL of a solution of water/methanol/formic acid (49/50/1). After 15 min, each washing solution was pooled with its corresponding peptide fraction. All fractions were evaporated by centrifugation under vacuum and maintained at −20° C. For the 2D-OFFGEL approach, the peptides were first fractionated in 12 fractions in the pH range 3-10. Then, fractions F1-F2, fraction F3 to F8 and fractions F9 to F12 were pooled and refractionated in 24 fractions in the pH range 3.5-4.5, 4-7 and 6-9, respectively. 72 fractions were obtained which were subsequently analysed by nanoLC-MS/MS.

1.7. Capillary LC Separation

Juste before nano-LC analysis, each fraction was resuspended in 20 μL of $H_2O$ with 0.1% (v/v) TFA. The samples were separated on an Ultimate 3,000 nano-LC system (Dionex, Sunnyvale, USA) using a C18 column (PepMap100, 3 μm, 100 A, 75 μm id×15 cm, Dionex) at 300 nL/min a flow rate. Buffer A was 2% ACN in water with 0.05% TFA and buffer B was 80% ACN in water with 0.04% TFA. Peptides were desalted for 3 min using only buffer A on the precolumn, followed by a separation for 105 min using the following gradient: 0 to 20% B in 10 min, 20% to 45% B in 85 min and 45% to 100% B in 10 min. Chromatograms were recorded at the wavelength of 214 nm. Peptide fractions were collected using a Probot microfraction collector (Dionex). CHCA (LaserBioLabs, Sophia-Antipolis, France) was used as MALDI matrix. The matrix (concentration of 2 mg/mL in 70% ACN in water with 0.1% TFA) was continuously added to the column effluent via a micro "T" mixing piece at 1.2 μL/min flow rate. After 12 min run, a start signal was sent to the Probot to initiate fractionation. Fractions were collected for 10 sec and spotted on a MALDI sample plate (1,664 spots per plate, ABsciex, Foster City, Calif.).

1.8. MALDI-MS/MS

MS and MS/MS analyses of off-line spotted peptide samples were performed using the 5800 MALDI-TOF/TOF Analyser (ABsciex) and 4000 Series Explorer software, version 4.0. The instrument was operated in positive ion mode and externally calibrated using a mass calibration standard kit (ABsciex). The laser power was set between 2800 and 3400 for MS and between 3600 and 4200 for MS/MS acquisition. After screening all LC-MALDI sample positions in MS-positive reflector mode using 2000 laser shots, the fragmentation of automatically-selected precursors was performed at a collision energy of 1 kV using air as collision gas (pressure of ~2×10-6 Torr) with an accumulation of 3000 shots for each spectrum. MS spectra were acquired between m/z 1000 and 4000. The parent ion of Glu1-fibrinopeptide was used at m/z 1570.677 diluted in the matrix (30 femtomoles per spot) for internal calibration. Up to 12 of the most intense ion signals per spot position having a S/N >20 were selected as precursors for MS/MS acquisition. The identification of peptides and proteins was performed by the ProteinPilot™ Software V 4.0 (AB Sciex) using the Paragon algorithm as the search engine (Shilov et al., 2007). Each MS/MS spectrum was searched for *Homo sapiens* species against the Uniprot/swissprot database (UniProtKB/Sprot 20110208 release 01, with 525997 sequence entries). The searches were run using the fixed modification of methylmethanethiosulfate labeled cysteine parameter enabled. Other parameters, such as tryptic cleavage specificity, precursor ion mass accuracy and fragment ion mass accuracy, were MALDI 5800 built-in functions of Protein-Pilot software. The detected protein threshold (unused protscore (confidence)) in the software was set to 1.3 to achieve 95% confidence, and identified proteins were grouped by the ProGroup algorithm (ABsciex) to minimize redundancy. The bias correction option was executed.

To estimate the false discovery rate (FDR), a decoy database search strategy was used. The FDR is defined as the percentage of decoy proteins identified against the total protein identification. The FDR was calculated by searching the spectral against the Uniprot *Homo sapiens* decoy database.

1.9. ELISA Tests

Commercially available ELISA kits from USCN Life Science Inc. or R&D were used to assay concentrations of OLFM4, NENF and DSP. The kits consisted of 96-well microtiter plates coated with antibody specific to each type of molecule, detection antibodies for identifying the antibody-protein in the plate by streptavidin-biotin labeling and TMB substrate which generated colored product. The sample was added and assay was conducted according to the manufacturer's instructions. The absorbance of the colored product developed at the end of the assay was quantified at wavelength 450 nm on ELISA reader (Tecan Magellan Sunrise).

1.10. Statistical Quantification of Relative Protein Expression

For the quantification of the relative protein expression the customized software package iQuantitator (Schwacke et al., 2009; Grant et al., 2009) as well as the softwares TANAGRA (V1.4) and GraphPad Prism 5 were used to infer the magnitude of change in protein expression. Those software infer treatment-dependent changes in expression using Bayesian statistical methods, more specifically, the Mann-Whitney test for independent samples, and receiver-operating-characteristic (ROC) curves. Basically, this approach was used to generate means, medians, the area under the ROC curve (AUC), and 95% confidence intervals (upper and lower) to test the hypothesis that the AUC was superior to 0.5 for each treatment-dependent change in protein expression by using peptide-level data for each component peptide.

For proteins whose iTRAQ ratios were downregulated, the extent of down-regulation was considered further if the higher limit of the credible interval had a value lower than 1. Conversely, for proteins whose iTRAQ ratios were increased, the extent of upregulation was considered further if the lower limit of the confidence interval had a value greater than 1. The width of these confidence intervals depended on the data available for a given protein. The iQuantitator software took into consideration all the peptides observed and the number of spectra used to quantify the change in expression for a given protein. In these conditions, it was possible to detect small but significant changes in up- or down-regulation when many peptides were available. The peptide selection criteria for relative quantification were performed as follows. Only peptides unique for a given protein were considered for relative quantification, excluding those common to other isoforms or proteins of the same family. Proteins were identified on the basis of having at least two peptides with an ion score above 95% confidence.

2. Results

Figure 1:
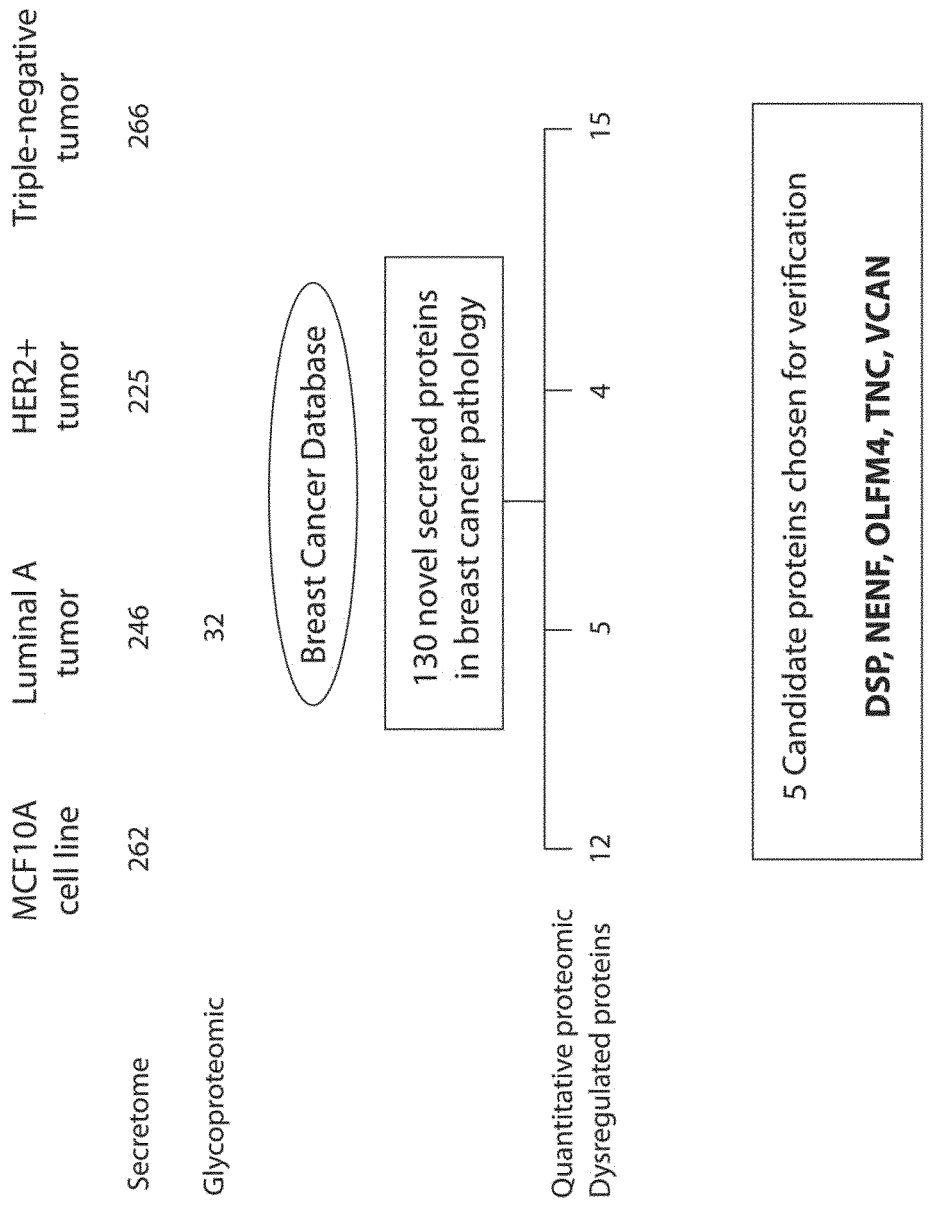
FIG. 1: Scoring system for selection of candidate breast cancer biomarkers

The strategy used to identify new candidate biomarkers for breast tumours is summarised in FIG. 1. Firstly, the inventors drew up a proteomic map of a transformed breast cell line using several breast tumours with different statuses in order to establish the most exhaustive list possible of the proteins that characterise breast tumours. This list was compared against the list of secreted proteins that have already been identified in human blood (Schenk et al., 2008; Cao et al., 2013; HUPO Plasma Proteome Project website http://www.ccmb.med.umich.edu/PPP) then was examined on the "Breast cancer database" (http://www.itb.cnr.it/breastcancer/) so that only the novel secreted proteins in breast cancer pathology were selected.

2.1. Proteomic Analysis of the MCF10A and MCF10A-RAS Cell Lines (Imbalzano et al., 2013)

Using the two-step OFFGEL approach, the inventors mapped the proteome of the non-transformed breast cell line (MCF10A), as well as that of this same cell line transformed with the KRAS oncogene in order to mimic oncogenic activation and abnormal survival. Although mutations in the RAS gene are not common in breast cancers, the RAS pathway is activated in this disease by overexpression of growth factor receptors signaling such as the ErbB2 receptor, which is activated in 30% of breast cancers. RAS-induced breast tumors are characterized by activation of mitogen-activated protein kinase signaling which is well known to be associated with early neoplasia and poor prognosis. Using the proteomic approach described herein, 2152 proteins with at least two peptides were identified. Out of these proteins, 262 were found in the secreted proteins databases (data not shown).

2.2. Proteomic Analysis of Luminal a Breast Tumours

Through a similar proteomic mapping of luminal A breast tumours, the inventors were able to identify 1093 proteins with at least two peptides. Out of these proteins, 246 were secreted proteins (data not shown).

2.3. Proteomic Analysis of Breast Tumours Expressing HER2

Through a similar proteomic mapping of breast tumours with HER2 receptor overexpression, the inventors were able to identify 624 proteins with at least two peptides. Out of these proteins, 225 were secreted proteins (data not shown).

2.4. Proteomic Analysis of Triple-negative Breast Tumours

Through a similar proteomic mapping of triple negative breast tumours, the inventors identified 2407 proteins with at least two peptides. Out of these proteins, 266 were secreted proteins (data not shown).

2.5. Comparative Proteomic Analysis

A comparison of all the identified secreted proteins in the MCF10A-RAS cell line, as well as in luminal A, HER2 positive and triple-negative breast tumors against the "Breast cancer database" (http://www.itb.cnr.it/breastcancer/) allowed to select 125 novel proteins in breast cancer pathology in the first study, of which 121 were validated in the second study (data not shown).

2.6. Dysregulated New Secreted Proteins in the Transformed MCF10A Cell Line Transformed by the KRAS Oncogene (MCF10-RAS)

Comparing the list of the 121 secreted proteins against the list of significantly dysregulated proteins in the MCF10A cell line transformed by the KRAS oncogene, 12 proteins were identified (Table 4). Seven were under-expressed (DSP, JUP, ACTN1, CTNNA1, METTL13, HSPD1 and GSTP1) and five were over-expressed (COPA, TLN1, PYGB, HPCAL1 and IGF2R).

TABLE 4

Dysregulated secreted proteins in the MCF10A cell line transformed by the KRAS oncogene

| Symbol | Accession # | Full Name of the Biomarker | iTRAQ ratio |
|---|---|---|---|
| DSP | sp\|P15924\|DESP_HUMAN | Desmoplakin | 0.0413 |
| JUP | sp\|P14923\|PLAK_HUMAN | Junction plakoglobin | 0.0643 |
| ACTN1 | sp\|P12814\|ACTN1_HUMAN | Alpha-actinin-1 | 0.2559 |
| CTNNA1 | sp\|P35221\|CTNA1_HUMAN | Catenin alpha-1 | 0.2606 |
| METTL13 | sp\|Q8N6R0\|MTL13_HUMAN | Methyltransferase-like protein 13 | 0.6668 |
| HSPD1 | sp\|P10809\|CH60_HUMAN | 60 kDa heat shock protein, mitochondrial | 0.6792 |
| GSTP1 | sp\|P09211\|GSTP1_HUMAN | Glutathione S-transferase P | 0.879 |
| COPA | sp\|P53621\|COPA_HUMAN | Coatomer subunit alpha | 3.4995 |
| TLN1 | sp\|Q9Y490\|TLN1_HUMAN | Talin-1 | 5.7016 |
| PYGB | sp\|P11216\|PYGB_HUMAN | Glycogen phosphorylase, brain form | 8.4723 |
| HPCAL1 | sp\|P37235\|HPCL1_HUMAN | Hippocalcin-like protein 1 | 11.3763 |
| IGF2R | sp\|P11717\|MPRI_HUMAN | Cation-independent mannose-6-phosphate receptor | 17.5388 |

2.7. Dysregulated New Secreted Proteins in Triple-negative Tumours

Comparing the list of the 121 secreted proteins against the list of significantly dysregulated proteins in the triple-negative tumours, 15 proteins were identified. Two were down-regulated (APOH and CFH) and 13 were over-expressed (CMPK1, ALDOA, COPA, DDT, CFL1, GSTO1, ARF1, COTL1, FTL, DSTN, DSP, ACTN1, TNC) (Table 5).

TABLE 5

Dysregulated secreted proteins in triple-negative tumours

| Symbol | Full name of the biomarker | iTRAQ ratio |
|---|---|---|
| APOH | Beta-2-glycoprotein 1 | 0.602 |
| CFH | Complement factor | 0.693 |
| CMPK1 | UMP-CMP kinase | 1.332 |
| ALDOA | Fructose-bisphosphate aldolase A | 1.37 |
| COPA | Coatomer subunit alpha | 1.496 |
| DDT | D-dopachrome decarboxylase | 1.504 |
| CFL1 | Cofilin-1 | 1.569 |
| GSTO1 | Glutathione S-transferase omega-1 | 1.586 |
| ARF1 | ADP-ribosylation factor 1 | 1.624 |
| COTL1 | Coactosin-like protein | 1.703 |
| FTL | Ferritin light chain | 1.743 |
| DSTN | Destrin | 1.978 |
| DSP | Desmoplakin | 2.119 |
| ACTN1 | Alpha-actinin-1 | 2.196 |
| TNC | Tenascin | 1.616 |

2.8. Dysregulated New Secreted Proteins in a HER2+ Tumour Compared to the Healthy Tissue Comparing the proteome of dysregulated proteins against the list of the 125 proteins, five proteins were characterised; one under-expressed protein (CFH) and four over-expressed proteins (ANXA2, FTL, TAGLN2, TNC) (Table 6).

TABLE 6

Dysregulated secreted proteins in HER2+ tumour

| Symbol | Full name of the biomarker | iTRAQ ratio |
|---|---|---|
| ANXA2 | Annexin A2 | 3.1623 |
| CFH | Complement factor H | 0.0474 |
| FTL | Ferritin light chain | 20.7014 |
| TAGLN2 | Transgelin-2 | 14.5881 |
| TNC | Tenascin | 9.6383 |

2.9. Glycoproteomic Analysis

The purpose of this analysis was to complete the sub-proteome of secreted proteins. Using three breast tumours, the inventors established a glycoproteome. Using this glycoproteome, 5 secreted proteins (HPX, OLFM4, OLFML3, TNC, VCAN) that have never been studied as breast cancer biomarkers were characterized.

2.10. Selection of Candidate Biomarkers

The inventors employed a systematic scoring system to segregate 5 candidates: DSP, NENF, OLFM4, TNC, VCAN.

2.11. Candidate Validation in Breast Cancer Patients

A preliminary verification was performed on 20 healthy controls and (20-50) breast cancer serum samples. The concentration medians for TNC and VCAN cancer samples were not significantly ($p>0.05$) different from those of healthy controls. The concentration medians for OLFM4 and NENF were 2.2 and 3.1-fold higher than healthy controls sera, respectively, with p-value <0.005. The concentration median for DSP breast cancer samples was not significantly different from those of healthy controls but a significant difference (p-value<0.032) between healthy controls samples and small tumors group (size<2 cm, pT1) was identified (FIG. 2). In this case, DSP concentration was lower than in the control group. Conversely, among the 50 breast cancer samples, 3 overexpressed DSP samples were found which matched with 3 recurrent breast tumors.

2.12. OLFM4 and NENF Elevation in Breast Cancer Sera

To further evaluate the potential of OLFM4 and NENF as serum breast cancer biomarkers, their serum concentrations were determined in a first study based on 65 healthy subjects and in 335 with breast cancer. OLFM4 and NENF were found to be significantly elevated (p<0.0001) in breast cancer sera (regardless of the grade of the tumor) compared to healthy sera (FIGS. 3A and B). The OLFM4 and NENF serum concentration was then combined for each patient (n=335) and this value was compared to that obtained in healthy controls sera: it was found that OLFM4+NENF concentration was significantly elevated (p<0.0001) in breast cancer sera (FIG. 3C).

In a second validation study, 766 participants were divided in 3 independent cohorts: BC-1 recruited in the Angers ICO Cancer Canter, BC-2 recruited in the Nantes ICO Cancer Canter and BC-3 recruited in the Angers ICO Cancer Center. The concentrations of both markers were also determined in 195 healthy subjects. For the control cohort, the OLFM4 median concentration was 9.96 ng/ml (IQR 1.00-21.94) and for NENF, the median concentration was 6.77 ng/ml (IQR 1.46-13.14). The median concentrations for OLFM4 and NENF were found to be significantly elevated (p<0.0001) in breast cancer sera as compared to healthy samples (FIGS. 7A and 7C); the values did not significantly differ between the three cohorts. When the 3 independent breast cancer sera cohorts were combined, OLFM4 median concentration of 47.00 ng/ml (IQR 25.00-75.00) and a NENF median concentration of 16.82 ng/ml (IQR 8.05-31.69) were determined.

ROC curves showed that the optimum diagnostic cutoff for OLFM4 was 29.8, 30.0 and 29.4 ng/ml for BC-1, BC-2 and BC-3 respectively. The optimum cutoff value for NENF was 13.8, 15.6 and 13.8 ng/ml for BC-1, BC-2 and BC-3, respectively. When the 3 cohorts were combined (FIGS. 7B and 7D), the optimum diagnostic values were 30.6 and 15.6 ng/ml for OLFM4 and NENF, respectively. These values were very similar to those obtained for each independent cohorts, the cutoff values in this study were chosen to be 31 ng/ml for OLFM4 and 16 ng/ml for NENF (Table 7). With these cutoff values, the sensitivity was ranging from 64 to 78% for OLFM4 and from 52% to 60% for NENF.

In order to develop a specific test, the cutoff value at 90 and 95% specificity were calculated:

for OLFM4, with 90% specificity, the cutoff value reached 33.9 ng/ml in the three independent cohorts and in the total cohort with a sensitivity ranging from 57 to 71%; with 95% specificity, the cutoff value rose to 41 or 42 ng/ml with a sensitivity from 49 to 63% (Table 7);

for NENF, with 90% specificity, the cutoff value reached 13.8 or 15.6 ng/ml for the different cohorts with a sensitivity ranging from 53 to 60% and with 95% specificity, the cutoff value rose to 39 ng/ml with a sensitivity from 14 to 22% (Table 7).

To test if these markers were complementary, the combined markers OLFM4 and NENF were estimated by binary logistic regression and the values of this function was used as one marker and subjected to ROC analysis. The values corresponding to the addition of the Elisa concentrations of OLFM4 and NENF in the same serum were also tested and the ROC curves were as exhibited as equivalent (data not shown). So, when combining the OLFM4 and NENF Elisa concentrations, ROC curves showed that the optimum diagnostic cutoff was 38.3 or 38.4 ng/ml in the three independent cohorts or in the combined cohort with a specificity of 87% and a sensitivity ranging from 75 to 85% (FIG. 7E).

When the ROC curves were compared, the AUC for OLFM4+NENF and OLFM4 alone appeared to be very close (FIG. 7F). The proportion of patients who were positive to OLFM4, NENF and OLFM4+NENF were compared in the different specificity conditions (FIG. 8). For OLFM4, the proportion of positive patients appeared to be higher in the test cohort (BC-1). Through the 3 cohorts, a proportion of positive patients of 70% for the optimum cutoff, and 66% and 56% of positive patients at 90% and 95% specificity, respectively (FIG. 8A). For NENF, the proportions of positive patients was quite similar in the 3 cohorts and an average of 53% of positive patients were reached at the optimum cutoff, and 32% and 19% were reached for 90% and 95% specificity, respectively (FIG. 8B). When the two markers were combined, it appeared that, in the test cohort and in the validation cohort 2 (BC-2), more than 80% of patients were positive (75% for the BC-2 cohort), at the optimum cutoff value. When the proportion at 90% specificity was evaluated, between 70 to 81% of positive patients were still reached. At 95% specificity, between 62 to 73 patients were OLFM4+NENF positive (FIG. 8C). The proportion of patients who were positive for OLFM4 at the optimum cutoff (31 ng/ml) was 70% and this proportion reached 81% when the two markers were combined (at the optimum cutoff 39 ng/ml, FIGS. 8A and 8C). The number of OLFM4+NENF positive patients was superior to 10% at least for each specificity values, comparing the proportion of OLFM4 alone positive patient.

TABLE 7

Area under the ROC curve, sensitivity and specificity values for diagnostic tests based on OFLM4, NENF or OLFM4 + NENF (second study)

| | AUC (95% CI) | Sensitivity (%) | Specificity (%) | cutoff (ng/ml) | 90% Specificity | | 95% Specificity | |
| --- | --- | --- | --- | --- | --- | --- | --- | --- |
| | | | | | Sensitivity (%) (95% CI) | cutoff (ng/ml) | Sensitivity (%) (95% CI) | cutoff (ng/ml) |
| BC-1 | | | | | | | | |
| OLFM4 | 0.8945 | 76.5 | 87.7 | 29.8 | 71.5 | 33.9 | 63.54 | 40.9 |
| NENF | 0.7367 | 57.24 | 76.92 | 13.8 | 29.66 | 25.9 | 14.48 | 38.4 |
| OLFM4 + NENF | 0.9188 | 85.6 | 87.3 | 38.3 | 81.48 | 43.5 | 73.61 | 53.3 |
| BC-Nantes | | | | | | | | |
| OLFM4 | 0.8543 | 64.3 | 87.7 | 30 | 57.89 | 33.9 | 49.71 | 41 |
| NENF | 0.7169 | 53.8 | 81.5 | 15.6 | 30.41) | 25.9 | 17.54 | 39.0 |
| OLFM4 + NENF | 0.8811 | 75.8 | 87.34 | 38.4 | 71.34 | 43.5 | 63.06 | 53.7 |
| BC-2 | | | | | | | | |
| OLFM4 | 0.8869 | 78.62 | 82.5 | 29.4 | 64.78 | 33.9 | 53.46 | 40.9 |
| NENF | 0.7442 | 60.33 | 76.92 | 13.8 | 34 | 25.9 | 22.33 | 39 |
| OLFM4 + NENF | 0.9146 | 82.32 | 87.34 | 38.3 | 77.17 | 43.5 | 62.06 | 53.7 |
| T1a-T1b-1 | | | | | | | | |
| OLFM4 | 0.9189 | 83.81 | 88.21 | 30.8 | 79 | 33.6 | 66.67 | 42 |
| NENF | 0.7111 | 51.06 | 82.56 | 16.3 | 29.79 | 25.9 | 14.89 | 39.5 |
| OLFM4 + NENF | 0.9177 | 87.62 | 86.08 | 37.8 | 80 | 43.5 | 68.57 | 53.6 |
| T1a-T1b-Nantes | | | | | | | | |

TABLE 7-continued

Area under the ROC curve, sensitivity and specificity values for diagnostic tests based on OFLM4, NENF or OLFM4 + NENF (second study)

|  | AUC (95% CI) | Sensitivity (%) | Specificity (%) | cutoff (ng/ml) | 90% Specificity Sensitivity (%) (95% CI) | cutoff (ng/ml) | 95% Specificity Sensitivity (%) (95% CI) | cutoff (ng/ml) |
|---|---|---|---|---|---|---|---|---|
| OLFM4 | 0.8828 | 77.24 | 88.21 | 30.6 | 73.17 | 33.9 | 67.48 | 41.9 |
| NENF | 0.7363 | 59.35 | 81.54 | 15.6 | 37.4 | 26 | 19.51 | 39 |
| OLFM4 + NENF T1a-T1b-2 | 0.9029 | 78.05 | 92.41 | 45.6 | 78.05 | 43.5 | 71.54 | 53.7 |
| OLFM4 | 0.8778 | 79.61 | 83.08 | 27.5 | 68.93 | 33.9 | 51.46 | 41.8 |
| NENF | 0.7141 | 43.3 | 87.69 | 19.8 | 30.93 | 26.1 | 20.62 | 39.7 |
| OLFM4 + NENF BC-3 cohorts | 0.8986 | 83.33 | 84.18 | 35.4 | 74.07 | 43.5 | 60.19 | 53.7 |
| OLFM4 | 0.8769 | 70.17 | 88.21 | 30.8 | 65.67 | 34 | 55.67 | 41.4 |
| NENF | 0.7348 | 52.92 | 81.54 | 15.6 | 33.71 | 25.9 | 19.1 | 39 |
| OLFM4 + NENF T1a-T1b-3 cohorts | 0.9083 | 81.87 | 87.34 | 38.3 | 77.19 | 43.5 | 65.94 | 53.6 |
| OLFM4 | 0.8927 | 77.64 | 88.21 | 30.6 | 73.72 | 336 | 63.75 | 40.9 |
| NENF | 0,7238 | 53.18 | 81.54 | 15.6 | 31.98 | 26 | 19.16 | 38.7 |
| OLFM4 + NENF | 0.9061 | 82.14 | 87.34 | 38.4 | 77.38 | 43.5 | 66.96 | 53.6 |

2.13. DSP is Decreased in Sera of Patients with Early Tumors and Increased in Sera of Patients with Recurrent Tumors To evaluate the potential of DSP to discriminate small tumors (low DSP) and recurrent tumors (high DSP) from controls, the serum concentrations in 65 healthy subjects and in 384 with breast cancer were determined (first study). DSP was found to be significantly elevated (p=0.0069) in recurrent tumor sera, according our tumor proteomic approach. Conversely, DSP was found significantly decreased (p=0.0037) in small tumors with a size <1 cm (pT1a and pT1b tumors (FIG. 4). This low-DSP serum concentration was consistent with the mammary cell line proteomic results.

2.13. OLFM4, NENF and DSP are Biomarkers of Breast Cancer

The proportion of patients tested positive for OLFM4, NENF and DSP were showed in FIG. 5 (first study). OLFM4 showed significant elevation in 208 breast cancer sera (335 sera in the total cohort). Among 127 patients who were negative for OLFM4, 58 were positive for NENF. Among the last 69 patients who were negative for OLFM4 and NENF, 39 were positive for low-DSP. At least, 30 patients were negative for the three biomarkers (FIG. 5). It should be noted that among this cohort of 335 patients, 32 patients have a high-DSP level (>1800 pg/ml). Among these 32 patients, 12 were in a recurrence state (38%).

2.14. OLFM4, Low-DSP and NENF are Biomarkers for Breast Cancer in the Early Phase To further evaluate the potential of OLFM4, NENF and low-DSP as serum breast cancer in the early phase biomarkers, their serum concentrations were determined in a first study based on 65 healthy subjects and in 81 patients with a small tumor (<1 cm), which represents early breast cancer. The proportion of subjects tested positive for OLFM4 was 65% and this proportion did not increase when the patients tested positive for NENF were added, suggesting that NENF might not be a biomarker of the early breast tumor. Nevertheless, adding the subjects positive for low-DSP, 91% of patients were detected positive (FIG. 6A). A predictor combining OLFM4 and low-DSP information was built by using a logistic regression model. This predictor showed an AUC=0.92 for early breast cancer patients compared to a population without cancer. The sensitivity of the test was 87%, and the specificity was 84% (FIG. 6D).

In the second validation study which was carried out on a much larger cohort of patients, the potential of OLFM4 and NENF was further evaluated as serum biomarkers in the early phase of breast cancer. To this end, their serum concentrations were determined in 336 patients with a small tumor (<1 cm) divided in 3 independent cohorts (105 patients for T1ab-1, 123 patients for T1ab-2 and 108 patients for T1ab-3).

As for the BC cohorts, the median concentration for OLFM4 and NENF were found to be significantly elevated (p<0.0001) in T1a-T1b breast tumors sera as compared to healthy samples (FIGS. 9A and 9C). The values did not differ significantly between the three cohorts, and were similar with the BC cohorts. When the 3 independent breast cancer sera cohorts were combined, the OLFM4 median concentration was determined to be of 51.89 ng/ml (IQR 32.69-83.52) and the NENF median concentration of 17.40 ng/ml (IQR 7.56-30.99).

ROC curves showed that the AUC for OLFM4 in the T1a-T1b cohort was slightly higher than in the BC cohort (0.89 and 0.88 respectively) while the AUC values for NENF were identical (Table 7 and FIG. 9D). When both markers were combined, the median concentrations were identical in the T1a-T1b cohorts and in the BC-cohorts (FIG. 10). In the same manner, the ROC curves were superimposable. When the proportion of patients who were positive to OLFM4, NENF and OLFM4+NENF were compared in the different specificity conditions, the results appeared to be very closed to that obtained for the BC-cohorts. In addition, the ROC curves for OLFM4 in BC and T1a-T1b cohorts were superimposed.

The analyses of positive patients for OLFM4, NENF and OLFM4 plus NENF showed results comparable to those obtained in BC cohorts. The proportion of patients who were positive for OLFM4 or NENF at the optimum cutoff value of the ROC curve was 86%. At 90% specificity, this proportion was 78% and at 95% specificity, 67%. When combining OLFM4 plus NENF, the proportion of patients who were positive for OLFM4+NENF, or OLFM4 alone or NENF alone was also 86% at the optimum cutoff value, this value was 79% at 90% specificity and 69% to 95% specificity.

3. CONCLUSION

The aim of the present studies was to use an innovative proteomic approach to identify novel breast cancer biomarkers. Starting from the fact that no serious candidate had been highlighted with the usual approaches, the present work was focused on secreted proteins that had never been described as potential biomarkers of breast cancer. The first step was to create a protein database from a transformed breast cell line, and from luminal A, Her2-overexpressed and triple negative breast tumors with a global proteomic approach. The identified proteins were compared with the HUPO Plasma project database and Mann's work to be sure these proteins could be detected in the blood of patients. Then, the identified proteins were compared with the Breast Cancer database and over a hundred secreted proteins which were never tested in breast pathology were identified.

Among these proteins, the inventors have more specifically identified OLFM4, NENF and DSP as novel breast cancer biomarkers, easily detectable in sera from patients suffering from such cancer.

Indeed, based on the first study conducted by the inventors, elevation of OLFM4 and NENF, as well as dysregulation of DSP allows the detection of breast cancer. In the case of breast cancer prevention (small tumor detection), it appeared that an elevation of OLFM4 and a decrease of DSP (<600 pg/ml) should be preferably searched. In the case of breast cancer monitoring, an elevation of DSP (>1800 pg/ml) should be searched to identify a breast cancer recurrence.

The second study was carried out by the inventors on a larger cohort of patients with three independent sera cohorts, in order to further evaluate the breast cancer biomarkers NENF and OLFM4. When the diagnostic accuracy of the combination of both biomarkers was evaluated to distinguish breast cancer patients from healthy controls using a generalized ROC criterion, a very significant overall diagnostic accuracy was observed. By bringing together the 3 sera sets, an AUC of 91% with a sensitivity of 82% and a specificity of 87% were obtained. Very interestingly, these values remained elevated in early stage breast cancer patients (tumor size inferior to 1 cm), and the sensitivity and specificity differed slightly between the different sera cohorts. The diagnostic capabilities of serum OLFM4 and NENF were similar in all breast cancer and in early-stage breast cancer patient cohorts. Moreover, the association of the two markers was really beneficial for diagnosis prediction. In the breast cancer set, 421 patients (70%) were positive for OLFM4 alone and 342 patients (53%) were positive for NENF alone. When both markers were combined, 556 patients (85%) were detected. In the same way, for the early-stage breast cancer cohort, 78% of patients were positive for OLFM4 and 53% for NENF alone. This number rose to 82% when OLFM4 and NENF concentrations were combined.

The present data therefore indicate that the serum biomarkers OLFM4, NENF and DSP, and more preferably OFLM4 and NENF, can be used to detect breast cancer, especially in the early-stage diagnosis. As those proteins are secreted, their expression can be simply measured in a reliable manner, without the need for invasive techniques in order to detect breast cancer early on, either combined with mammogram to increase the rate of detected occult cancer, either by spacing the number of mammograms in the patient monitoring.

The potential benefit from a detection methodology designed to identify early-stage breast cancer is clear. Mammography has been shown to be the most effective screening tool for detecting breast cancer early and for saving lives. However, mammography has intrinsic limitations that may be difficult to overcome and its sensitivity ranges between 63 and 87%, depending on age, breast density, and tumor characteristics. Therefore, complementary tests are needed to detect women with breast cancer and to increase the diagnosis sensitivity of screening approaches. Serum biomarkers may be helpful to increase the positive predictive value of mammographic lesions, thereby decreasing the number of women who undergo unnecessary biopsies. In addition, biomarkers may also be used to select cases for more sensitive diagnostic techniques, such as magnetic resonance imaging. Another significant application will be the monitoring of young women "at risk". Women at a high risk of developing breast cancer are essentially those carrying BRCA1 and BRCA2 gene mutations or with a high likelihood of a hereditary predisposition to breast cancer. Consequently, screening is reinforced in women carrying these mutated genes: they should undergo twice-yearly clinical examinations and imaging tests as soon as they reach the age of 30.

Since 2004, several prospective trials have compared breast imaging techniques in women expressing these mutations or at a high-risk of breast cancer. All the trials found MRI superior to the other techniques for the early detection of breast cancer. Sardanelli et al. (2007) analysed the results of 5 prospective studies assessing the performances of mammography, ultrasound and breast MRI: the sensitivity of breast MRI is high (80% versus 40% for mammography), but its predictive value of MRI is low, i.e. only 53%, indicating that the number of biopsies for false-positive results increased with the test. Prophylactic bilateral mastectomy may reduce the risk of breast cancer onset by 85 to 100% but no data have shown the benefits of such a procedure in terms of overall survival compared to monitoring and early screening. The studies also found no survival benefits when prophylactic mastectomy was performed at an early stage, as early as 25 years.

Simple monitoring involving two yearly clinical examinations, breast MRI and a mammogram is an alternative associated with hardly any complications. The procedure does not reduce the risk of cancer, but aims to detect and treat precancer and cancer lesions as early as possible.

The data submitted herein clearly demonstrate that the use of the serum biomarkers OLFM4 and/or NENF, potentially along with DSP, would enhance this positive predictive value while maintaining a good sensitivity.

REFERENCES

Independent UK Panel on Breast Cancer Screening (2012). *The Lancet;* 380(9855): 1778-1786.
Liu W., Chen L., Zhu J., and Rodgers G. P. (2006). *Exp. Cell Res.;* 312: 1785-1797.
Zhang X., Huang Q., Yang Z., Li Y., and Li C. Y. (2004). *Cancer Res.;* 64:2474-2481.
Kobayashi D., Koshida S., Moriai R., Tsuji N., and Watanabe N. (2007). *Cancer Sci.;* 98(3): 334-340.
Kimura I., Nakayama Y., Zhao Y., Konishi M., and Itoh N. (2013). *Front Neurosci.;* 25; 7:111.

Leung C. L., Green K. J., and Liem R. K. (2002). *Trends Cell Biol.;* 12: 37-45.

Allen E., Yu Q. C., and Fuchs E. (1996). *J. Cell Biol.;* 133: 1367-1382.

Wan H., South A. P., and Hart I. R. (2007). *Exp. Cell Res.;* 313: 2336-2344.

Rickelt S., Winter-Simanowski S., Noffz E., Kuhn C., and Franke W. W. (2009). *Int. J. Cancer;* 125: 2036-2048.

Jonkman M. F., Pasmooij A. M., Pasmans S. G., Van Den Berg M. P., Ter Horst H. J., Timmer A., and Pas H. H. (2005). *Am. J. Hum. Genet.;* 77: 653-660.

Kowalczyk A. P., Bornslaeger E. A., Borgwardt J. E., Palka H. L., Dhaliwal A. S., Corcoran C. M., Denning M. F., and Green K. J. (1997). *J. Cell Biol.;* 139: 773-784.

Dowdy S. M., and Wearden S. (1983). Statistics for Research, John Wiley & Sons, New York.

Hou H. W., Warkiani M. E., Khoo B. L., Li Z. R., Soo R. A., Tan D. S., Lim W. T., Han J., Bhagat A. A., Lim C. T. (2013). *Sci. Rep.;* 3:1259.

Reeves J. R. and Bartlett J. M. S. (2000). *Methods in Molecular Medicine;* vol. 39, chapter 51, p. 471-483.

Schena M. (2005). Protein microarrays; Jones and Bartlett Learning.

Hamelinck D., Zhou H., Li L., Verweij C., Dillon D., Feng Z., Costa J., and Haab B. B. (2005). *Mol. Cell Proteomics;* 4(6):773-84.

Köhler G. and Milstein C. (1975). *Nature;* 256 (5517): 495-7.

Kozbor D., Roder J. C. (1983). *Immunology Today;* vol. 4: p. 72-79.

Roder J. C., Cole S. P., and Kozbor D. (1986). *Methods Enzymol.;* 121:140-167.

Huse W. D., Sastry L., Iverson S. A., Kang A. S., Alting-Mees M., Burton D. R., Benkovic S. J., and Lerner R. A. (1989). *Science;* 246:1275-1281.

Weigelt B. and Bissell M. J. (2008). *Semin Cancer Biol.;* 18(5): 311-321.

Kenny P. A., Lee G. Y., Myers C. A., Neve R. M., Semeiks J. R., Spellman P. T., Lorenz K., Lee E. H., Barcellos-Hoff M. H., Petersen O. W., Gray J. W., and Bissell M. J. (2007). *Mol Oncol.;* 1(1):84-96.

Li Q., Chow A. B., and Mattingly R. R. (2010). *J Pharmacol Exp Ther.;* 332(3): 821-828.

Mitchell P. (2002). *Nature Biotech;* 20: 225-229.

Haab B. B. (2005). *Mol Cell Proteomics;* 4(4):377-83.

Eckel-Passow J. E., Hoering A., Therneau T. M., and Ghobrial I. (2005). *Cancer Res;* 15; 65(8):2985-9.

Kingsmore S. F. (2006). *Nat Rev Drug Discov.;* 5(4):310-20.

Chandra H., Reddy P. J., and Srivastava S. (2011). *Expert Rev Proteomics;* 8(1):61-79

Schenk S., Schoenhals G. J., de Souza G., and Mann (2008). *BMC Med Genomics;* 15; 1:41.

Cao Z., Yende S., Kellum J. A., and Robinson R. A. S. (2013). *Int J Proteomics:* 2013:654356.

Imbalzano K. M., Tatarkova I., Imbalzano A. N., and Nickerson J. A. (2009). *Cancer Cell Int.* 9:7. doi: 10.1186/1475-2867-9-7.

Wiśniewski J R., Zougman A., Nagaraj N., and Mann M. (2009). *Nat Methods;* 6, 359-362.

Shilov I. V., Seymour S. L., Patel A. A., Loboda A., Tang W. H., Keating S. P., Hunter C. L., Nuwaysir L. M., and Schaeffer D. A. (2007). *Mol Cell Proteomics;* 6, 1638-1655.

Schwacke, J. H., Hill, E. G., Krug, E. L., Comte-Walters, S., and Schey, K. L. (2009). *BMC Bioinformatics;* 10, 342.

Grant J. E., Bradshaw A. D., Schwacke, J. H, Baicu, C. F., Zile, M. R., and Schey, K. L. (2009). *J Proteome Res.;* 9, 4252-63.

Konishi H., Karakas B., and Abde M. Abukhdeir A. M. (2007). *Cancer Res.;* 67:8460-8467.

Sardanelli F., and Podo F. (2007). *Eur Radiol.;* 17:873-87.

The invention claimed is:

1. An in vitro method, comprising the steps of:
   a) obtaining a biological fluid sample from a subject; and
   b) detecting, the biological fluid sample, protein expression levels of the three biomarkers Olfactomedin-4, Neudesin, and Desmoplakin, wherein the protein expression level of Neudesin is superior to 16 ng/mL or wherein the protein expression level of Olfactomedin-4 is superior to 31 ng/mL, and wherein the protein expression level of Desmoplakin is superior to 1800 pg/mL or inferior to 600 pg/mL.

2. An in vitro method, comprising the steps of:
   a) obtaining a biological fluid sample from a subject; and
   b) detecting, the biological fluid sample, protein expression levels of the three biomarkers Olfactomedin-4, Neudesin, and Desmoplakin, wherein the combined protein expression level of Olfactomedin-4 and Neudesin is superior to 38 ng/mL, and wherein the protein expression level of Desmoplakin is superior to 1800 pg/mL or inferior to 600 pg/mL.

3. An in vitro method, comprising the steps of:
   a) obtaining a biological fluid sample from a subject; and
   b) detecting, the biological fluid sample, protein expression levels of the three biomarkers Olfactomedin-4, Neudesin, and Desmoplakin, wherein the protein expression level of Desmoplakin is superior to 1800 pg/mL or inferior to 600 pg/mL.

4. The method according to claim 1, further comprising the step of detecting a protein expression level of at least one standard biomarker associated with breast cancer, said standard biomarker being selected from the group consisting of estrogen receptor (ER), progesterone receptor (PR), and human epidermal growth factor receptor 2 (HER2).

5. The method according to claim 1, wherein said biological fluid is selected from the group consisting of blood, serum, plasma, lymph, tumor interstitial fluid, saliva, mucus, sputum, sweat, and urine.

6. The method according to claim 5, wherein said biological fluid is serum.

7. The method according to claim 1, wherein the protein expression levels are detected by a method selected from the group consisting of Western blot, immunoblot, enzyme-linked immunosorbant assay (ELISA), enzyme-linked immunospot (ELISPOT), radioimmunoassay (RIA), immunohistochemistry, immunoprecipitation, fluorescence activated cell sorting (FACS), microscopy, flow cytometry, microcytometry, protein binding assay, ligand binding assay, microarray, polyacrylamide gel electrophoresis such as SDS-PAGE, surface plasmon resonance (SPR), Förster resonance energy transfer (FRET), Bioluminescence resonance energy transfer (BRET), chemiluminescence, fluorescent polarization, phosphorescence, mass spectrometry, magnetic resonance imaging (MRI), and any combination thereof.

8. The method according to claim 2, further comprising the step of detecting a protein expression level of at least one standard biomarker associated with breast cancer, said standard biomarker being selected from the group consisting of estrogen receptor (ER), progesterone receptor (PR), and human epidermal growth factor receptor 2 (HER2).

9. The method according to claim 2, wherein said biological fluid is selected from the group consisting of blood, serum, plasma, lymph, tumor interstitial fluid, saliva, mucus, sputum, sweat, and urine.

10. The method according to claim 9, wherein said biological fluid is serum.

11. The method according to claim 2, wherein the protein expression levels are detected by a method selected from the group consisting of Western blot, immunoblot, enzyme-linked immunosorbant assay (ELISA), enzyme-linked immunospot (ELISPOT), radioimmunoas say (RIA), immunohistochemistry, immunoprecipitation, fluorescence activated cell sorting (FACS), microscopy, flow cytometry, microcytometry, protein binding assay, ligand binding assay, microarray, polyacrylamide gel electrophoresis such as SDS-PAGE, surface plasmon resonance (SPR), Förster resonance energy transfer (FRET), Bioluminescence resonance energy transfer (BRET), chemiluminescence, fluorescent polarization, phosphorescence, mass spectrometry, magnetic resonance imaging (MRI), and any combination thereof.

12. The method according to claim 3, further comprising the step of detecting a protein expression level of at least one standard biomarker associated with breast cancer, said standard biomarker being selected from the group consisting of estrogen receptor (ER), progesterone receptor (PR), and human epidermal growth factor receptor 2 (HER2).

13. The method according to claim 3, wherein said biological fluid is selected from the group consisting of blood, serum, plasma, lymph, tumor interstitial fluid, saliva, mucus, sputum, sweat, and urine.

14. The method according to claim 13, wherein said biological fluid is serum.

15. The method according to claim 3, wherein the protein expression levels are detected by a method selected from the group consisting of Western blot, immunoblot, enzyme-linked immunosorbant assay (ELISA), enzyme-linked immunospot (ELISPOT), radioimmunoas say (RIA), immunohistochemistry, immunoprecipitation, fluorescence activated cell sorting (FACS), microscopy, flow cytometry, microcytometry, protein binding assay, ligand binding assay, microarray, polyacrylamide gel electrophoresis such as SDS-PAGE, surface plasmon resonance (SPR), Förster resonance energy transfer (FRET), Bioluminescence resonance energy transfer (BRET), chemiluminescence, fluorescent polarization, phosphorescence, mass spectrometry, magnetic resonance imaging (MRI), and any combination thereof.

* * * * *